US008168613B2

(12) United States Patent
Cohen et al.

(10) Patent No.: US 8,168,613 B2
(45) Date of Patent: May 1, 2012

(54) INJECTABLE CROSS-LINKED POLYMERIC PREPARATIONS AND USES THEREOF

(75) Inventors: Smadar Cohen, Beer-Sheva (IL); Jonathan Leor, Chedera (IL)

(73) Assignee: Ben Gurion University of the Negev Research and Development Authority, Beer-Sheva (IL)

( * ) Notice: Subject to any disclaimer, the term of this patent is extended or adjusted under 35 U.S.C. 154(b) by 356 days.

(21) Appl. No.: 12/647,295

(22) Filed: Dec. 24, 2009

(65) Prior Publication Data

US 2010/0173867 A1 Jul. 8, 2010

Related U.S. Application Data

(60) Division of application No. 11/229,119, filed on Sep. 19, 2005, which is a continuation-in-part of application No. 10/840,008, filed on May 5, 2004, now abandoned, and a continuation-in-part of application No. PCT/IL2004/000371, filed on May 4, 2004.

(30) Foreign Application Priority Data

May 5, 2003 (IL) .......................................... 155774

(51) Int. Cl.
*A01N 43/04* (2006.01)
(52) U.S. Cl. ........................................................ 514/54
(58) Field of Classification Search .................... 514/54
See application file for complete search history.

(56) References Cited

U.S. PATENT DOCUMENTS

| 4,717,713 A | 1/1988 | Satz et al. |
| 5,614,204 A | 3/1997 | Cochrum |
| 5,667,778 A | 9/1997 | Atala |
| 5,709,854 A | 1/1998 | Griffith-Cima et al. |
| 5,738,860 A | 4/1998 | Schonfeldt et al. |
| 5,776,445 A | 7/1998 | Cohen et al. |
| 5,924,073 A | 7/1999 | Tyuluman et al. |
| 6,129,761 A | 10/2000 | Hubbell |
| 6,134,334 A | 10/2000 | Killion et al. |
| 6,136,334 A | 10/2000 | Viegas et al. |
| 6,171,610 B1 | 1/2001 | Vacanti et al. |
| 6,190,700 B1 | 2/2001 | Okada et al. |
| 6,360,749 B1 | 3/2002 | Jayaraman |

(Continued)

FOREIGN PATENT DOCUMENTS

CA 2212300 2/1999

(Continued)

OTHER PUBLICATIONS

Leor, Jonathan et al., "A Novel Injectable Alginate Scaffold Promotes Angiogenesis and Preserves Left Ventricular Geometry and Function after Extensive Myocardial Infarction in Rat", *Circulation 2004*, 2 pgs.

(Continued)

*Primary Examiner* — Sharmila G. Landau
*Assistant Examiner* — Trevor Love
(74) *Attorney, Agent, or Firm* — Diehl Servilla LLC

(57) ABSTRACT

A therapeutic composition for treatment of a body tissue which includes an aqueous solution of a cross-linked polymer being capable of: (i) maintaining a liquid state in storage at room temperature for at least 24 hours; and (ii) assuming a gel state following deposition within the body tissue. The therapeutic composition can be effectively administered into a damaged body tissue via injection or catheterization, thereby treating the damaged body tissue.

24 Claims, 38 Drawing Sheets

U.S. PATENT DOCUMENTS

| | | | |
|---|---|---|---|
| 6,592,886 | B1 | 7/2003 | Zimmermann |
| 6,680,184 | B2 | 1/2004 | Nussinovitch |
| 7,214,371 | B1 | 5/2007 | Cohen et al. |
| 2003/0078672 | A1 | 4/2003 | Shapiro et al. |
| 2004/0106896 | A1 | 6/2004 | Lee et al. |
| 2004/0208845 | A1 | 10/2004 | Michal et al. |
| 2005/0003010 | A1 | 1/2005 | Cohen et al. |
| 2005/0288325 | A1 | 12/2005 | MacLean |
| 2006/0083721 | A1 | 4/2006 | Cohen et al. |
| 2006/0263407 | A1 | 11/2006 | Mishra |

FOREIGN PATENT DOCUMENTS

| | | |
|---|---|---|
| CA | 2523556 | 11/2004 |
| EP | 1270594 | 1/2003 |
| WO | WO-94/25080 | 11/1994 |
| WO | WO-97/44070 | 11/1997 |
| WO | WO-99/15211 | 4/1999 |
| WO | WO-03/054182 | 7/2003 |
| WO | WO-2004/098669 | 11/2004 |
| WO | WO-2005/066337 | 7/2005 |

OTHER PUBLICATIONS

Final Office Action in U.S. Appl. No. 11/229,119, dated Aug. 11, 2010, 31 pgs.
IPRP in PCT/IL2004/000371, Aug. 5, 2005, 11 pgs.
ISR in PCT/IL2004/00371, dated Sep. 16, 2004.
Non-Final Office Action in U.S. Appl. No. 11/229,119, dated Feb. 17, 2010, 30 pgs.
NovaMatrix, Pronova UP MVG, Last accessed Feb. 4, 2010, 1-4 pgs.
Written Opinion in PCT/IL2004/000371, Aug. 5, 2005, 9 pgs.
Abbate, et al., "Pathophysiologic Role of Myocardial Apoptosis in Post-Infarction Left Ventricular Remodeling", Journal of Cellular Physiology, 193(2). Abstract 2002, 145-153 pgs.
Abbate, et al., "Persistent Infarct-Related Artery Occlusion Is Associated With an Increased Myocardial Apoptosis at Postmortem Examination in Humans Late After an Acute Myocardial Infarction", Circulation, 106 2002, 1051-1054 pgs.
Aebischer, et al., "Transplatation in Humans of Encapsulated Xenogeneic Cells Without Immunosupression", Transplantation, 58(11) 1994, 1275-1277 pgs.
Askari, et al., "Effect of Stromal-Cell-Derived Factor 1 on Stem-Cell Homing and Tissue Regeneration in Ischaeic Cardiomyopathy", The Lancet, 362(9385) 2003, 697-703 pgs.
Atala, et al., "Injectable Alginate Seeded With Chondrocytes as a Potential Treatment for Vesicoureteral Reflux", The Journal of Urology, 150 1993, 745-747 pgs.
Babiak, et al., "Coordinated Activation of VEGFR-1 and VEGDR-2 Is a Potent Arteriogenic Stimulus Leading to Enhancement of Regional Perfusion", Cardiovascular Research, 61 2004, 789-795 pgs.
Becker, et al., "Calcium Alginate Gel: A Biocompatible and Mechanically Stable Polymer for Endovascular Embolization", Journal of Biomedical Materials Research, 54 2001, 76-86 pgs.
Becker, et al., "Flow Properties of Liquid Calcium Alginate Polymer Injected Through Medical Microcatheters for Endovascular Embolization", Journal of Biomedical Materials Research, 61 2002, 533-540 pgs.
Beltrami, et al., "Adult Cardiac Stem Cells Are Multipotent and Support Myocardial Regeneration", Cell, 114 2003, 763-776 pgs.
Braunwald, , "Myocardial Reperfusion, Limitation of Infarct Size, Reduction of Left Ventricular Dysfunction, and Improved Survival", Circulation, 79 1989, 441-444 pgs.
Broxmeyer, et al., "Stromal Cell-Derived Factor-1/CXCL12 Directly Enhances Survival/Antiapoptosis of Myeloid Progenitor Cells Through CXCR4 and Zai Proteins and Enhances Engraftment of Competitive, Repopulating Stem Cells", Journal of Leukocyte Biology, 73(5) 2003, 630-638 pgs.
Cohen, et al., "A Novel in Situ-Forming Ophthalmic Drug Delivery System From Alginates Undergoi9ng Gelation in the Eye", Journal of Controlled Release, 44 1997, 201-208 pgs.
Couffinhal, et al., "Mouse Model of Angiogenesis", American Journal of Pathology, 152(6) 1998, 1667-1679 pgs.

Douglas, et al., "Mechanisms and Models in Heart Failure—A Combinatorial Approach", Circulation, 100 1999, 999-1008 pgs.
Etzion, et al., "Influence of Embryonic Cardiomyocyte Transplantation on the Progression of Heart Failure in a Rat Model of Extensive Myocardial Infarction", Journal of Molecular and Cellular Cardiology, 33 2001, 1321-1330 pgs.
Etzion, et al., "Myocardial Regeneration: Present and Future Trends", American Journal of Cardiovascular Druge, 1(4), Abstract 2001, 233-244 pgs.
Gonzales, et al., "The Neuropeptide Y Y1 Receptor Mediates NPV-Induced Inhitition of the Gonadotrope Axis Under Poor Metabolic Conditions", The FASEB Journal Online 2003.
Gungor, et al., "Investigations on Mefenamic Acid Sustained Release Tablets With Water-Insoluble Gel", II Farmaco 58 2003, 397-401 pgs.
Gutowska, et al., "Injectable Gels for Tissue Engineering", The Anatomical Record 263 2001, 342-349.
Hale, et al., "Left Ventricular Topographic Alterations in the Completely Healed Rat Infarct Caused by Early and Late Coronary Artery Reperfusion", American Heart Journal, 116(pt. 1), Abstract 1988, 1508-1513.
Jessup, et al., "Heart Failure", The New England journal of Medicine, 348 2003, 2007-2018 pgs.
Jugdutt, "Ventricular Remodeling After Infarction and the Extracellular Collagen Matrix: When Is Enough Enough?", Circulation, 108 2003, 1395-1403 pgs.
Kelley, et al., "Restraining Infarct Expansion Preserves Left Ventricular Geometry and Function After Acute Anteroapical Infarction", Circulation, 99(1) 1999, 135-142 pgs.
Khand, et al., "Clinical Events Leading to the Progression of Heart Failure: Insights From a National Database of Hospital Discharges", European Heart Journal, 22 2001, 153-164 pgs.
Knight, et al., "Nonsurgical Septal Reduction for Hypertrophic Obstructive Cardiomyopathy", Circulation, 95 1997, 2075-2081 pgs.
Kollet, et al., "Rapid and Efficient Homing of Human CD34+CD38-LowCXCR4+ Stem and Progenitor Cells to the Bone Marrow and Spleen of NOD/SCID and NOD/SCID/B2mNull Mice", Blood, 97(10) 2001, 3298-3291 pgs.
Lamas, et al., "Clinical Significance of Mitral Regurgitation Fter Acute Myocardial Infarction", Circulation, 96(3) 1997, 827-833 pgs.
Lapidot, et al., "Current Understanding of Stem Cell Mobilization: The Roles of Chemokines, Proteolytic Enzymes, Adhesion Molecules, Cytokines, and Stromal Cells", Experimental Hematology, 30 2002, 973-981 pgs.
Lembcke, et al., "Passive External Cardiac Constraint Improves Segmental Lift Ventricular Wall Motion and Reduces Akinetic Area in Patients With Non-Ischemic Dilated Cardiomyopathy", European Journal of Cardio-Thoracic Surgery, 25, Abstract 2004, 84-90 pgs.
Leor, et al., "Bioengineered Cardiac Grafts: A New Approach to Repair the Infarctged Myocardium?", Circulation, 102 (Suppl. III) 2000, III-56-III-61 pgs.
Leor, et al., "Cell Transplantation and Genetic Engineering: New Approaches to Cardiac Pathology", Expert Opinion in Biological Therapy, 3(7) 2003, 1023-1039 pgs.
Leor, et al., "Transplantationof Fetal Myocardial Tissue Into the Infarcted Myocardium of Rat—A Potential Method for Repair of Infarcted Myocardium", Circulation, 94(9) 1996, 332-336.
Lim, et al., "Microencapsulated Islets as Beoartificial Endocrine Pancreas", Science, 210(4472), Abstract 1980, 908-910 pgs.
Litwin, et al., "Serial Echocardiographic Assessment of Left Ventricular Geometry and Function After Large Myocardial Infarction in the Rat", Circulation, 89(1) 1994, 345-354 pgs.
Madeddu, et al., "Transplantation of Low Dose CD34+Kdr+ Cells Promotes Vascular and Muscular Regeneration in Ischemic Limbs", The FASEB Journal, 18(14) 2004, 1737-1739 pgs.
Mann, "Mechanisms and Models in Heart Failure: A Combinatorial Approach", Circulation, 100(9) 1999, 999-1008 pgs.
McLennan, et al., "Kinetics of Release of Heparin From Alginate Hydrogel", Journal of Vascular and Interventional Radiology, JVIR 11(8) 2000, 1087-1094 pgs.
Mehta, et al., "Functional Infarct Expansion, Left Ventricular Dilation and Isovolumic Relaxation Time After Coronory Occlusion: A Two-Dimensional Echocardigraphic Study", *Journal of the American Coll. Cardiology*, 11(3) 1988, 630-636 pgs.

Perrin, et al., "Transendocardial, Autologous Bone Marrow Cell Transplantation for Severe, Chronic Ischemic Heart Failure", *Circulation*, 107 2003, 2294-2302 pgs.

Pilla, et al., "Ventricular Constraint Using the Acorn Cardiac Support Device Reduces Myocardial Akinetic Area in an Ovine Model of Acute Infarction", *Circulation*, 106 2002, 207-211 pgs.

Pillarisetti, et al., "Cloning and Relative Expression Analysis of Rat Stromal Cell Derived Factor-1 (SDF-1): SDF-1 α mRNA Is Selectively Induced in Rat Model of Myocardial Infarction", *Inflammation*, 25(5), Abstract 2001, 293-300 pgs.

Redfield, "Heart Failure—An Epidemic of Uncertain Proportions", *New England Journal of Medicine*, 347(18), Abstract 2002, 1442-1444 pgs.

Rosenblatt, et al., "Culturing Satellite Cells From Living Single Muscle Fiber Explants", *In Vitro Cell. Dev. Diol.—Animal*, 31 1995, 773-779 pgs.

Saavedra, et al., "Reverse Remodeling and Enhanced Anrenergic Reserve From Passive External Support in Experimental Dilated Heart Failure", *Journal of the American College of Cardiology*, JACC, 39(12) 2002, 2069-2076 pgs.

Salcedo, et al., "Vascular Endothelial Growth Factor and Basic Fibroblast Growth Factor Induce Expression of CXCR4 on Human Endothelial Cells. In Vivo Neovascularization Induced by Stromal-Derived Factor-1 α", *American Journal of Pathology*, 154(4) 1999, 1125-1135 pgs.

Salisburg, et al., "Influence of Coronary Artery Pressure Upon Myocardial Elasticity", *Circulation Research*, VIII 1960, 794-800 pgs.

Salvucci, et al., "Regulation of Endothelial Cell Branching Morphogenesis by Endogenous Chemokine Stromal-Derived Factor-1", *Blood*, 99(8) 2002, 2703-2711 pgs.

Schiller, et al., "Recommendations for Quantitation of the Left Ventrice by Two-Dimensional Echocardiography", *Journal of the American Society of Echocardiography*, 2(5) 1989, 358-367 pgs.

Schwartz, et al., "Evaluation of Cardiac Structures and Function in Small Experimental Animals: Transthoracic, Transesophageal, and Intraventicular Echocardiography to Assess Contractile Functgion in Rat Heart", *Basic Research in Cardiology*, 93(6), Abstract 1998, 477-486 pgs.

Shapiro, et al., "Efficacies of Vaccines Containing Alginate Adjuvant", *J. Appl. Bact. 30(2)* 1967, 304-311 pgs.

Shapiro, et al., "Novel Alginate Sponges for Cell Culture and Transplantation", *Biomaterials 18(8)* 1997, 583-590 pgs.

Suggs, et al., "Preparation and Characterization of Poly (Propylene Fumarate-Co-Ethylene Glycol) Hydrogels", *Journal of Biomater. Sci. Polymer Edn.*, 9(7) 1998, 653-666 pgs.

Sutton, et al., "Left Ventricular Remolding After Myocardial Infarction-Pathophysiology and Therapy", *Circulation*, 101 2000, 2981-2988 pgs.

Tachibana, et al., "The Chemokine Receptor CXCR4 Is Essential for Vascularization of the Gastrointestinal Tract", *Nature*, 393, Abstract 1998, 591-594 pgs.

Tschimirov, et al., "Rheologische Eigenschaften des Systems Calciumalginat-Kartoeffelstarke-Hydrolysat-Wasser", *Die Nahrung*, 23(5) 1979, 501-508 pgs.

Watanabe, et al., "Cardomyocyte Transplantation in a Porcine Myocardial Infarction Model", *Cell Transplantation*, 7(3), Abstract 1998, 239-246 pgs.

Yamaguchi, et al., "Stromal Cell-Derived Factor-1 Effects on Ex Vivo Expanded Endothelial Progenitor Cell Recruitment for Ischemic Neovascularization", *Circulation*, 107(9) 2003, 1322-1328 pgs.

Yau, et al., "Beneficial Effect of Autologous Cell Transplantation on Infarcted Heart Function: Comparison Between Bone Marrow Stromal Cells and Heart Cells", *Annual of Thoracic Surgeons*, 75 2003, 169-177.

Martinsen, Anita "Alginate as Immobilization Material: III. Diffusional Properties", *Biotechnology and Bioengineering*, vol. 39 1992, 186-194.

Ostberg, Tone "Calcium alginate matrices for oral multiple unit administration: II. Effect of process and formulation factors on matrix properties", *International Journal of Pharmaceutics*, 97 1993, 183-193.

Chan, L. W., et al, "Cross-linking mechanisms of calcium and zinc in production of alginate microspheres", International Journal of Pharmaceutics 242, 2002, 4 pgs.

Non-Final Office Action in U.S. Appl. No. 11/229,119, mailed Apr. 7, 2011, 26 pgs.

INJECTABLE CROSS-LINKED POLYMERIC PREPARATIONS AND USES THEREOF

CROSS-REFERENCE TO RELATED APPLICATIONS

This application is a divisional application of U.S. application Ser. No. 11/229,119, filed Sep. 19, 2005, which U.S. application Ser. No. 11/229,119 is a Continuation-In-Part of U.S. patent application Ser. No. 10/840,008, filed on May 5, 2004, now abandoned, which claims priority of Israel Patent Application No. 155774, filed on May 5, 2003, and which U.S. application Ser. No. 11/229,119 is also a Continuation-In-Part of PCT Patent Application No. PCT/IL2004/000371, filed on May 4, 2004, which claims priority to Israel Patent Application No. 155774, filed on May 5, 2003, the entire contents of all of which Applications are all incorporated herein by reference.

FIELD AND BACKGROUND OF THE INVENTION

The present invention relates to cross-linked polymer compositions capable of treating body tissues and, more particularly, to aqueous cross-linked polymer solutions and methods of use thereof.

Cross-linked polymer gel materials are widely utilized in the biomedical industry. For example, polysaccharide gels have been applied in contact lenses, blood contact materials, controlled release formulations, wound dressings, bioadhesives, membranes, superabsorbents, cell encapsulation and immunoisolation materials, and tissue engineering scaffolds (Suggs et al., J. Biomater. Sci. Polym. 9: 653-666, 1998; Aebischer et al., Transplantation 58: 1275-1277, 1994; and Atala et al. (J. Urol. 150: 745-747, 1993).

The potential use of polysaccharide gel materials for treating damaged heart tissue has been intensively researched during the past decade.

The main focus of research has been on utilizing polysaccharide gels for treating the heart tissue following myocardial infarction (MI). MI typically causes an acute loss of myocardial tissue and an abrupt increase in loading conditions which induces left ventricular (LV) remodeling. The early phase of LV remodeling involves expansion of the infarct zone, which often results in early ventricular rupture or aneurysm formation. Late remodeling encompasses the entire LV and involves time-dependent dilatation, recruitment of border zone myocardium into the scar, distortion of ventricular shape and mural hypertrophy. Consequently, it may lead to progressive deterioration in contractile function, heart failure and eventually death (Sutton and Sharpe, Circulation 101:2981-2988, 2000; Mann, D. L., Circulation 100:999-1008, 1999; and Jugdutt, B. I., Circulation 108:1395-1403, 2003).

Accordingly, cessation or reversal of progressive chamber remodeling is an important aim of heart failure therapy. Clinical attempts to minimize the devastating effects of MI have thus far failed to effectively repair the irreversible damage inflicted to the heart tissue (Khand et al., Eur. Heart J. 22:153-164, 2001; Jessup and Brozena, S. N. Engl. J. Med. 348:2007-2018, 2003; and Redfield, M. M., N. Engl. J. Med. 347:1442-1444, 2000).

Recently, attempts to implant living cells in damaged myocardium have given hope for repairing the damaged tissue via promoting tissue regeneration (Etzion et al., J. Mol. Cell. Cardiol. 33:1321-1330, 2000; Leor et al., Expert Opin. Biol. Ther. 3:1023-39, 2003; and Beltrami et al., Cell; 114:763-776, 2003). This approach has advanced considerably with the development of 3-D biomaterial scaffolds aimed at supporting implantation of donor cells (e.g., cardiac cells or stem cells) in the myocardium. Lately, 3-D biomaterial scaffolds made of polysaccharide gel were successfully implanted onto damaged myocardium with promising results (Leor et al., Circulation 102:56-61, 2000). However, clinical use of such cell seeded 3-D biomaterial scaffolds is limited due to scarcity of suitable donor cells and the high risk involved in major surgery.

While reducing the present invention to practice, the present inventors generated a stable solution of a cross-linked polymer which can be safely administered into a body tissue, such as a damaged myocardium, using low invasive techniques and which can effectively repair the damaged tissue.

SUMMARY OF THE INVENTION

According to one aspect of the present invention there is provided a therapeutic composition for treatment of a body tissue. The therapeutic composition includes an aqueous solution of a cross-linked polymer being capable of: (i) maintaining a liquid state in storage at room temperature for at least 24 hours; and (ii) assuming a gel state following deposition within the body tissue.

According to another aspect of the present invention there is provided a therapeutic composition for treatment of a body tissue. The therapeutic composition includes an aqueous solution of a cross-linked polymer being capable of: (i) maintaining a liquid state within a blood vessel; and (ii) assuming a gel state following deposition within the body tissue.

According to yet another aspect of the present invention there is provided an article of manufacturing, including the therapeutic composition and a packaging material identifying the therapeutic composition for use in tissue repair.

According to still another aspect of the present invention there is provided a kit for treatment of a body tissue. The kit includes: (a) the therapeutic composition; (b) a device suitable for administering the therapeutic composition into the body tissue; and (c) a packaging material identifying the kit for use in treatment of the body tissue.

According to an additional aspect of the present invention there is provided a method of producing a therapeutic composition for treatment of a body tissue. The method is effected by: (a) providing an aqueous solution containing a predetermined multivalent cation salt to polymer salt ratio; and (b) mixing the aqueous solution under conditions suitable for uniformly cross linking the polymer of the polymer salt with the multivalent cation of the multivalent cation salt and yet maintains the aqueous solution as an aqueous cross-linked polymer solution, thereby producing the therapeutic composition for treatment of a body tissue.

According to yet an additional aspect of the present invention there is provided a method of treating a damaged body tissue. The method is effected by providing the damaged body tissue with an effective amount of the therapeutic composition.

According to still an additional aspect of the present invention there is provided a method of treating a heart condition. The method is effected by providing a heart tissue with an effective amount of the therapeutic composition.

According to a further aspect of the present invention there is provided a method of inducing angiogenesis in a damaged heart tissue. The method is effected by providing the damaged heart tissue with an effective amount of the therapeutic composition.

According to further features in preferred embodiments of the invention described below, the therapeutic composition is further capable of maintaining a liquid state in storage at a temperature ranging from about 4 to about 8° C. for at least 30 days.

According to still further features in the described preferred embodiments the therapeutic composition is further being capable of maintaining the liquid state within a blood vessel.

According to still further features in the described preferred embodiments the therapeutic composition is further being capable of spreading from the blood vessel to the body tissue.

According to still further features in the described preferred embodiments the aqueous solution of a cross-linked polymer is administrable into the body tissue via a needle.

According to still further features in the described preferred embodiments the needle has an 18-27 gauge bore.

According to still further features in the described preferred embodiments the aqueous solution of a cross-linked polymer is administrable via infusion or catheterization.

According to still further features in the described preferred embodiments the blood vessel is an artery.

According to still further features in the described preferred embodiments the artery is a coronary artery.

According to still further features in the described preferred embodiments the aqueous solution of a cross-linked polymer exhibits: (i) an elastic response being equal to or greater than its viscous response under small deformation oscillatory frequencies in the linear viscoelastic limit; and (ii) shear thinning behavior in a power-law relationship.

According to still further features in the described preferred embodiments the small deformation oscillatory frequencies range from 0.01 to 100 Hz.

According to still further features in the described preferred embodiments the small deformation oscillatory frequencies range from 0.1 to 10 Hz.

According to still further features in the described preferred embodiments the polymer is a polysaccharide.

According to still further features in the described preferred embodiments the polysaccharide is an alginate.

According to still further features in the described preferred embodiments the alginate has a molecular weight ranging from 1 to 300 kDa.

According to still further features in the described preferred embodiments the alginate has a molecular weight ranging from 5 to 200 kDa.

According to still further features in the described preferred embodiments the alginate has a molecular weight ranging from 10 to 100 kDa.

According to still further features in the described preferred embodiments the alginate has a molecular weight ranging from 20 to 50 kDa.

According to still further features in the described preferred embodiments a concentration of the alginate in the aqueous solution of a cross-linked polymer ranges from 0.1 to 4% (w/v).

According to still further features in the described preferred embodiments a concentration of the alginate in the aqueous solution of a cross-linked polymer ranges from 0.5 to 2% (w/v).

According to still further features in the described preferred embodiments a concentration of the alginate in the aqueous solution of a cross-linked polymer ranges from 0.8 to 1.5% (w/v).

According to still further features in the described preferred embodiments a concentration of the alginate in the aqueous solution of a cross-linked polymer is about 1% (w/v).

According to still further features in the described preferred embodiments the polymer is cross-linked by multivalent cations.

According to still further features in the described preferred embodiments the multivalent cations are uniformly distributed within the polymer.

According to still further features in the described preferred embodiments the multivalent cations are calcium cations.

According to still further features in the described preferred embodiments a concentration of the calcium cations in the aqueous solution of a cross-linked polymer ranges from 0.005 to 0.1% (w/v).

According to still further features in the described preferred embodiments a concentration of the calcium cations in the aqueous solution of a cross-linked polymer ranges from 0.01 to 0.05% (w/v).

According to still further features in the described preferred embodiments a concentration of the calcium cations in the aqueous solution of a cross-linked polymer ranges from 0.02 to 0.04% (w/v).

According to still further features in the described preferred embodiments a concentration of the calcium cations in the aqueous solution of a cross-linked polymer ranges from 0.025 to 0.035% (w/v).

According to still further features in the described preferred embodiments a monomer ratio between $\alpha$-L-guluronic acid and $\beta$-D-mannuronic acid in the alginate ranges between 1:1 and 3:1.

According to still further features in the described preferred embodiments a monomer ratio between $\alpha$-L-guluronic acid and $\beta$-D-mannuronic acid in the alginate ranges between 1.5:1 and 2.5:1.

According to still further features in the described preferred embodiments a monomer ratio between $\alpha$-L-guluronic acid and $\beta$-D-mannuronic acid in the alginate is about 2.

According to still further features in the described preferred embodiments the therapeutic composition further includes cells.

According to still further features in the described preferred embodiments the cells are selected from the group consisting of cardiomyocetes, myoblasts, fibroblasts, chondrocytes, muscle cells, smooth muscle cells, endothelial cells, mesenchymal cells and stem cells.

According to still further features in the described preferred embodiments the therapeutic composition further includes at least one therapeutic agent According to still further features in the described preferred embodiments the at least one therapeutic agent is selected from the group consisting of a growth factor, a hormone, an anti-inflammatory drug, an anti-apoptotic drug and an antibiotic drug.

According to still further features in the described preferred embodiments the tissue is a myocardial tissue.

According to still further features in the described preferred embodiments the tissue is muscle tissue.

According to still further features in the described preferred embodiments the body tissue is a myocardial body tissue.

According to still further features in the described preferred embodiments the body tissue is a muscle tissue.

According to still further features in the described preferred embodiments the device includes a syringe.

According to still further features in the described preferred embodiments the syringe is equipped with a 18-27 gauge bore needle.

According to still further features in the described preferred embodiments the device includes a catheter.

According to still further features in the described preferred embodiments the catheter is suitable for intra-arterial administration of the therapeutic composition.

According to still further features in the described preferred embodiments the catheter is suitable for intra-coronary administration of the therapeutic composition.

According to still further features in the described preferred embodiments the catheter suitable for intra-coronary administration is an over-the-wire balloon catheter.

According to still further features in the described preferred embodiments the polymer salt is a polysaccharide salt.

According to still further features in the described preferred embodiments the polysaccharide salt is an alginate salt.

According to still further features in the described preferred embodiments the polymer salt is sodium alginate.

According to still further features in the described preferred embodiments the multivalent cation salt is a calcium salt.

According to still further features in the described preferred embodiments the calcium salt is calcium gluconate.

According to still further features in the described preferred embodiments the predetermined multivalent cation salt to polymer salt ratio ranges between 2:1 and 1:10.

According to still further features in the described preferred embodiments the predetermined multivalent cation salt to polymer salt ratio ranges between 1:1 and 1:6.

According to still further features in the described preferred embodiments the predetermined multivalent cation salt to polymer salt ratio ranges between 1:2 and 1:5.

According to still further features in the described preferred embodiments the predetermined multivalent cation salt to polymer salt ratio ranges between 1:3 and 1:4.

According to still further features in the described preferred embodiments the mixing is effected by using a homogenizer.

According to still further features in the described preferred embodiments the homogenizer is operated at a speed setting ranging from 2,000 to 50,000 rpm.

According to still further features in the described preferred embodiments the homogenizer is operated at a speed setting ranging from 5,000 to 40,000 rpm.

According to still further features in the described preferred embodiments the mixing is effected at a speed setting ranging from 10,000 to 30,000 rpm.

According to still further features in the described preferred embodiments the mixing is effected over a period of at least 30 seconds.

According to still further features in the described preferred embodiments the mixing is effected over a period of at least 1 minute.

According to still further features in the described preferred embodiments the mixing is effected over a period of at least 2 minutes.

According to still further features in the described preferred embodiments the damaged body tissue is a damaged myocardial tissue.

According to still further features in the described preferred embodiments the myocardial tissue is the left ventricular wall tissue.

According to still further features in the described preferred embodiments the damaged body tissue is a damaged muscle tissue.

According to still further features in the described preferred embodiments the step of providing is effected via a needle.

According to still further features in the described preferred embodiments the step of providing is effected intra-arterially via a suitable catheter.

According to still further features in the described preferred embodiments the step of providing is effected intra-coronarily via a suitable catheter.

According to still further features in the described preferred embodiments the suitable catheter is an over-the-wire balloon catheter.

According to still further features in the described preferred embodiments the effective amount ranges between about 0.1 and 10 ml.

According to still further features in the described preferred embodiments the effective amount ranges between about 0.5 and 5 ml.

According to still further features in the described preferred embodiments the effective amount ranges between 1 and 4 ml.

According to still further features in the described preferred embodiments the heart condition is a congestive heart failure or an ischemic mitral regurgitation.

The present invention successfully addresses the shortcomings of the presently known configurations by providing a therapeutically beneficial cross-linked polymer solution which can be administered into a damaged body tissue via injection or catheterization, thereby providing substantial therapeutic benefits to the damaged body tissue safely and effectively.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 5A-B show the LV diastolic dimension M-mode in treated and untreated animals, respectively. FIGS. 5C-D shows the LV systolic dimension in treated and untreated animals, respectively. FIGS. 5E-F shows the LV diastolic area in treated and untreated animals, respectively. FIGS. 5G-H shows LV systolic area in treated and untreated animals, respectively. Abbreviations: B., baseline; 2 mo., two months;

FIGS. 6A-B shows the AW 2-D in treated and untreated animals, respectively. FIGS. 6C-D show the LV diastolic dimension 2-D in treated and untreated animals, respectively. FIGS. 6E-F show the LV systolic dimension 2-D in treated and untreated animals, respectively. Abbreviations: B., baseline; 2 mo., two months;

FIGS. 7A-B show LV fractional shortening in treated and untreated animals, respectively. FIGS. 7C-D show the LV fractional area change in treated and untreated animals, respectively. Abbreviations: B., baseline; 2 mo., two months;

FIG. 9A is a schematic illustration of ischemic MR with mitral annulus dilatation. FIG. 9B is a schematic illustration of ischemic MR with change in the global geometry of the left ventricle and tethering of the mitral leaflet.

DESCRIPTION OF THE PREFERRED EMBODIMENTS

Figure 1A:
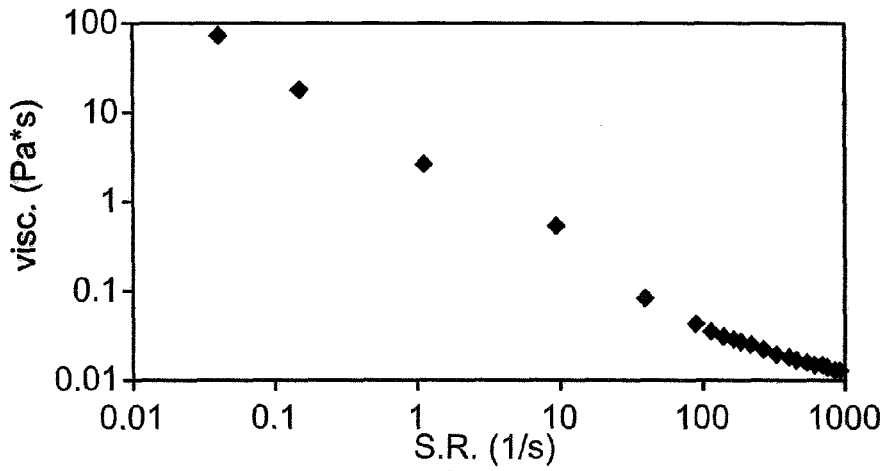
FIG. 1A illustrates the effect of shear rate on viscosity of an aqueous solution of 1% (w/v) sodium alginate (LF 5/60; viscosity=40 cP) mixed with 0.3% (w/v) calcium gluconate concentration. Abbreviations: visc., viscosity; S.R., Shear Rate.

The present invention is of a cross-linked polymer solution which can be used to treat a body tissue, such as a damaged myocardial tissue.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

International patent application WO 99/15211 teaches an injectable, partially hardened hydrogel. This composition is viscous suspension/paste capable of holding its shape against gravity. The reference does not describe or suggest a cross-linked polymer solution which is flowable and capable of stably maintaining a liquid state in storage.

U.S. Pat. No. 6,136,334 teaches an aqueous mixture comprising an ionic polysaccharide capable of being gelled in situ upon contact with a counter ion. The reference does not describe or suggest a solution which includes a cross-linked polymer.

U.S. Pat. No. 5,709,854 teaches an injectable suspension of polysaccharide hydrogel mixed with living cells. The reference does not describe or suggest a cross-linked polymer solution which is flowable and capable of stably maintaining a liquid state in storage.

U.S. Pat. No. 6,592,886 teaches a cross-linked alginate gel matrix, such as beads, for use in encapsulating transplant materials. The reference does not describe or suggest a cross-linked polymer solution which is flowable and capable of stably maintaining a liquid state in storage.

While reducing the present invention to practice the present inventors surprisingly and unexpectedly uncovered that alginate polysaccharide can be uniformly cross-linked to form a stable aqueous solution which is also substantially viscoelastic. As a stable solution, the novel composition can be readily administered into a body tissue via a needle or a catheter. Most surprisingly, administering the solution of the present invention into animals' hearts, following myocardium infarct, resulted in remarkable improvement of heart function and regeneration of damaged myocardium tissue (see Examples 1-6 and 8 in the Examples section which follows).

Thus, according to one aspect of the present invention, there is provided a therapeutic composition for treatment of a body tissue. The composition includes an aqueous solution of a cross-linked polymer being capable of (i) maintaining a liquid state in storage at room temperature for at least 24 hours and (ii) assuming a gel state following deposition within the body tissue.

As used herein, the term "solution" refers to a liquid in which two or more substances (e.g. solute and solvent) are mixed together and uniformly dispersed. The phrase "aqueous solution" refers to a liquid in which one or more substances (solutes) are uniformly dispersed in water (solvent).

The terms "liquid" and "flowable" are used interchangeably herein and refer to the capacity of a substance to flow freely and assume the shape of the space containing it.

As used herein, the phrase "cross-linked polymer" refers to a network of polymer units being inter-linked via covalent, hydrogen or ionic bonding.

A suitable polymer, according to the teaching of the present invention, can be any biocompatible, non-immunogenic and, preferably, bio-erodible polymer which can be cross-linked to form a hydrogel.

As used herein, the term "gel" refers to a semisolid colloidal suspension of a solid in a liquid. The term "hydrogel" refers to a gel which contains water as the liquid.

Preferably, the polymer of the present invention is a polysaccharide, most preferably an alginate.

The term "alginate" refers to a polyanionic polysaccharide copolymer derived from sea algae (e.g., *Laminaria hyper-* borea, *L. digitata, Eclonia maxima, Macrocystis pyrifera, Lessonia nigrescens, Ascophyllum codosum, L. japonica, Durvillaea antarctica,* and *D. potatorum*) and which includes β-D-mannuronic (M) and α-L-guluronic acid (G) residues in varying proportions.

An alginate suitable for use in the present invention has a monomer ratio between α-L-guluronic acid and β-D-mannuronic preferably ranging between 1:1 to 3:1, more preferably between 1.5:1 and 2.5:1, most preferably about 2.

An alginate suitable for use in the present invention has a molecular weight ranging preferably between 1 to 300 kDa, more preferably between 5 to 200 kDa, more preferably between 10 to 100 kDa, most preferably between 20 to 50 kDa.

Cross linking of the polymer of the present invention can be effected via multivalent cations such as, but not limited to, calcium, strontium, barium, magnesium or aluminum, as well as di-, tri- and tetrafunctional organic cations. In addition, polyions can be used such as, for example, poly(amino acids), poly(ethyleneimine), poly(vinylamine), poly(allylamine) and cationic polysaccharides. Most preferably, the cross linking is effected via calcium cations.

The multivalent cation salt is preferably a pharmacologically acceptable calcium salt such as, for example, calcium gluconate, calcium citrate, calcium acetate, calcium fluoride, calcium phosphate, calcium tartrate, calcium sulfate, calcium borate or calcium chloride. Most preferably, the multivalent cation salt is calcium D-gluconate (calcium gluconate). Pharmaceutical grade calcium gluconate salts are readily available from several commercial manufacturers such as, for example, Sigma.

The polymer salt is preferably a pharmacologically acceptable alginate salt such sodium, potassium, lithium, rubidium and cesium salts of alginic acid, as well as the ammonium salt, and the soluble alginates of an organic base such as mono-, di-, or tri-ethanolamine alginates, aniline alginates, and the like. Most preferably, the polymer salt is sodium alginate. Pharmaceutical grade sodium alginate salts, which comply with all the quality and safety requirements of the European and United States of America (USA) pharmacological regulatory authorities, are readily available from several commercial manufacturers such as, for example, Novamatrix FMC Biopolymers (Drammen, Norway).

An aqueous solution containing calcium gluconate and sodium alginate at a predetermined ratio can be prepared by combining a sodium alginate stock solution with a calcium gluconate stock solution.

The weight ratio between calcium gluconate and sodium alginate in the aqueous solution preferably ranges between 2:1 and 1:10, more preferably between 1:1 and 1:6, more preferably between 1:2 and 1:5, most preferably between 1:3 and 1:4.

The aqueous cross-linked polymer solution of the invention can be obtained by uniformly cross linking the alginate particles via the calcium cations being present in the aqueous solution. The cross linking can be effected by (i) providing an aqueous solution containing a predetermined multivalent cation salt to polymer salt ratio and (ii) mixing the aqueous solution under conditions suitable for uniformly cross linking the polymer with the multivalent cation and yet maintaining the aqueous solution as an aqueous cross-linked polymer solution.

The phrase "uniformly cross linking" used herein refers to spreading the bonds linking the polymer chains in a substantially non-clustered distribution, preferably random distribution, most preferably even distribution. The uniformly crossed-linked solution assumes substantial viscoelasticity yet retains its liquidity and flowability.

Uniform cross linking can be effected by using a device (e.g. homogenizer) to capable of rigorously mixing the solution without substantially shearing the cross-linked polymer. A suitable homogenizer can be, for example, Heildolph DIAX 900 equipped with 10G dispenser head. The homogenizer is operated at a working speed preferably ranging between 5,000 and 50,000 rpm, more preferably between 10,000 and 30,000 rpm. Homogenization is conducted preferably for at least 30 seconds, more preferably at least 2 minutes, most preferably at least 5 minutes.

The therapeutic composition is can be prepared using the following procedure (see Example 1 hereinbelow for further details): (i) a predetermined amount of sodium alginate is mixed with a predetermined volume of distilled water; (ii) the mixture resulting from step (i) is stirred until a clear solution is obtained; (iii) the solution resulting from step (ii) is filter sterilized (e.g., using a 0.2 μm pore membrane); (iv) a predetermined amount of calcium D-Gluconate (hemicalcium salt) is mixed with a predetermined volume of distilled water; (v) the mixture resulting from step (iv) is stirred until a clear solution is obtained; (vi) the solution resulting from step (v) is filter sterilized; (vii) the solution of step (iii) is combined the solution of step (vi) and mixed using a suitable homogenizer to make the therapeutic composition. Once prepared, the composition is stored at 4-8° C. until use.

The final concentration (w/v) of alginate in the composition preferably ranges between 0.1 to 4%, more preferably between 0.5 and 2%, most preferably between 0.8 and 1.5%. The final concentration (w/v) of calcium cations in the composition of the present invention preferably ranges between 0.005 and 0.1%, more preferably between 0.01 and 0.05%, more preferably between 0.02 and 0.04%, most preferably between 0.025 and 0.035%.

The therapeutic composition of the present invention preferably exhibits an elastic response which is equal to or greater than its viscous response under small deformation oscillatory frequencies in the linear viscoelastic limit and a shear thinning behavior in a power-law relationship.

The term "viscosity (η)" used herein refers to a measure of the resistance of a fluid to flow. It is defined as the ratio of shear stress (τ) to shear rate (γ):

$$\eta = \tau/\gamma$$

When the fluid obeys the equation for all shear rates, it is denoted Newtonian [Ferry, J. D. (Ed.), Viscoelastic Properties of Polymers", John Wiley & Sons, 1980].

The viscoelastic properties of the composition can be determined by applying a sinusoidal stress or strain of frequency f to the sample and measuring the response. The response is divided into (i) an elastic part in phase with the applied stress or strain, and (ii) a viscous part out of phase. Because of the two components, a complex notation is used. The complex shear modulus is denoted by G*, which is defined by the following formula:

$$G^* = G' + jG''$$

wherein G' is the storage modulus, i.e., the elastic part, G" is the loss modulus (the viscous part), and $j^2 = -1$.

The shear modulus as a function of frequency can be expressed by the slope n in a log-log plot of G' versus frequency, f, denoted by the following formula:

$$\log G' = n \log f + K$$

wherein K is a constant. In a physical gel n>0, in a covalent gel n=0.

Viscoelastic features can be presented in terms of the storage modulus G' (herein referred to as the "elastic response") and the loss modulus G" (herein referred to as the "viscous response") as a function of angular frequency.

The values of elastic response (G'), viscous response (G') and viscosity (η) can be determined using standard rheological methods [see, for example, Ronald G Larson, "The Structure and Rheology of Complex Fluids", Oxford University Press, Inc., 663 pp, 1998; and Christopher W. Macosko, "Rheology: Principles, Measurements, and Applications", Wiley-VCH Inc., 568 pp., 1994].

Rheological measurements are preferably obtained under an oscillatory frequency ranging within the viscoelastic limit, preferably ranging between 0.01 and 100 Hz, more preferably ranging between 0.1 to 10 Hz.

As illustrated in Examples 1 hereinbelow, preferred compositions of the present invention do not have permanent cross links, are strongly frequency dependent and have G'-G" crossover. These features are indicative of "entanglement network" materials (Clark A. and S. B. Ross-Murphy, "Structural and Mechanical Properties of Biopolymer Gels. Adv. Poly. Sci. Springer-Verlag, Berlin, Heidelberg, 1987).

As stated hereinabove, the therapeutic composition of the invention is capable of maintaining a liquid state in storage at room temperature (e.g., at about 24-25° C.) for at least 24 hr. Preferably, the composition is capable of maintaining a liquid state at room temperature for at least 48 hr, more preferably for at least seven days. When refrigerated (e.g., at about 4-8° C.) the composition of the invention is preferably capable of maintaining a liquid state for a period of at least one month. Accordingly, the composition of the invention includes a network of a viscoelastic material which is stably maintained in a solution state.

As a solution, the composition can be administered into a body tissue via a surgical needle such as a 18-27 gauge bore needle, as further described in details in Examples 2-5 and 7-8 hereinbelow.

Surprisingly and unexpectedly, the present inventors uncovered that the composition of the invention can be delivered into a damaged myocardium via intra-coronary administration (see Example 6 hereinbelow). These findings indicate that the composition is uniquely capable of flowing within a blood vessel, crossing out of blood capillaries and spreading into the extracellular matrix of the surrounding tissue.

As used herein, the phrase "blood vessel" refers to an artery, a vein or a capillary.

Following deposition within a body tissue, the composition of the invention assumes a gel state. The transition from a liquid to gel state results from the diffusion of water from the viscoelastic matrix into the surrounding extracellular medium. Once gelatinized, the viscoelastic material provides substantial mechanical support and elasticity to the body tissue, as well as scaffolding for new tissue regeneration. Hence, the capacity of the cross-linked polymer solution to assume a gel state, following deposition in the target body tissue, is an essential feature of the present invention.

Optionally, the therapeutic composition of the invention further includes cells and/or at least one therapeutic agent.

Suitable cells which may be included in the composition of the present invention can be, for example, cardiomycetes, myoblasts, fibroblasts, chondrocytes, muscle cells, smooth muscle cells, endothelial cells, mesenchymal cells and embryonic stem cells. The cells can be mixed with the cross-linked polymer described hereinabove to make the therapeutic composition of the present invention.

Suitable therapeutic agents which may be included in the composition of the present invention can be, for example, growth factors (e.g., basic fibroblast growth factor; bFGF), vascular endothelial growth factor (VEGF), insulin-like growth factor (IGF), members of the TGF-family, bone morphogenic proteins (BMP), platelet-derived growth factors, angiopoietins, and other factors such as myogenic factors, transcription factors, cytokines, and homeobox gene products, polynucleotides, polypeptides, hormones, anti-inflammatory drugs, anti-apoptotic drugs or antibiotic drugs.

Optionally, the therapeutic agent or agents can be chemically linked to the polymer of the invention. Such linkage can be effected via any known chemical bonding approach, preferably a covalent bond. A suitable covalent bond can be, for example, an ester bond (e.g., a carboxylic ester bond, an oxyalkyl carboxylic ester bond, an amide bond, or a thioester bond), a glycosidic bond, a carbonate bond, a carbamate bond, a thiocarbamate bond, a urea bond or a thiourea bond.

Therapeutic compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the therapeutic compositions or human or veterinary administration. Such notice, for example, may be of labeling approved by the U.S. Food and Drug Administration for medical devices or drugs, or of an approved product insert. Therapeutic compositions may also be prepared, placed in an appropriate container, and labeled for treatment of an indicated condition, as if further detailed above.

Optionally, the therapeutic composition of the invention may be packaged in a kit, along with a devise suitable for administering the therapeutic composition into a body tissue and with a packaging material identifying the kit for use in treatment of the body tissue.

As mentioned hereinabove, the present inventors unexpectedly uncovered that providing cross-linked alginate solution into infarcted myocardium tissues of rats and pigs, via injection or intra-coronary administration, substantially improved the heart function, induced angiogenesis and promoted regeneration of the damaged tissue (see details in Examples 2-6 and 8 hereinbelow). In addition, the cross-linked alginate solution was shown capable of substantially improving blood flow in ischemic limb tissues of rats (Example 7).

Thus, according to another aspect of the present invention there is provided a method of treating a body tissue, such as a damaged body tissue, by providing the body tissue with an effective amount of the therapeutic composition of the present invention.

The term "treatment" used herein encompasses the complete range of therapeutically positive effects of administrating the composition of the present invention to a body tissue, including improving the tissue function, providing mechanical support and promoting tissue healing and repair processes (e.g., angiogenesis and new tissue regeneration). The term treatment further includes reduction of, alleviation of, and relief of diseases or disorders associated with a damaged tissue. In addition, the term treatment includes prevention or postponement of development of diseases or disorders associated with a damaged tissue.

The phrase "body tissue" used herein encompasses any mammalian body tissue, preferably a human body tissue. A body tissue, according to the teachings to the present invention, can be, but not limited to, a myocardial tissue, a muscle tissue, a kidney tissue, a cartilage tissue, a bone tissue, or a dermal tissue.

The phrase "damaged body tissue" used herein encompasses any body tissue which is functionally and/or structurally impaired, such as, but not limited to, an infarcted (post MI) myocardium, an ischemic myocardium, an ischemic muscle, an ischemic cartilage, an ischemic bone or an ischemic dermis.

The term "angiogenesis" used herein refers to the process of vascularization of a tissue involving the development of new capillary blood vessels.

As mentioned hereinabove, the therapeutic composition of the present invention can be injected directly into a damaged body tissue or be administered intravenously.

Advantageously, the therapeutic composition of the present invention can be administered intra-arterially, preferably intra-coronarily, via a catheter such as described, for example, by Knight et al. (Circulation 95:2075-2081, 1997). Most preferably, the composition is administered intra-coronarily via an over-the-wire balloon catheter such as described, for example, in Examples 6 hereinbelow.

The phrase "effective amount" used herein refers to an amount effective to provide a significant therapeutic benefit. The amount of a composition to be administered will, of course, be dependent on the subject being treated, the severity of the affliction, the manner of administration, the judgment of the prescribing physician, etc. Preferably, an effective amount ranges between 0.1 and 10 ml (dwt between 1 and 10 mg), more preferably between 0.5 and 5 ml (dwt between 5 and 50 mg), most preferably between 1 and 4 ml (dwt between 10 and 40 mg).

The composition of the present invention can also be used to effectively treat chronic heart conditions such as, for example, congestive heart failure (CHF) and ischemic mitral regurgitation (MR), by providing the heart tissue with an effective amount of the therapeutic composition.

The composition of the present invention can be used to induce angiogenesis in a damaged heart tissue, by providing the damaged heart tissue with an effective amount of the therapeutic composition.

In addition, the composition of the present invention can be used to induce angiogenesis and promote blood flow in an ischemic muscle tissue, such as an ischemic limb muscle tissue, by providing the damaged muscle tissue with an effective amount of the therapeutic composition.

Hence, the present invention provides a novel aqueous cross-linked polymer solution which can be delivered into a body tissue via injection or intra-arterial administration, so as to provide substantial therapeutic benefits to the treated body tissue effectively and safely.

Although the detailed descriptions above relate primarily to alginate solutions, it should be noted that that the teachings of the present invention can be applied to solutions of other biocompatible polymers (e.g., chitosan, gellan gum, carageenan, polyphosphazines, polyacrylates), since parameters governing preparation of the cross-linked alginate solutions described above (e.g., exhibiting an elastic response which is equal to or greater than its viscous response under small deformation oscillatory frequencies in the linear viscoelastic limit and a shear thinning behavior in a power-law relationship) can be used as guidelines for preparing other types of cross-linked polymer solutions capable of maintaining a liquid state in storage at room temperature and assuming a gel state following deposition within the body tissue.

As used herein, the term "about" denotes ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Preparation and Rheological Evaluation of Cross-Linked Alginate Solutions

Materials and Methods:

Preparation of Sodium Alginate and Calcium Gluconate Mixtures

Sodium alginate samples (Mw ranging from about 15 to 160 kDa; G/M ratio 2.1) were purchased from FMC Biopolymers, Drammen, Norway. Sodium alginate samples were dissolved in double distilled water (DDW) to a final concentration of 2% (w/v) then mixed with 2% (w/v) calcium gluconate solution (D-gluconic acid, hemi-calcium salt, Sigma). The mixtures were homogenized using Fleidolph DIAX 900 homogenizer equipped with 10G head, operating at 26,000 rpm for about 2 minutes. Following homogenization, the preparations were refrigerated at about 4-8° C. until use.

Alginate Molecular Weight Determination

Sodium alginate samples were separated on a chromatographic system comprising a Waters 606 pump followed by two PSS Suprema gel permeation columns connected in a series. Column dimensions were 300×8 $mm^2$, particle size 10 mm, porosity of 3000 and 10,000 A. Flow rate was 0.5 ml/min. The columns were kept at a constant temperature of 25° C. inside a Techlab K-4 controlled oven. The chromatographic system was attached to a Dawn DSP (Wyatt Technology Corporation) multi-angle laser light scattering (MALLS) photometer equipped with a He/Ne laser working at 632.8 nm, a K5 refraction cell and 18 detectors at angles 14-1630. Concentration was monitored by a calibrated interferometric refractometer Optilab DSP (Wyatt Technology Corporation). Data processing and molar mass calculation were performed with Wyatt ASTRA software version 4.7. Each sample was injected three times to ensure reproducibility. The alginate dn/dc was estimated (using Optilab DSP, controlled by Wyatt dn/dc software) to be 0.155 ml/g (aqueous buffer). Aqueous buffer solutions were prepared from ultra pure water (0.055 μs/cm; USF SERAL Purelab R075 followed by USF SERAL Purelab UV) supplemented with 0.1 M $NaNO_3$, 0.02% (w/v)

NaN$_3$ and 10 mM imidazole. The buffer was titrated with NaNO$_3$ to pH 7.0 and filtered through a 0.1 μm filter (Gelman Sciences VacuCap 60).

Rheological Analysis

Rheological analyses were made using a CarriMed CLS50 controlled stress rheometer (CarriMed Instruments Ltd. Dorking, UK) operated in the cone-plate mode (cone angle 1° and 4°, having 60 and 40 mm diameter, respectively). Small amplitude oscillatory shear experiments (0.1-10 Hz) were performed within the linear viscoelastic limit. Frequency scans were performed at the lowest stress possible to prevent damage to the sample. The linearity of the response was monitored continuously to ascertain linear viscoelasticity.

Results:

The molecular weight (Mw) and polydispersity (PD; a measure of Mw distribution range) values of selected sodium alginate samples, as determined by GPC-MALLS analysis, are shown in Table 1 bellow.

TABLE 1

Molecular characteristics of different alginates

| Alginate type | Mn (g/mol) | Mw (g/mol) | Polydispersity (Mw/Mn) | Approximate Average Mw (kDa) |
|---|---|---|---|---|
| LF 5/60* | 1.348e+4 | 1.68e+4 | 1.246 ± 0.001 | 15 |
| | 1.353e+4 | 1.639e+4 | 1.212 ± 0.002 | |
| LF 5/60 | 2.102e+4 | 2.752e+4 | 1.309 ± 0.007 | 30 |
| | 2.113e+4 | 2.656e+4 | 1.257 ± 0.01 | |
| LVG | 8.986e+4 | 1.029e+5 | 1.145 + 0.006 | 100 |
| | 9.038e+4 | 9.877e+4 | 1.093 + 0.002 | |
| LVG | 1.469e+5 | 1.667e+5 | 1.135 ± 0.016 | 160 |
| | 1.385e+5 | 1.559e+5 | 1.126 ± 0.012 | |
| MVG | 2.103e+5 | 2.596e+5 | 1.235 ± 0.006 | 250 |
| | 2.055e+5 | 2.385e+5 | 1.161 ± 0.007 | |

*alginate was subjected to a controlled degradation.

Plots of viscosity vs. shear rate of sodium alginate solutions exhibited essentially constant viscosity for all shear rates. The average measured viscosity values of the sodium alginate solutions are shown in Table 2 below.

TABLE 2

Viscosity as a function of shear rate ($10^{-2}$-$10^{-4}$/sec)

| Alginate Solution | Viscosity (cP) |
|---|---|
| 1% (w/v) LF 5/60 | 40 |
| 1% (w/v) LVG | 127 |
| 1% (w/v) MVG | 400 |

Figure 1B:
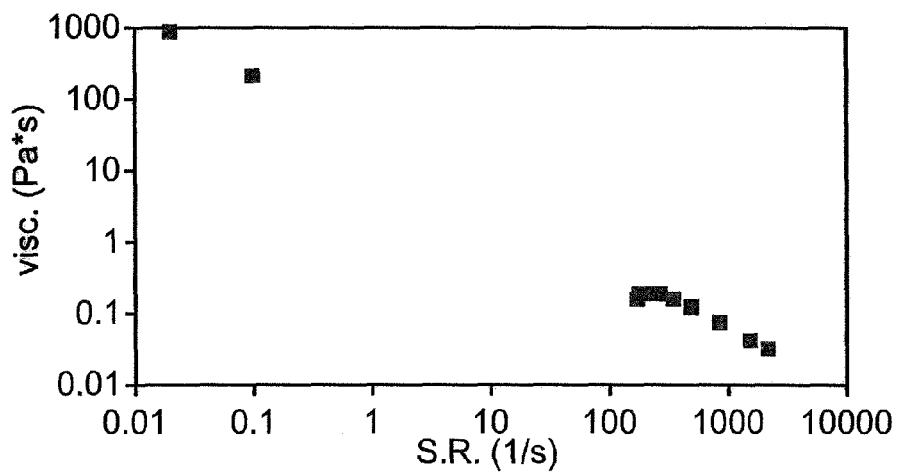
FIG. 1B illustrates the effect of shear rate on viscosity of an aqueous solution of 1% (w/v) sodium alginate (LF 5/60; viscosity=40 cP) mixed with 0.4% (w/v) calcium gluconate concentration. Abbreviations: visc., viscosity; S.R., Shear Rate.
Figure 2:
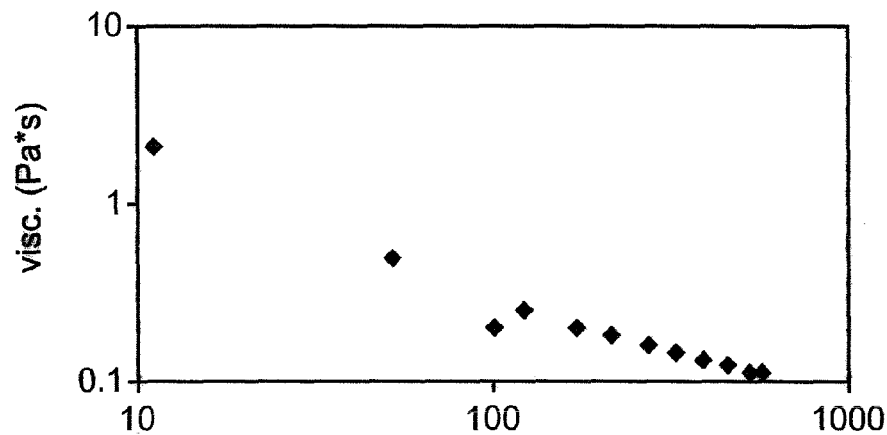
FIG. 2 illustrates the effect of shear rate on viscosity of an aqueous solution of 1% (w/v) sodium alginate (LVG; viscosity=127 cP) mixed with 0.3% (w/v) calcium gluconate concentration. Abbreviations: visc., viscosity; S.R., Shear Rate.
Figure 3A:
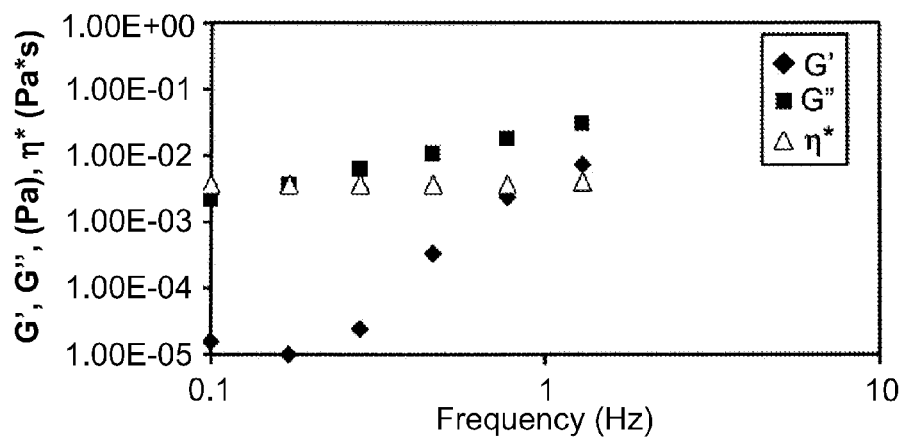
FIGS. 3A-C illustrate mechanical spectra of aqueous solutions of 1% alginate (LF 5/60; viscosity=40 cP) with no calcium gluconate added (FIG. 3A), mixed with 0.3% (w/N) calcium gluconate (FIG. 3B), or mixed with 0.4% (w/v) calcium gluconate (FIG. 3C). Abbreviations: Freq., frequency.
Figure 3B:
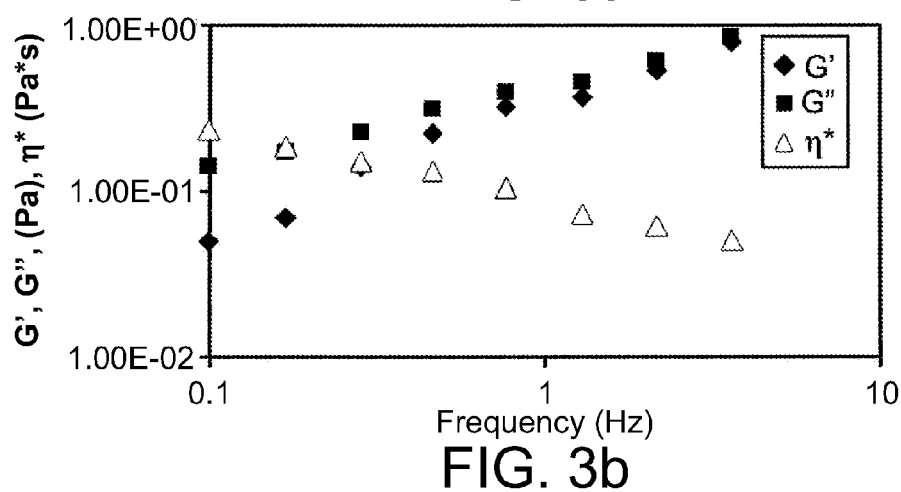
Figure 3C:
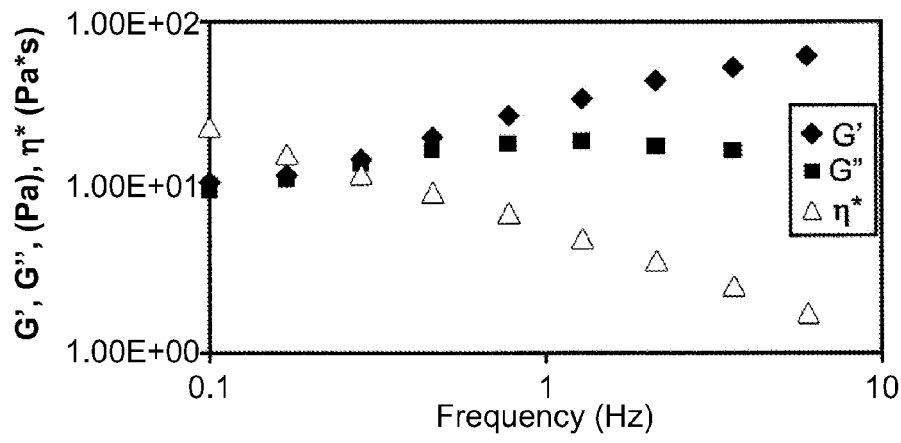
Figure 4A:
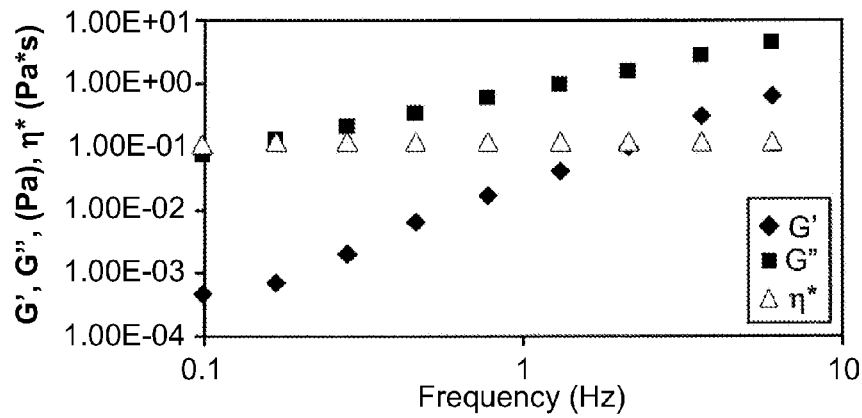
FIGS. 4A-B illustrate mechanical spectra of an aqueous solution of 1% (w/v) alginate (LVG; viscosity=127 cP) with no calcium gluconate added (FIG. 4A), or mixed with 0.3% (w/v) calcium gluconate (FIG. 4B). Abbreviations: Freq., frequency.
Figure 4B:
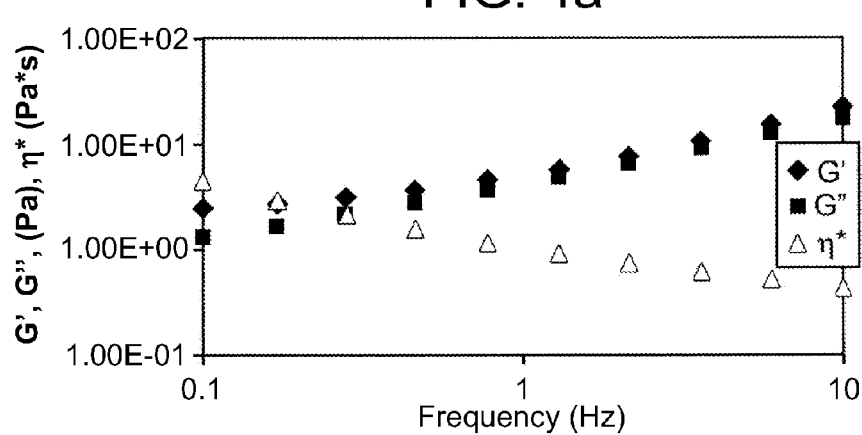
Figure 5A:
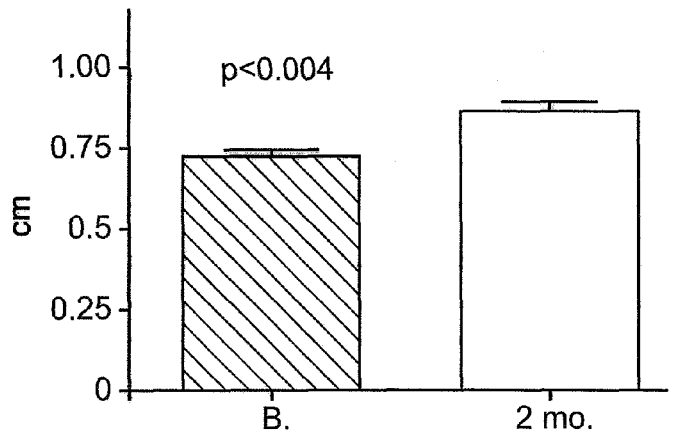
FIGS. 5A-H shows echocardiography results illustrating the effect of the aqueous cross-linked alginate solution on the Left Ventricular (LV) remodeling.
Figure 5B:
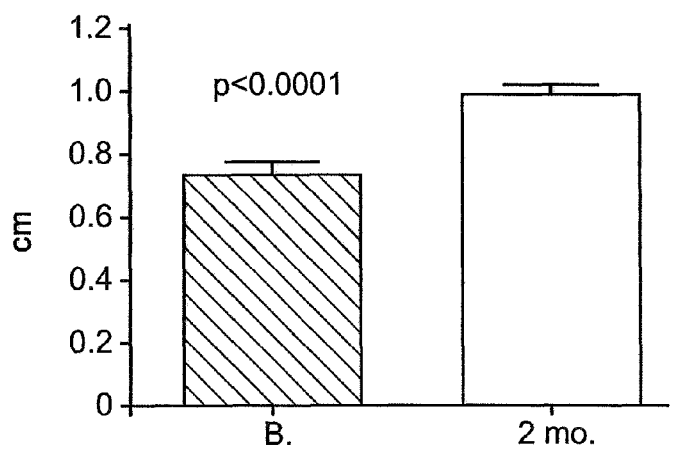
Figure 5C:
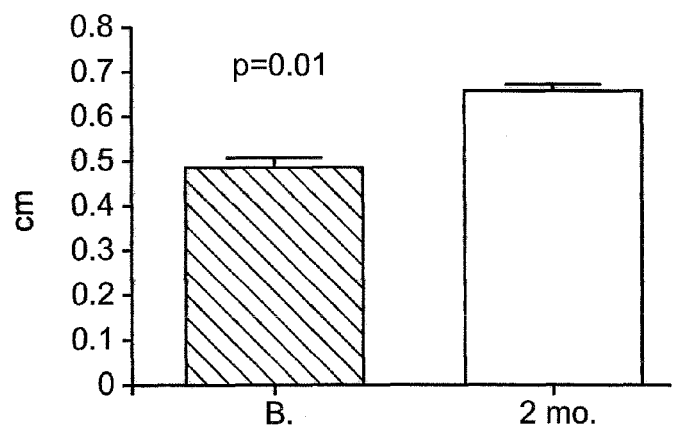
Figure 5D:
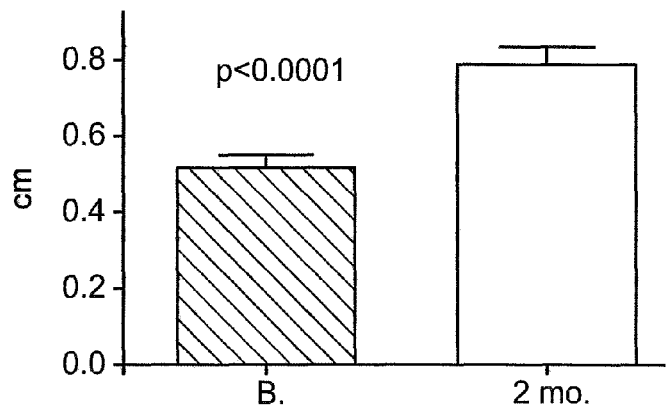
Figure 5E:
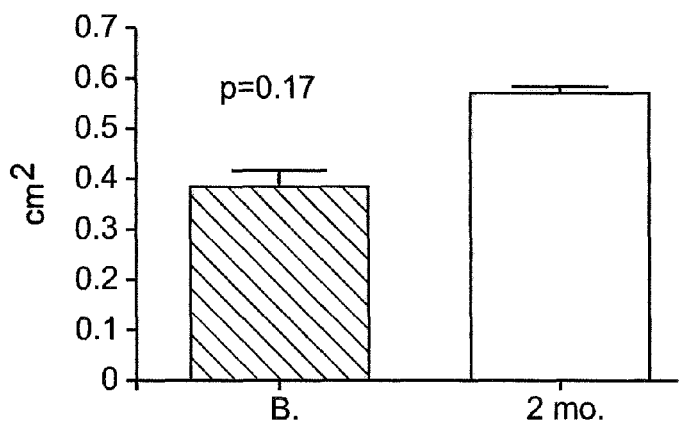
Figure 5F:
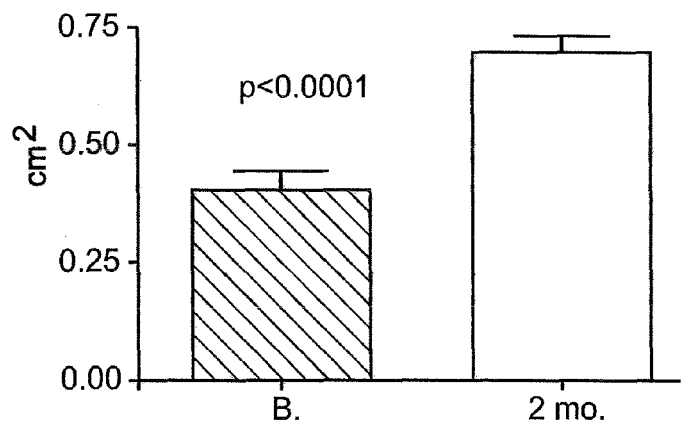
Figure 5G:
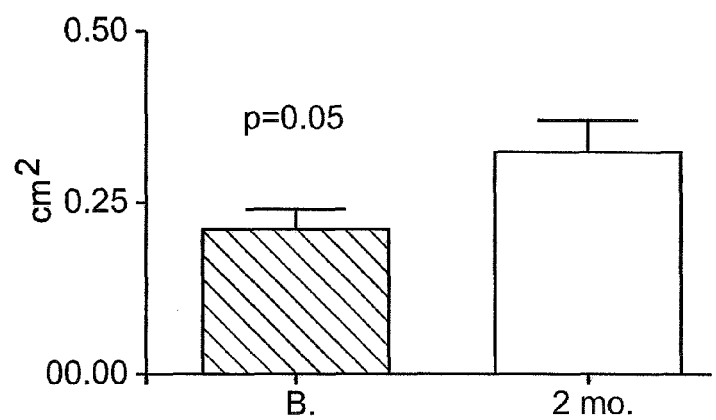
Figure 5H:
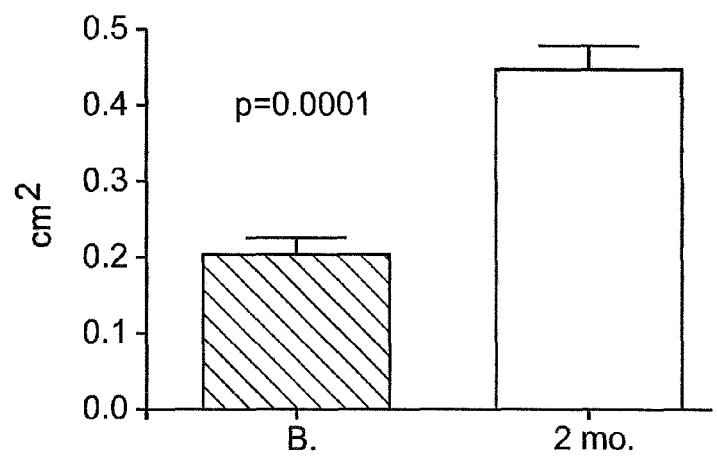
Figure 6A:
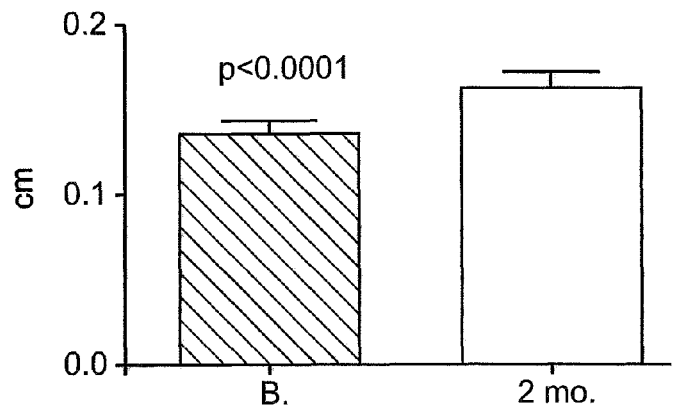
FIGS. 6A-F shows 2-D echocardiography results illustrating the effect of the aqueous cross-linked alginate solution on the Left Ventricular (LV) remodeling.
Figure 6B:
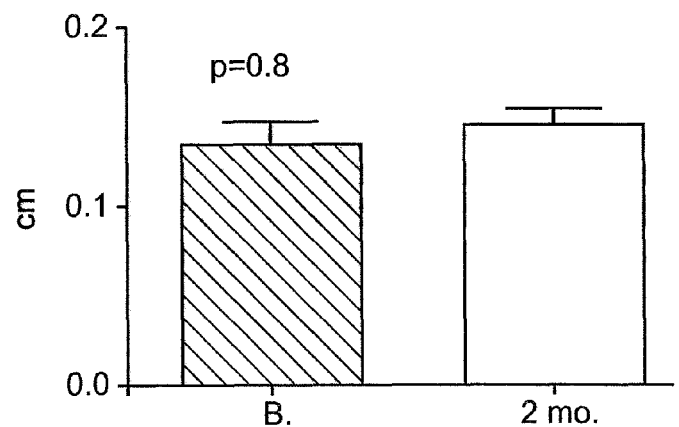
Figure 6C:
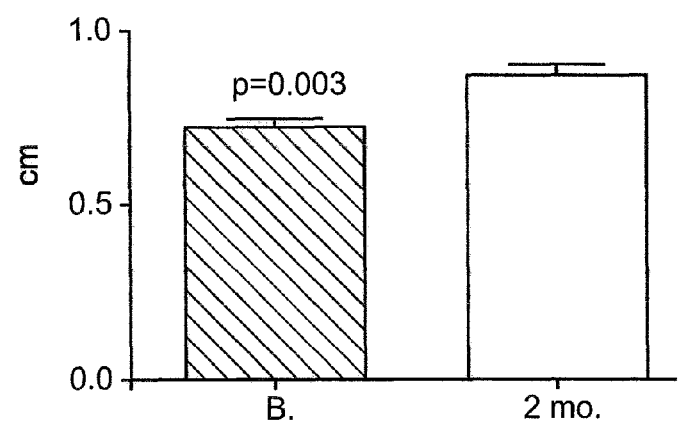
Figure 6D:
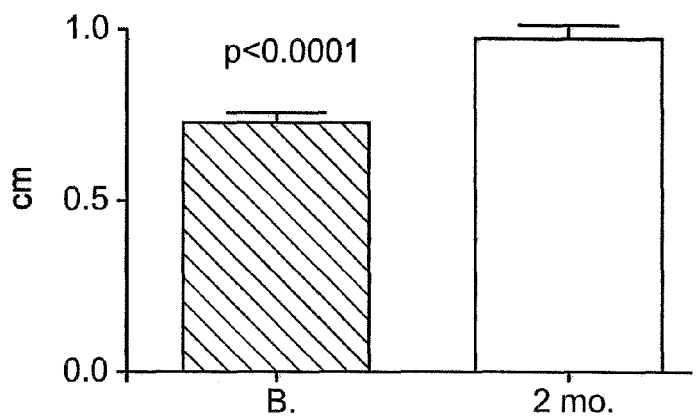
Figure 6E:
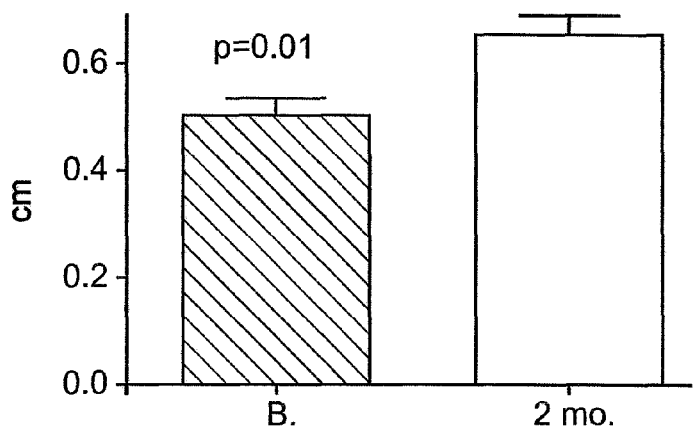
Figure 6F:
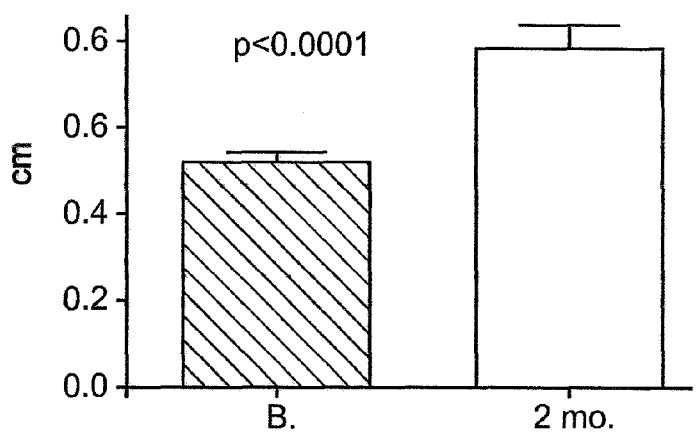
Figure 7A:
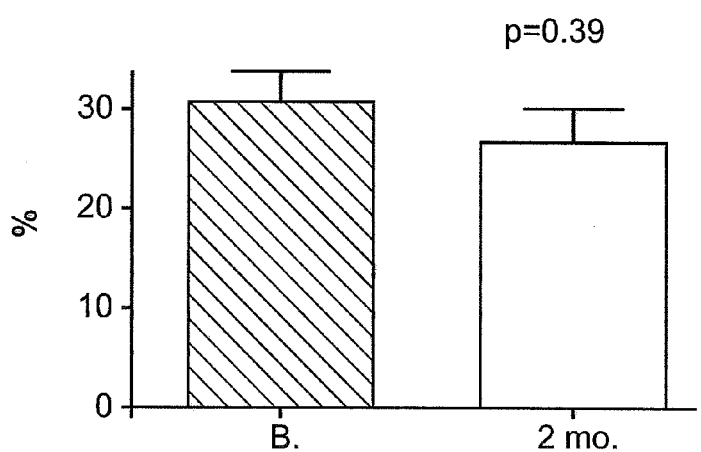
FIGS. 7A-D shows echocardiography results illustrating the effect of the aqueous cross-linked alginate solution on the Left Ventricular (LV) function.
Figure 7B:
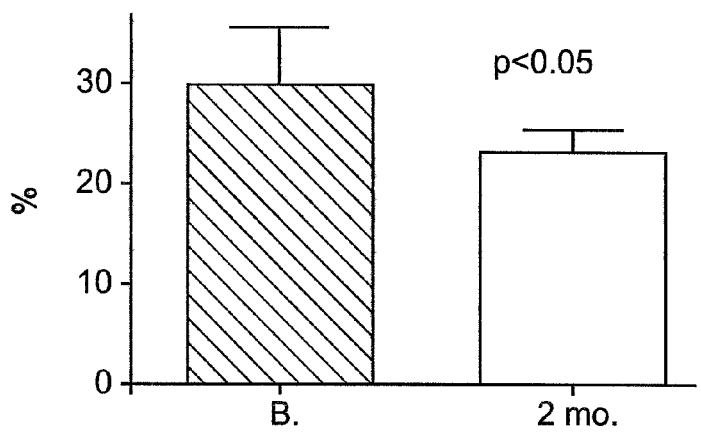
Figure 7C:
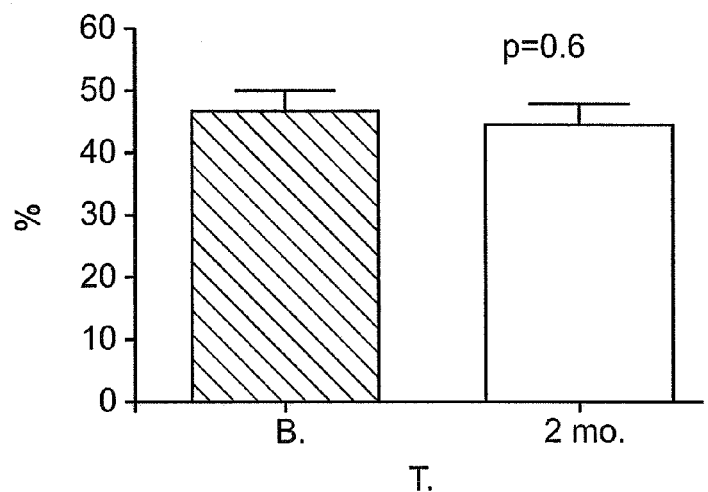
Figure 7D:
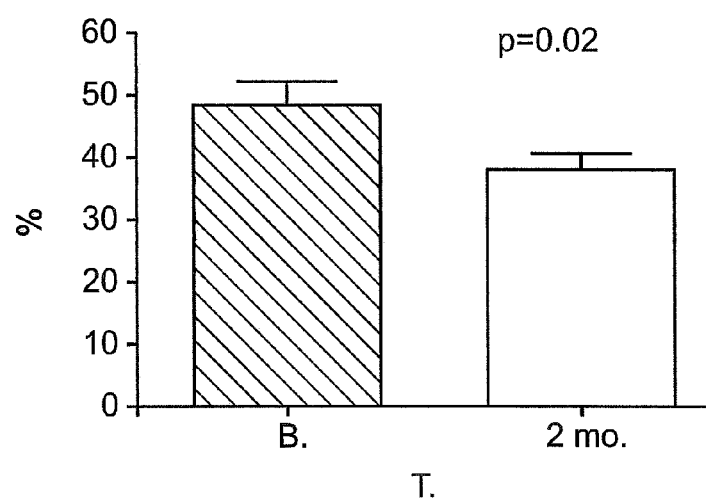

As can be seen in FIGS. 1A-B and 2, providing sodium alginate solutions with calcium ions resulted in decreasing of the solutions viscosity by increasing shear rates. Such behavior, also known as a shear thinning (or pseudoelastic) behavior in a power-law relationship, is indicative of a structured material (Lapasin and Pricl, "Rheology of Industrial Polysaccharides: Theory and Application, London, Blackbie, 620 pp, 1995).

Viscoelastic spectra of various preparations (exhibiting changes of viscosity, elastic response and viscous response values under increasing oscillatory frequencies) are shown in FIGS. 3-4 and 15-34.

As can be seen in FIGS. 3A, 4A, 10, 18, 21, 24, 28 and 30 and in Table 3 hereinbelow, sodium alginate solutions devoid of calcium ions exhibited viscous response (G") greater than the elastic response (G') under oscillatory frequencies in the linear viscoelastic limit (0.1-10 Hz). Such material behavior is indicative of a random coil polymer solution (i.e., having no polymer cross-linking).

As can be seen in FIGS. 11-14, 19, 22, 26, 29 and 31 and in Table 3 hereinbelow, sodium alginate solutions mixed with calcium gluconate at a ratio being over 1:0.2, respectively, also exhibited viscous response (G") greater than the elastic response (G') under oscillatory frequencies in the linear viscoelastic limit. These results indicate that the level of polymer cross-linking in these preparations was negligible.

On the other hand, mixtures of sodium alginate and calcium gluconate at a ratio being under 1:0.5, respectively, formed gels due to substantial polymer cross-linking.

Unexpectedly, mixtures of sodium alginate and calcium gluconate at a ratio ranges between about 1:0.4 to 1:0.3 developed into stable solutions which remained freely flowable for at least 24 hr at room temperature and for at least 30 days at 4-8° C. Mechanical spectra of these novel solutions show a crossover between the viscous response and the elastic response values (FIGS. 3B-C, 4B, 15, 16, 17, 20, 23, 27 and 33 and in Table 3 hereinbelow,). Such behavior is typical of an "entanglement network" viscoelastic material (Clark, A. and Ross-Murphy, S. B., "Structural and Mechanical Properties of Biopolymer Gels. Adv. Poly. Sci. Springer-Verlag, Berlin, Heidelberg, 1987).

TABLE 3

Visual appearance and rheological characteristics of homogenized mixtures of sodium alginate and calcium gluconate

| Alginate Average Mw (kDa) | Sodium Alginate Concentration (% w/v) | Calcium Gluconate Concentration (% w/v) | Visual Appearance | Rheological Characteristics* |
|---|---|---|---|---|
| 15 | 1 | 0 | Flowable solution | G" > G' |
| 15 | 1 | 0.2 | Flowable solution | G" > G' |
| 15 | 1 | 0.3 | Flowable solution | G" > G' |
| 15 | 1 | 0.4 | Flowable solution | G' ≧ G" |
| 15 | 1 | 0.5 | Gel | — |
| 30 | 1 | 0 | Flowable solution | G" > G' |
| 30 | 1 | 0.2 | Flowable solution | G" > G' |
| 30 | 1 | 0.3 | Flowable solution | G' ≧ G" |
| 30 | 1 | 0.4 | Gel | — |
| 30 | 1 | 0.5 | Gel | — |
| 30 | 0.8 | 0 | Flowable solution | G" > G' |
| 30 | 0.8 | 0.2 | Flowable solution | G" > G' |
| 30 | 0.8 | 0.3 | Flowable solution | G' ≧ G" |
| 30 | 0.8 | 0.4 | Gel | — |
| 30 | 0.8 | 0.5 | Gel | — |
| 30 | 1.5 | 0 | Flowable solution | G" > G' |
| 30 | 1.5 | 0.2 | Flowable solution | G" > G' |
| 30 | 1.5 | 0.3 | Flowable solution | G' ≧ G" |
| 30 | 1.5 | 0.4 | Gel | — |
| 30 | 1.5 | 0.5 | Gel | — |
| 100 | 1 | 0 | Flowable solution | G" > G' |
| 100 | 1 | 0.1 | Flowable solution | G" > G' |
| 100 | 1 | 0.2 | Flowable solution | G" > G' |

TABLE 3-continued

Visual appearance and rheological characteristics of homogenized mixtures of sodium alginate and calcium gluconate

| Alginate Average Mw (kDa) | Sodium Alginate Concentration (% w/v) | Calcium Gluconate Concentration (% w/v) | Visual Appearance | Rheological Characteristics* |
|---|---|---|---|---|
| 100 | 1 | 0.23 | Flowable solution | $G'' > G'$ |
| 100 | 1 | 0.25 | Flowable solution | $G'' > G'$ |
| 100 | 1 | 0.270 | Flowable solution | $G' \geqq G''$ |
| 100 | 1 | 0.275 | Flowable solution | $G' \geqq G''$ |
| 100 | 1 | 0.3 | Flowable solution | $G' \geqq G''$ |
| 100 | 1 | 0.35 | Gel | — |
| 100 | 1 | 0.4 | Gel | — |
| 160 | 1 | 0 | Flowable solution | $G'' > G'$ |
| 160 | 1 | 0.2 | Flowable solution | $G'' > G'$ |
| 160 | 1 | 0.3 | Gel | — |
| 160 | 1 | 0.4 | Gel | — |
| 160 | 1 | 0.5 | Gel | — |

*$G'$ = elastic response;
$G''$ = viscous response.

Hence, the results indicate that stable cross-linked alginate solutions can be produced by homogenizing mixtures of sodium alginate and calcium gluconate solutions. The novel cross-linked alginate solutions are freely flowable and exhibit to elastic responses which are equal to or greater than their viscous response under small deformation oscillatory frequencies in the linear viscoelastic limit.

Example 2

Injection of Cross-Linked Alginate Solution into a Rat Infarcted Myocardium Materials and Methods:

Aqueous Cross-Linked Alginate Solution

The solution was made of 1% w/v sodium alginate (Avg. Mw=30 kDa; ratio 2.1) and 0.3% w/v calcium gluconate, as described in Example 1 hereinabove.

Animal Care

The study was performed in accordance with the guidelines of The Animal Care and Use Committee of Ben-Gurion University and Sheba Medical Center, Tel-Aviv University, which conforms to the policies of the American Heart Association and the "Guide for the Care and Use of Laboratory Animals" (Department of Health and Human Services, NIH Publication No. 85-23).

Induction of Myocardial Infarction

Male Sprague-Dawley rats (about 250 g) were anesthetized with a combination of 40 mg/kg ketamine and 10 mg/kg xylazine, intubated and mechanically ventilated. The rat chest was opened by left thoracotomy, the pericardium was removed and the proximal left coronary artery permanently occluded with an intramural stitch.

Injection of the Cross-Linked Alginate Solution One week following MI, animals were anesthetized and their chest was opened under sterile conditions. The infarcted myocardial area was visually recognized based on the appearance of surface scar and wall motion akinesis. The aqueous cross-linked alginate solution or a serum free culture medium (control) were injected (100-200 µL volume) into the scar tissue using a 27-guage needle. Following injection the surgical incision was sutured closed.

Echocardiography

Transthoracic echocardiography was performed on all animals within 24 hours post MI (baseline echocardiogram) and eight weeks following injection using the procedure described by Etzion et al. (J. Mol. Cell. Cardiol. 33: 1321-1330, 2001) and Leor et al. (Circulation 102:11156-61, 2000). The measured parameters were: LV anterior wall thickness; maximal LV end-diastolic dimension; minimal left ventricular end-systolic dimension in M-mode and 2-D imaging; and fractional shortening (as a measure of systolic function) calculated as [FS (%)=(LVIDd–LVIDs)/LVIDd×100], where LVID indicates LV internal dimension, s is systole, and d is diastole. Index of change in LV area (%) was calculated as [(EDA–ESA)/EDA]×100 where EDA indicates LV end diastolic area, ESA indicates LV end systolic area (Mehta et al., J. Am. Coll. Cardiol. 11:630-636, 1988). All measurements were averaged for three consecutive cardiac cycles.

Histological Examination

Eight weeks following injection, animals were sacrificed with an overdose of phenobarbital. Hearts were harvested, and processed for histological and immuno-histochemical examination. Adjacent blocks were embedded in paraffin, sectioned (5 thickness), stained with hematoxylin and eosin then with labeled antibodies against α-actin smooth muscle (SMA; (SIGMA), fast myosin heavy chain (MHC; Sigma), ED1 (Dako), proliferating cell nuclear antigen (PCNA; Enco) and SDF-1 (R&D systems).

Angiogenesis Assessment

The effect of alginate injection upon neoangiogenesis (neovascularization) in the infarcted and peri-infarcted myocardium was assessed by immunohistologic staining of representative slides using anti-αSMA antibody (Sigma) to pericytes and arterioles. Following preliminary microscopic examination under low power, five consecutive adjacent fields were photographed from each section at a magnification of ×200. The number of vessels was assessed from photomicrographs by computerized image analysis to count the number of vessels and to calculate vessel density (mean number of capillaries and arterioles/$mm^2$) in the myocardium of treated and control animals.

Statistical Analysis

Univariate differences between the control and treated groups were analyzed using t tests for continuous variables. Changes between baseline and eight week data were analyzed using paired t tests. Comparisons of the changes between baseline and eight week data were analyzed by repeated-measures ANOVA, using GraphPad Prism version 4.00 for Windows (GraphPad Software, San Diego, Calif., USA). The ANOVA model included the control versus treated and baseline versus eight week as factors and the interaction between the two factors (Perin et al., Circulation; 107:2294-2302, 2003). A probability value $p \leqq 0.05$ was considered statistically significant.

Results:

In one experiment, seven days post MI, rats were treated with either cross-linked alginate solution, embryonic cardiomyocyte suspension ($1.5 \times 10^6$ cells; cells control)) or a serum free culture medium (medium control). 2-D echocardiography results (Table 4) show that the cross-linked alginate solution per se increased scar thickness, increased cardiac contractility and reduced LV dilatation and dysfunction, as compared with the medium control.

TABLE 4

| | 2-D echocardiography analyses | | | | | | | | | |
|---|---|---|---|---|---|---|---|---|---|---|
| | Treatment[1] (n = 8) | | | Cells Control (n = 5) | | | Medium Control (n = 4) | | | |
| | Pre injection | 8 wk Post Injection | P value | Pre injection | 8 wk Post Injection | P value | Pre injection | 8 wk Post Injection | P value | ANOVA P value |
| AW (d cm) | 0.12 ± 0.01 | 0.15 ± 0.01 | 0.03 | 0.11 ± 0.004 | 0.14 ± 0.01 | 0.01 | 0.12 ± 0.005 | 0.11 ± 0.01 | 0.9 | 0.3 |
| LVEDD (cm) | 0.71 ± 0.02 | 0.86 ± 0.06 | 0.07 | 0.68 ± 0.03 | 0.69 ± 0.02 | 0.7 | 0.73 ± 0.04 | 0.97 ± 0.04 | 0.003 | 0.01 |
| LVESD (cm) | 0.52 ± 0.05 | 0.65 ± 0.07 | 0.1 | 0.45 ± 0.03 | 0.45 ± 0.04 | 0.9 | 0.56 ± 0.05 | 0.81 ± 0.04 | 0.004 | 0.01 |
| LVED area cm$^2$ | 0.4 ± 0.03 | 0.6 ± 0.07 | 0.03 | 0.40 ± 0.04 | 0.40 ± 0.01 | 1 | 0.41 ± 0.06 | 0.66 ± 0.05 | 0.007 | 0.06 |
| LVES area cm$^2$ | 0.2 ± 0.4 | 0.3 ± 0.06 | 0.1 | 0.17 ± 0.02 | 0.19 ± 0.03 | 0.7 | 0.24 ± 0.04 | 0.43 ± 0.04 | 0.009 | 0.05 |
| LV FS (%) | 27 ± 5 | 25 ± 4 | 0.6 | 34 ± 3 | 35 ± 6 | 0.8 | 24 ± 3 | 17 ± 1 | 0.06 | 0.06 |
| FAC (%) | 44 ± 4 | 44 ± 5 | 1 | 57 ± 2 | 54 ± 6 | 0.6 | 42 ± 2 | 36 ± 1 | 0.14 | 0.08 |

[1]Treatment - cross linked alginate solution
[2]Cells control - fetal cardiomycetes suspended (1 × 10$^6$ cells) in culture medium
[3]Medium control - culture medium only
AW d—Anterior wall diastolic thickness
LVEDD—LV end diastolic dimension
LVESD—LV end systolic dimension
LV ED area—LV end diastolic area
LV ES area—LV end systolic area
LV FS—LV fractional shortening - [(LVIDd − LVIDs)/LVIDd] × 100
FAC %—Fractional area change - [(EDA − ESA)/EDA] × 100

In another experiment, rats the cross-linked alginate solution or with a serum free culture medium was injected into rat myocardial scar 7 days post MI. In addition, two rats with normal heart were treated with the cross-linked alginate solution.

Echocardiography results show significant increases in LV diastolic and systolic internal diameters were observed in control animals, which indicate extensive myocardial infarction, LV remodeling and heart failure (FIGS. 5, 6; Table 5). In addition, the LV end-diastolic and systolic cavity areas increased by 75% and by over 100%, respectively, in the control animals (FIGS. 5, 6, Table 5; p<0.05). These results are consistent with the process observed in human patients following extensive anterior MI (Pilla et al., Circulation 106: 1207-211, 2002). Progressive LV dilatation from baseline was also accompanied by significant deterioration in LV performance, reflected by the deterioration of fractional shortening (from 30±5% at baseline to 22±3%; p<0.05) and percentage of LV fractional area change (from 49±5% to 38±3%; p<0.05; FIG. 7).

On the other hand, the cross-linked alginate solution significantly increased the scar thickness (p<0.0001) and attenuated the typical course of LV dilation complicating extensive anterior MI (FIG. 5; Table 5). Furthermore, the cross-linked alginate solution substantially reduced the LV diastolic and systolic dimensions, as compared with the control animals (FIG. 5; Table 5).

TABLE 5

| | 2-D and Doppler echocardiography analyses | | | | | | |
|---|---|---|---|---|---|---|---|
| | Treatment[1] (n = 15) | | | Control[2] (n = 9) | | | Treatment vs. Control P value |
| | Pre injection | 8 wk Post Injection | P value | Pre injection | 8 wk Post Injection | P value | |
| AW (d cm) | 0.14 ± 0.01 | 0.16 ± 0.01 | <0.001 | 0.14 ± 0.01 | 0.14 ± 0.01 | 0.8 | 0.16 |
| LVEDD (cm) | 0.71 ± 0.02 | 0.86 ± 0.03 | <0.01 | 0.73 ± 0.02 | 0.98 ± 0.03 | <0.0001 | 0.02 |
| LVESD (cm) | 0.50 ± 0.03 | 0.65 ± 0.04 | <0.01 | 0.51 ± 0.04 | 0.78 ± 0.05 | <0.0001 | 0.05 |
| LVED area cm$^2$ | 0.38 ± 0.03 | 0.56 ± 0.05 | 0.17 | 0.40 ± 0.03 | 0.70 ± 0.03 | <0.0001 | 0.05 |
| LVES area cm$^2$ | 0.21 ± 0.03 | 0.32 ± 0.04 | 0.05 | 0.20 ± 0.02 | 0.44 ± 0.04 | <0.0001 | 0.06 |

TABLE 5-continued

| | 2-D and Doppler echocardiography analyses | | | | | | |
|---|---|---|---|---|---|---|---|
| | Treatment[1] (n = 15) | | | Control[2] (n = 9) | | | Treatment vs. Control |
| | Pre injection | 8 wk Post Injection | P value | Pre injection | 8 wk Post Injection | P value | P value |
| LV FS (%) | 29 ± 3 | 25 ± 2 | 0.2 | 30 ± 5 | 20 ± 3 | 0.02 | 0.3 |
| FAC (%) | 47 ± 4 | 45 ± 3 | 0.6 | 49 ± 4 | 38 ± 3 | 0.02 | 0.1 |

[1]Treatment - cross-linked alginate solution
[2]Control - culture medium
AW d—Anterior wall diastolic thickness
LVEDD—LV end diastolic dimension
LVESD—LV end systolic dimension
LV ED area—LV end diastolic area
LV ES area—LV end systolic area
LV FS—LV fractional shortening - [(LVIDd − LVIDs)/LVIDd] × 100
FAC %—Fractional area change - [(EDA − ESA)/EDA] × 100

Figure 8:
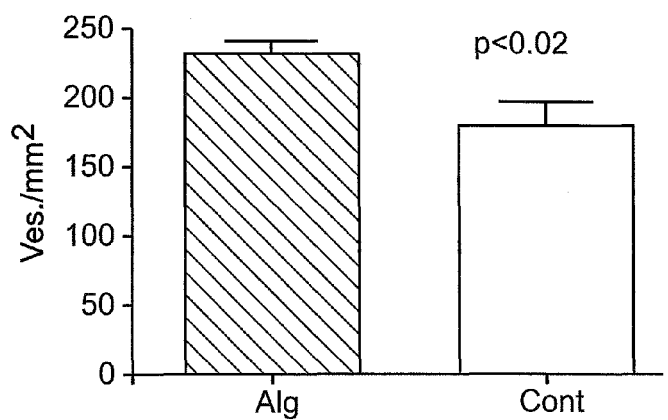
FIG. 8 illustrates the effect of the cross-linked alginate solution on neoangiogenesis (in number of vessels per area) in rat infracted myocardium. Abbreviations: Ves., vessels; Alg., alginate; cont., control.

Immunostaining with anti α-SMA antibody indicates increased neoangiogenesis and migration of myofibroblasts in myocardium which had been treated with the cross-linked alginate solution, as compared with untreated control. The blood vessel density values in treated and control myocardium were 231±13 and 180±16, respectively (p<0.02; FIG. 8).

Immunostaining with anti-PCNA antibody indicates DNA activity and proliferation of endothelial cells and cardiomyocytes in the treated myocardium.

Hence, these results indicate that the cross-linked alginate solution of the present invention can substantially improve the heart function of rats following MI and promote angiogenesis and regeneration of the damaged myocardium.

Example 3

Injection of Cross-Linked Alginate Solution into a Pig Infarcted Myocardium

Materials and Methods:
Aqueous Cross-Linked Alginate Solution

The solution was made of 1% w/v sodium alginate (Avg. Mw=30 kDa; G/M ratio 2.1) and 0.3% w/v calcium gluconate, as described in Example 1 hereinabove.

Animal Care

The study was performed in accordance with the guidelines of The Animal Care and Use Committee of Ben-Gurion University and Sheba Medical Center, Tel-Aviv University, which conforms to the policies of the American Heart Association and the "Guide for the Care and Use of Laboratory Animals" (Department of Health and Human Services, NIH Publication No. 85-23).

Induction of Myocardial Infarct (MI)

Myocardial infarct was induced according to Yau et al. (Ann Thorac Surg 75:169-176, 2003) and Watanabe et al. (Cell Transplant 7:239-246, 1998). Briefly, female Sincklaire (mini) pigs weighing 30-40 kg were pre-medicated with ketamine (20 to 30 mg/kg, intramuscular) before anesthetic induction with 4% isoflurane. Anesthesia was maintained with isoflurane 1% to 2.5%. The right femoral artery was isolated and cannulated with an introduction sheath. Through this, a cardiac catheter was placed in the mid portion of the left anterior descending artery (LAD) and an embolization coil (Boston Scientific, USA) was extruded from the catheter with a guide wire and placed in the distal portion of LAD under fluoroscopic guidance. This procedure induced a thrombus resulting in myocardial infarction in the left ventricle, which was confirmed by angiography and electrocardiography. Electrical DC cardioversion was given as was necessary.

Induction of Mitral Regurgitation (MR)

Mitral regurgitation was produced by creating extensive posterior MI following coil embolization of the circumflex coronary artery.

Injection of the cross-linked alginate solution

For evaluating the effect of the cross-linked alginate solution on MI, four animals were subjected to anterior MI. Five of these animals were injected with the cross-linked alginate solution and the other five animals were injected with saline (control). For evaluating the effect of cross-linked alginate solution on MR, four animals were subjected to posterolateral MI. Two of these animals were injected with the cross-linked alginate solution and the other two animals were injected with saline (control).

Myocardium injections were performed 7 to 10 days post MI as follows: animals were anesthetized, their chest was opened and the infarcted area was identified visually by surface scar and wall motion abnormality. Aliquots (about 2.5 ml) of the cross-linked alginate solution, or saline control, were injected into the infracted myocardium. Following injection, air was expelled from the chest and the surgical incision sutured closed. Eight weeks following treatment, all surviving animals were euthanized with overdosed Phenobarbital then their hearts were harvested and processed for histological analyses.

Echocardiography

Ecocardiogram analysis was performed immediately following MI prior to injection treatment, as well as on day 10, 30 and 60 following MI. The analyses were performed using a phased-array transducer (2.5 MHz) equipped with an ultrasound system (Sonos 5500, Hewlett-Packard, Andover, Mass.). Images were recorded on VHS videotape. End-diastolic and end-systolic frames were selected from standard apical and parasternal views.

Global LV ejection fraction (LVEF) was estimated visually. LV volumes were measured by manually tracing the left ventricular cavity using the single plane modified Simpson's algorithm when >80% of the endocardial border could be detected in both the apical 4- and 2-chamber views, and by a single plane when 80% of the endocardial border could be detected only in the apical 4-chamber view.

Regional myocardial assessment and wall motion score index values were determined by assigning a segmental score (1=normal, 2=hypokinetic, 3=akinetic, 4=dyskinetic) to each of the 16 left ventricular segments, as recommended by the American Society of Echocardiography (Schiller et al., J. Am. Soc. Echocardiogr. 2:358-367, 1989). All segment scores were added and divided by the number of segments analyzed to obtain the wall motion score index. Left ventricular wall motion score index (WMSI) was derived using the sum of the individual scores divided by the total number of analyzed segments. Regional motion score index was calculated by the same method for the segments of the mid-LAD territory (infarct related artery territory). The data were interpreted by a single experienced observer, and all measurements were obtained off line by a single technician.

Mytral regrugiration (MR) was graded by color Doppler flow mapping using an algorithm which integrated jet expansion within the left atrium jet eccentricity. The size of the proximal area. MR was considered mild when the regurgitant jet area was under 20% of the LA area (in the absence of a wall jet and a proximal isovelocity surface area visible without baseline shifting). MR was considered severe when regurgitant jet area occupied was over 40% of the LA area. Jet eccentricity or a sizable proximal flow convergence radius (0.6 mm in a patient with jet area under 20%, or 0.9 mm in a patient with a jet area between 20% and 40%) raised the grade of MR by one degree.

Morphological and Histological Examination

Animal hearts were arrested with potassium chloride and rapidly excised. Their atria were removed and the coronary arteries were perfused with 100 mL 10% formaldehyde. The myocardium was fixed in diastole with an intraventricular pressure (30 mm Hg) in formaldehyde solution. Following fixation, the myocardium was sliced (5 mm thick) and each section was photographed. The mean scar length was calculated as the mean of the epicardial and the endocardial scar lengths. The scar area was calculated as the mean scar length multiplied by 0.5 cm. The total scar area was calculated as the sum of scar areas of all sections combined and the scar volume was calculated as total scar area multiplied by the mean scar thickness. A cube of tissue from the center of the infarct zone measuring about 5 mm$^3$ was embedded in paraffin and cut into 5 µm sections for staining with hematoxylin and eosin.

For immunohistochemical examination, tissue slices were serially rehydrated in 100%, 95%, and 70% ethanol after deparaffinization with toluene. Endogenous peroxidase in the sample was blocked and the samples were stained with antibodies. Adjacent blocks were embedded in paraffin, sectioned into 5 µm slices and stained with hematoxylin and eosin. Serial sections were immunolabelled with antibodies against SMA, slow MHC (Sigma), Ki67 (Novocastra Ltd.) and SDF-1 (R&D systems).

Statistical Analysis

Univariate differences between the control and treated groups were analyzed using t tests for continuous variables. Changes between baseline and eight week data were analyzed using paired t tests. Comparisons of the changes between baseline and eight week data were analyzed by repeated-measures ANOVA using GraphPad Prism version 4.00 for Windows (GraphPad Software, San Diego, Calif., USA). The ANOVA model included the control versus treated and baseline versus eight week as factors and the interaction between the two factors (Perin et al., Circulation; 107:2294-2302, 2003). A probability value p≦0.05 was considered statistically significant.

Results:

During 60 days post MI two out of five animals of the control groups died (3 and 49 days post MI). All of the five treated animals survived the 60 days period post MI.

The treated myocardium exhibited high density of endothelial cells and cardiomyocytes which reacted with anti-Ki67. antibody (indicative of DNA activity). In contrast, the control myocardium exhibited high density of cells having fibroblast morphology, while reactivity with Ki67 was observed within the infarct zone only. These observations indicate that the cross-linked alginate solution is capable of inducing proliferation of endothelial cells and cardiomyocytes and, consequently, cardiac regeneration.

Figures 9A, 9B:
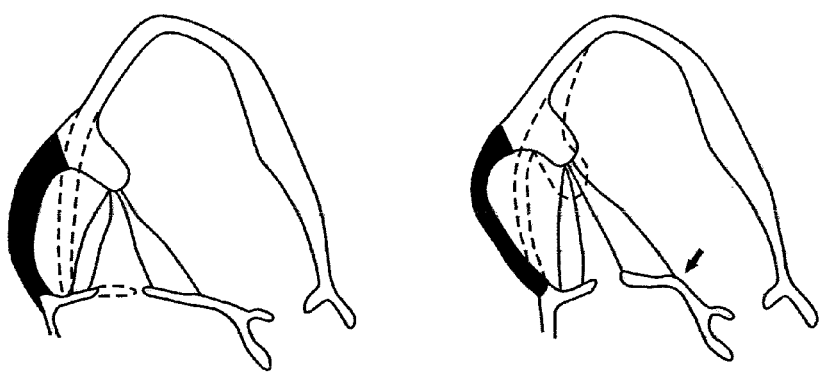
FIGS. 9A-B illustrate the effect of the cross-linked alginate solution on reversing ischemic mitral regurgitation (MR).
Figure 10:
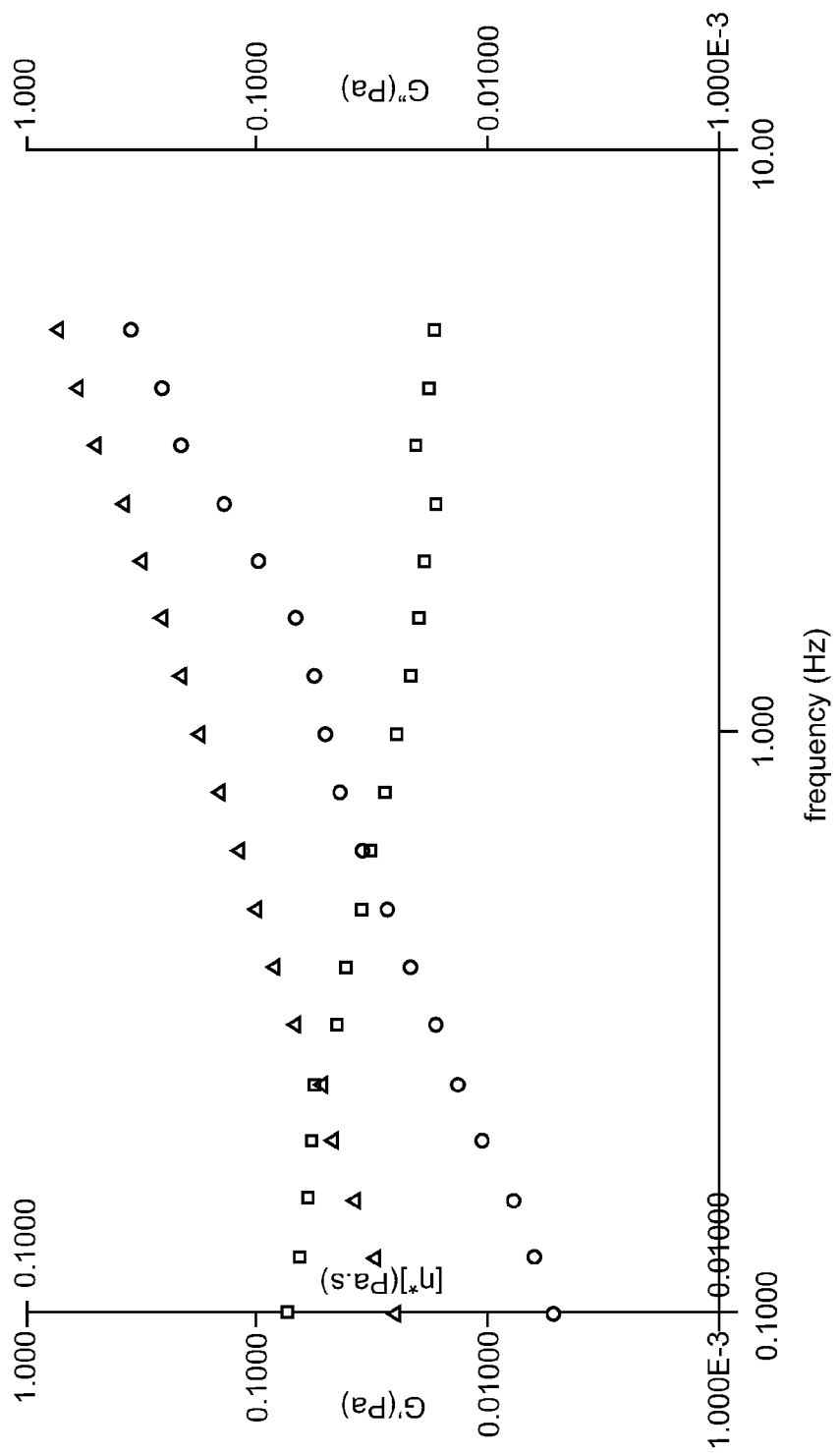
FIG. 10 illustrates a mechanical spectrum of an aqueous solution of 1% (w/v) alginate (Avg. Mw=100 kDa) with no calcium gluconate added. Red circles=elastic response (G'); triangles=viscous response (G"); squares=complex viscosity.
Figure 11:
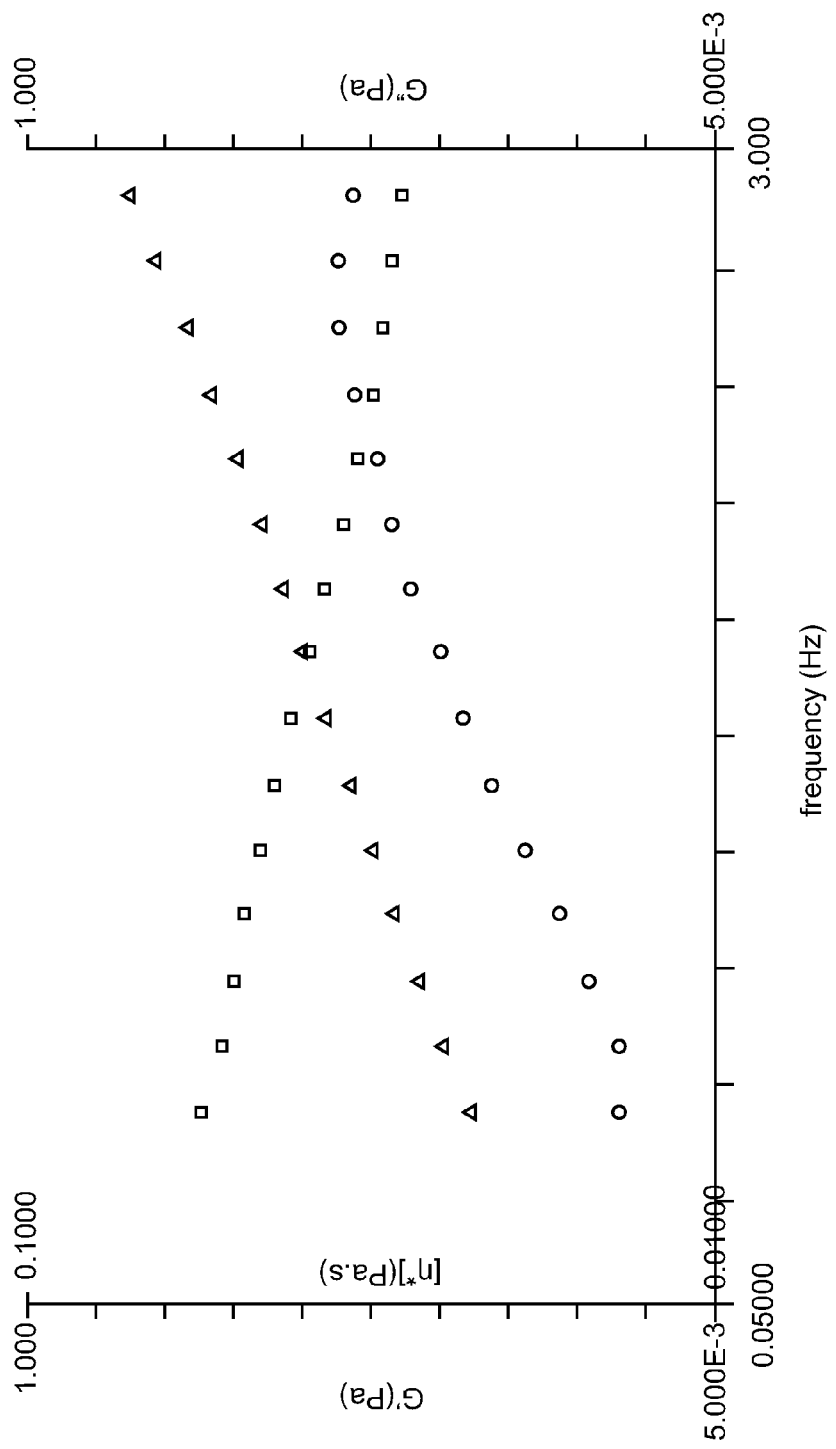
FIG. 11 illustrates a mechanical spectrum of an aqueous solution of 1% (w/v) alginate (Avg. Mw=100 kDa) mixed with 0.1% (w/v) calcium gluconate. circles=elastic response (G'); triangles=viscous response (G"); squares=complex viscosity.
Figure 12:
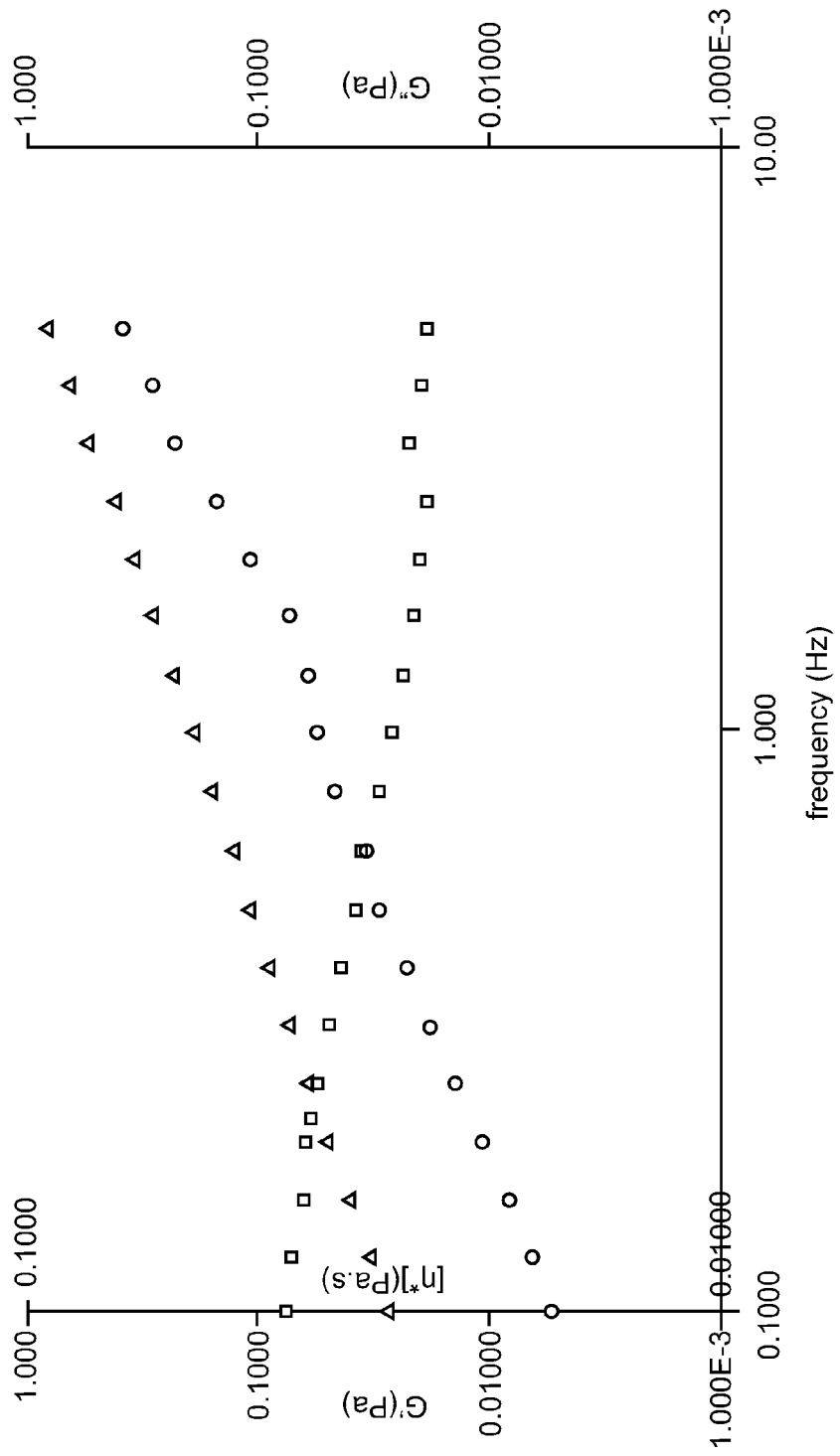
FIG. 12 illustrates a mechanical spectrum of an aqueous solution of 1% (w/v) alginate (Avg. Mw=100 kDa) mixed with 0.2% (w/v) calcium gluconate. circles=elastic response (G'); triangles=viscous response (G"); squares=complex viscosity.
Figure 13:
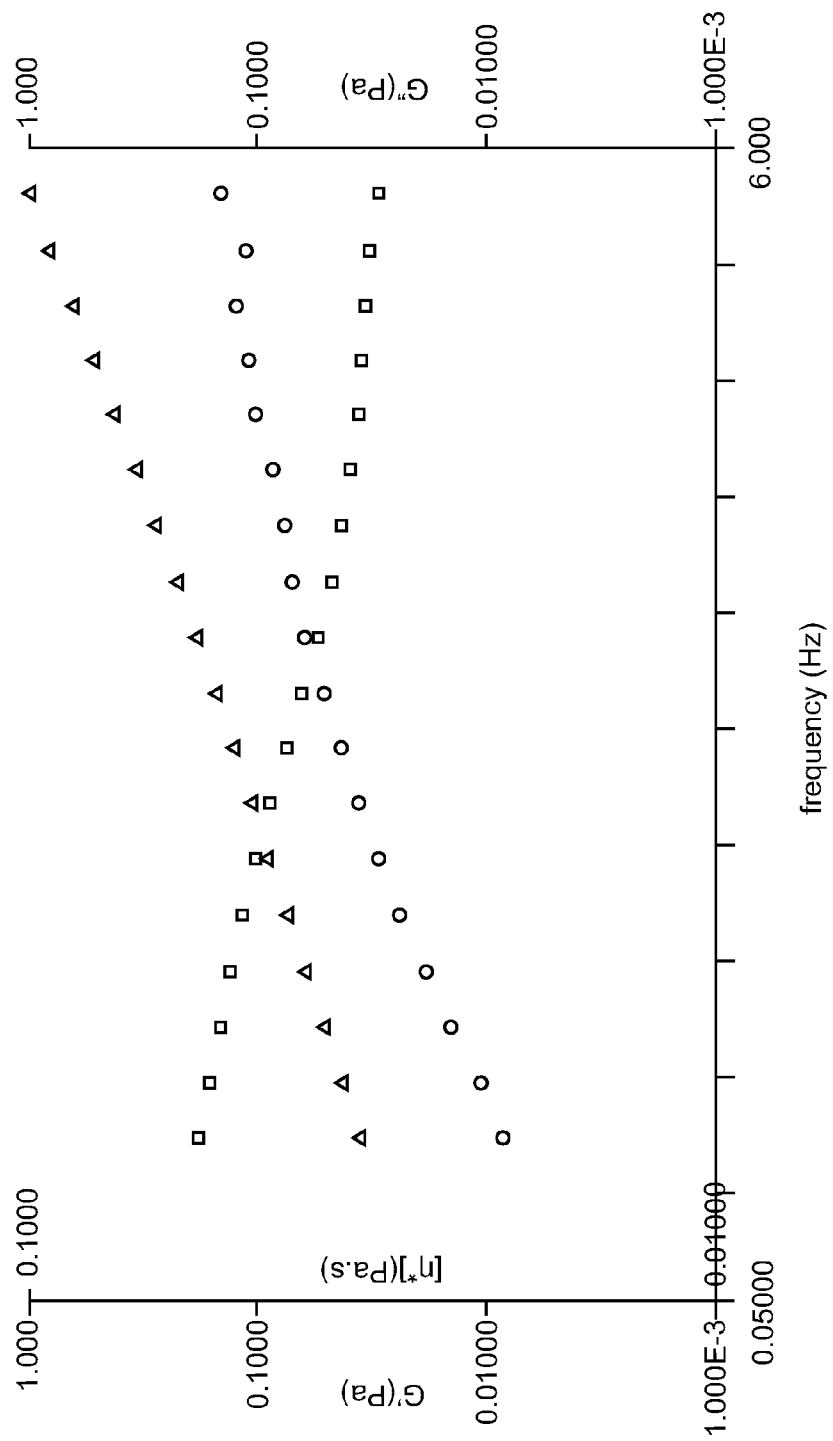
FIG. 13 illustrates a mechanical spectrum of an aqueous solution of 1% (w/v) alginate (Avg. Mw=100 kDa) mixed with 0.23% (w/v) calcium gluconate. circles=elastic response (G'); triangles=viscous response (G"); squares=complex viscosity.
Figure 14:
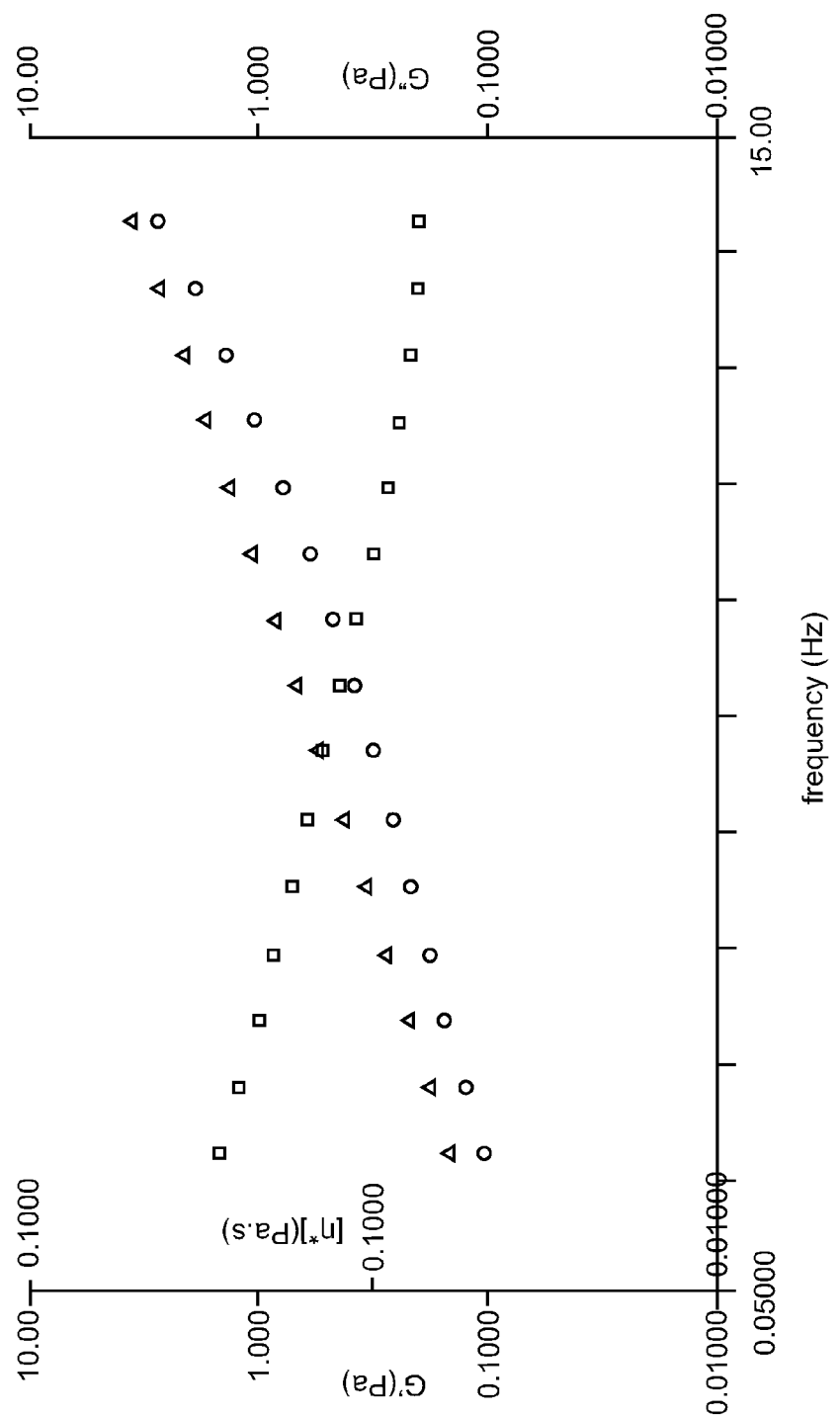
FIG. 14 illustrates a mechanical spectrum of an aqueous solution of 1% (w/v) alginate (Avg. Mw=100 kDa) mixed with 0.25% (w/v) calcium gluconate. circles=elastic response (G'); triangles=viscous response (G"); squares=complex viscosity.
Figure 15:
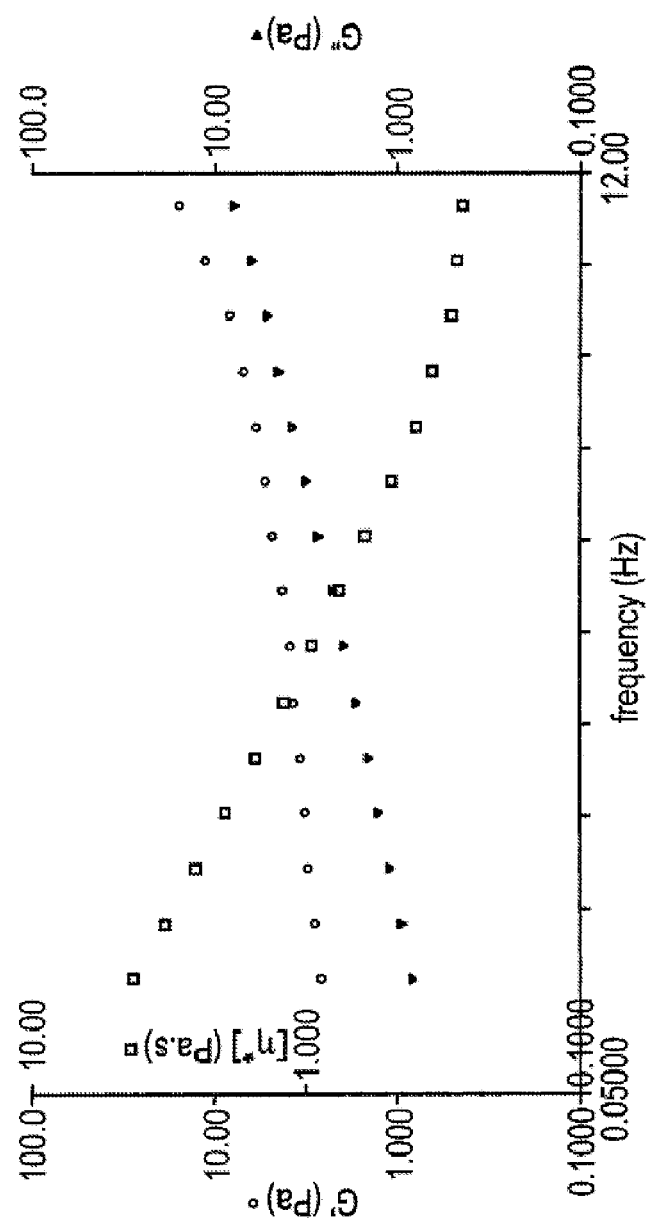
FIG. 15 illustrates a mechanical spectrum of an aqueous solution of 1% (w/v) alginate (Avg. Mw=100 kDa) mixed with 0.3% (w/v) calcium gluconate. Red circles=elastic response (G'); blue triangles=viscous response (G"); black squares=complex viscosity.
Figure 16:
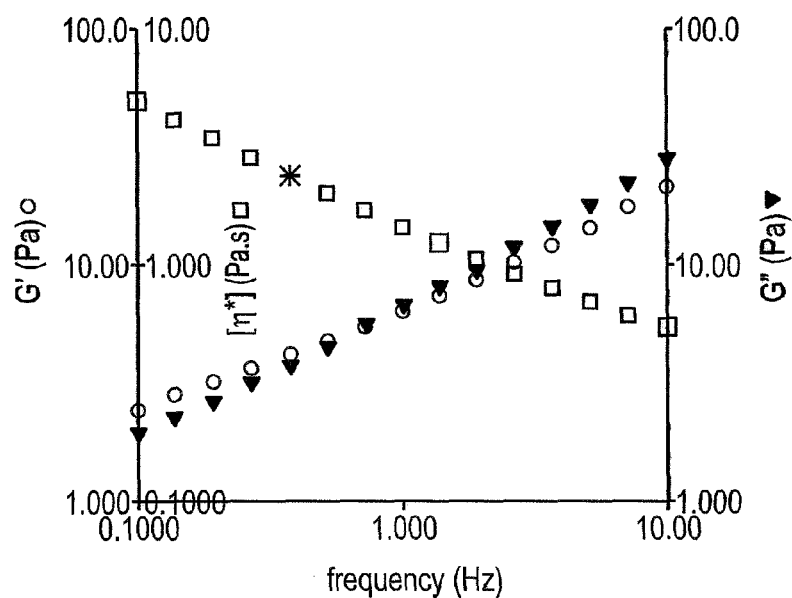
FIG. 16 illustrates a mechanical spectrum of an aqueous solution of 1% (w/v) alginate (Avg. Mw=100 kDa) mixed with 0.275% (w/v) calcium gluconate. circles=elastic response (G'); triangles=viscous response (G"); squares=complex viscosity.
Figure 17:
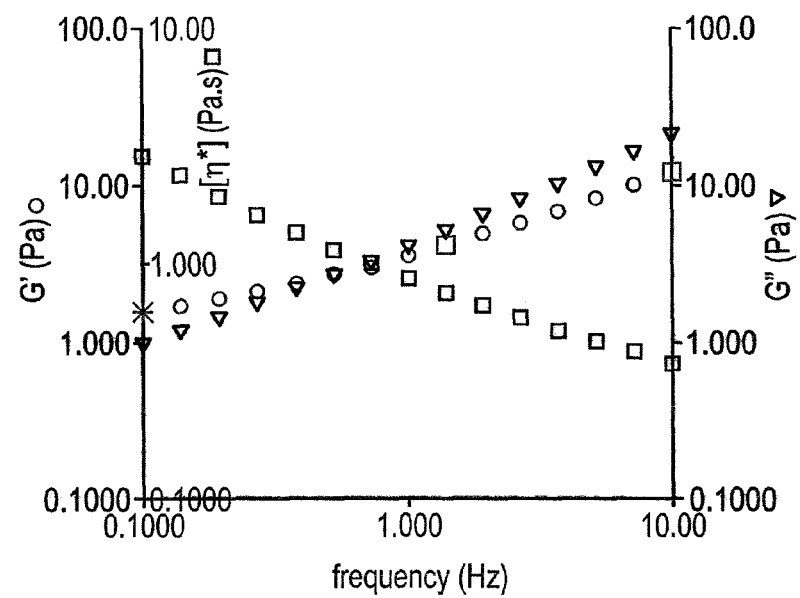
FIG. 17 illustrates a mechanical spectrum of an aqueous solution of 1% (w/v) alginate (Avg. Mw=100 kDa) mixed with 0.270% (w/v) calcium gluconate. circles=elastic response (G'); triangles=viscous response (G"); squares=complex viscosity.
Figure 18:
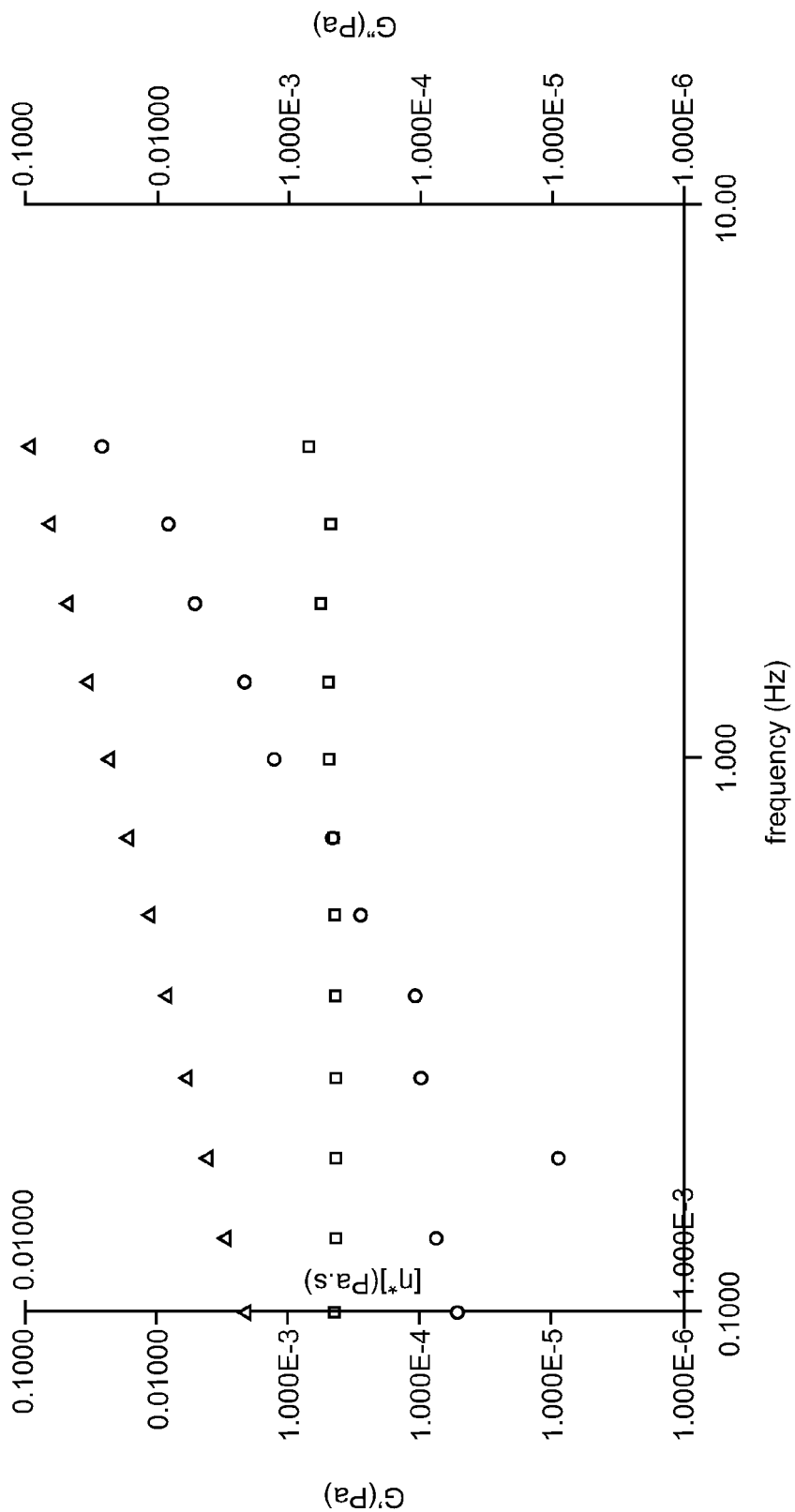
FIG. 18 illustrates a mechanical spectrum of an aqueous solution of 1% (w/v) alginate (Avg. Mw=30 kDa) with no calcium gluconate added. circles=elastic response (G'); triangles=viscous response (G"); squares=complex viscosity.
Figure 19:
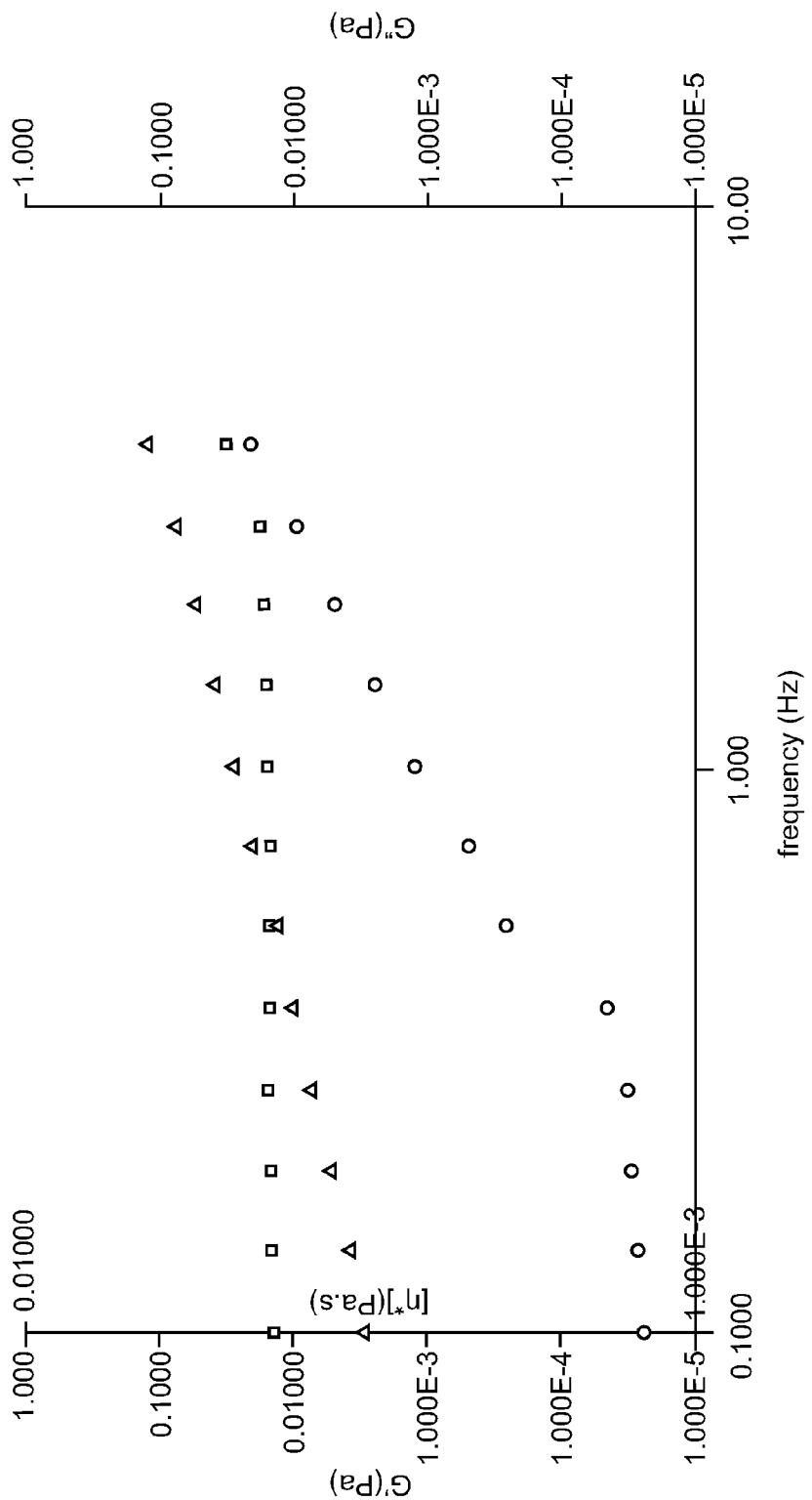
FIG. 19 illustrates a mechanical spectrum of an aqueous solution of 1% (w/v) alginate (Avg. Mw=100 kDa) mixed with 0.2% (w/v) calcium gluconate. circles=elastic response (G'); triangles=viscous response (G"); squares=complex viscosity.
Figure 20:
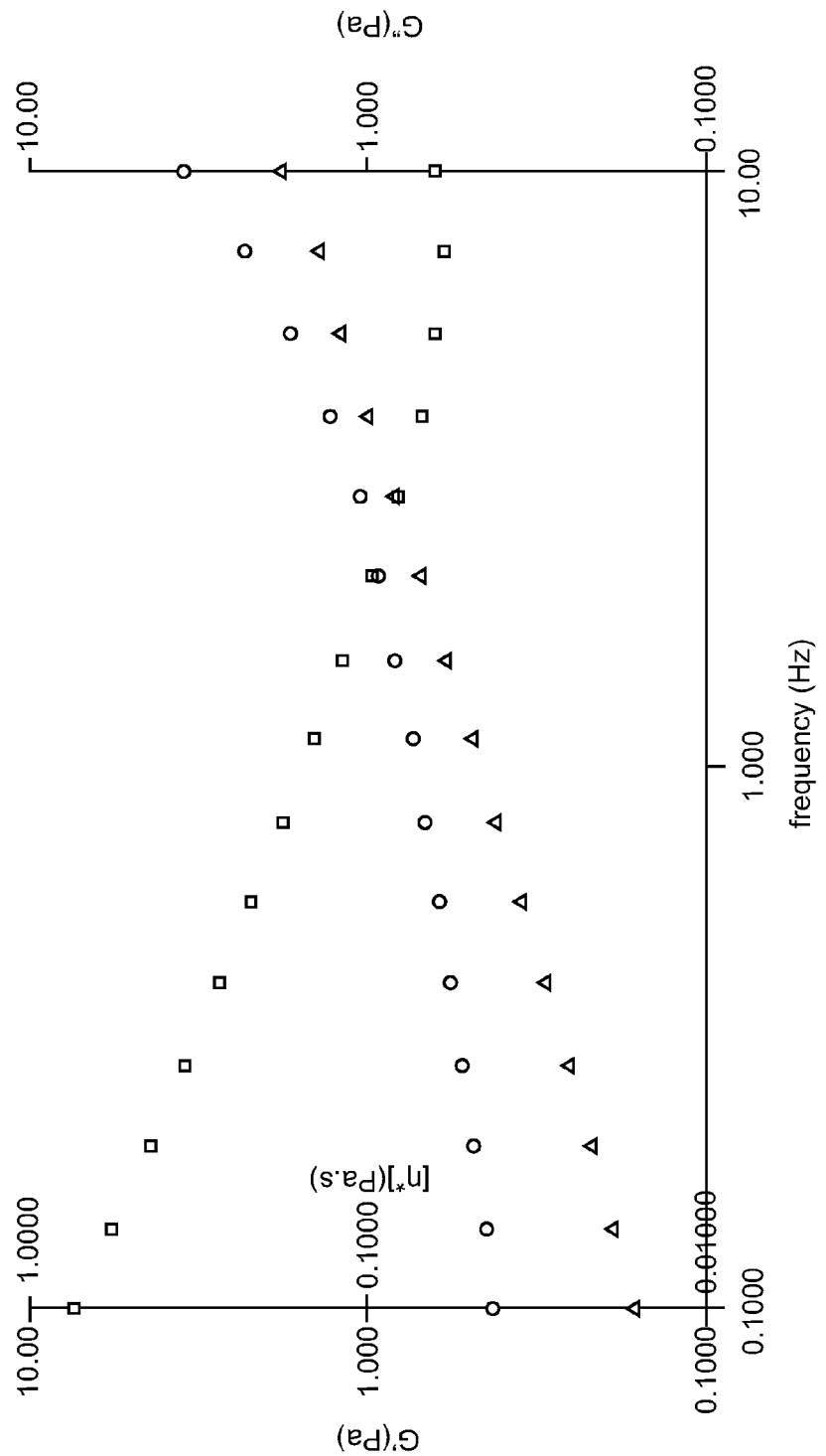
FIG. 20 illustrates a mechanical spectrum of an aqueous solution of 1% (w/v) alginate (Avg. Mw=30 kDa) mixed with 0.3% (w/v) calcium gluconate. circles=elastic response (G'); triangles=viscous response (G"); squares=complex viscosity.
Figure 21:
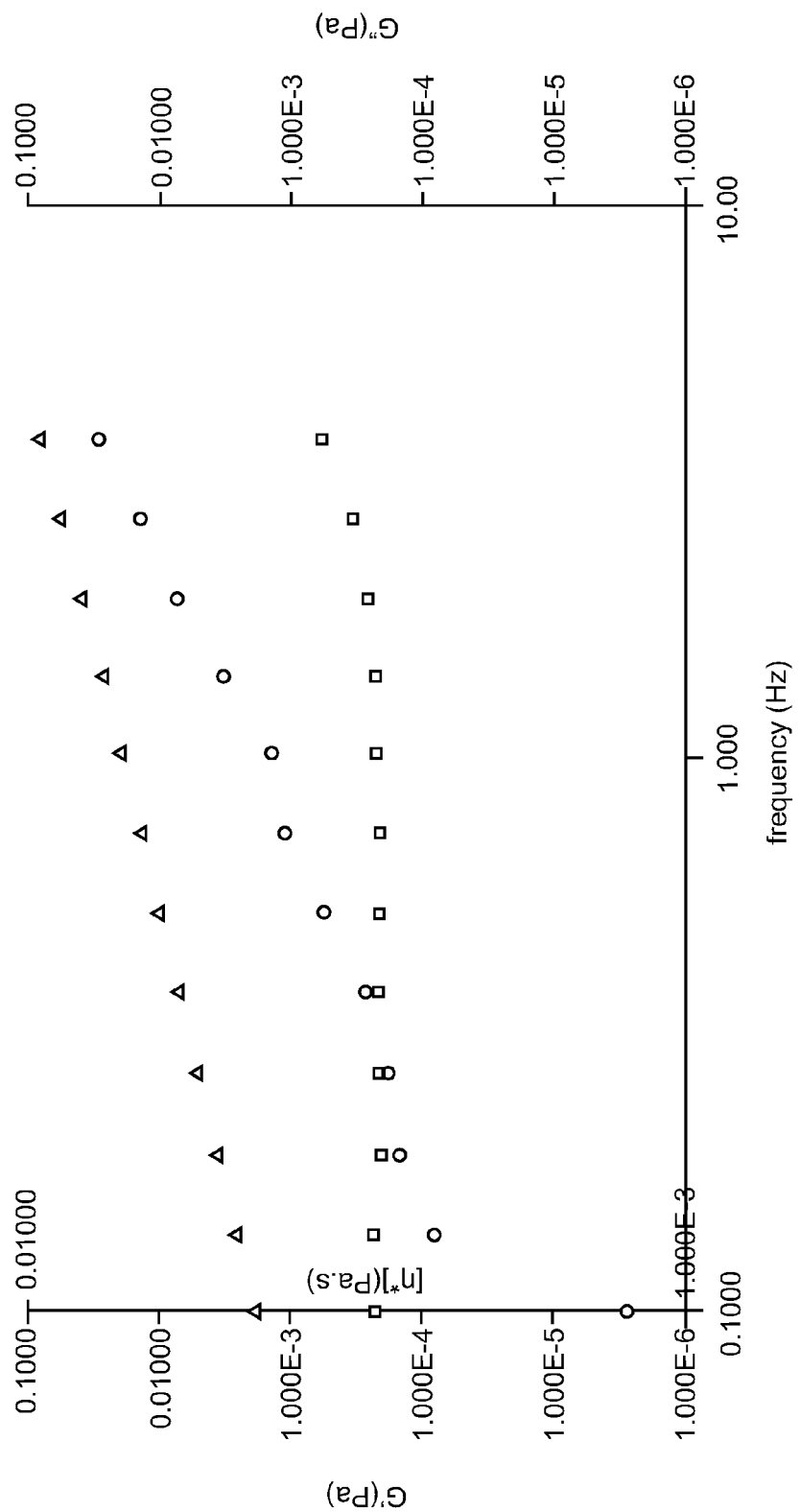
FIG. 21 illustrates a mechanical spectrum of an aqueous solution of 0.8% (w/v) alginate (Avg. Mw=30 kDa) with no calcium gluconate added. circles=elastic response (G'); triangles=viscous response (G"); squares=complex viscosity.
Figure 22:
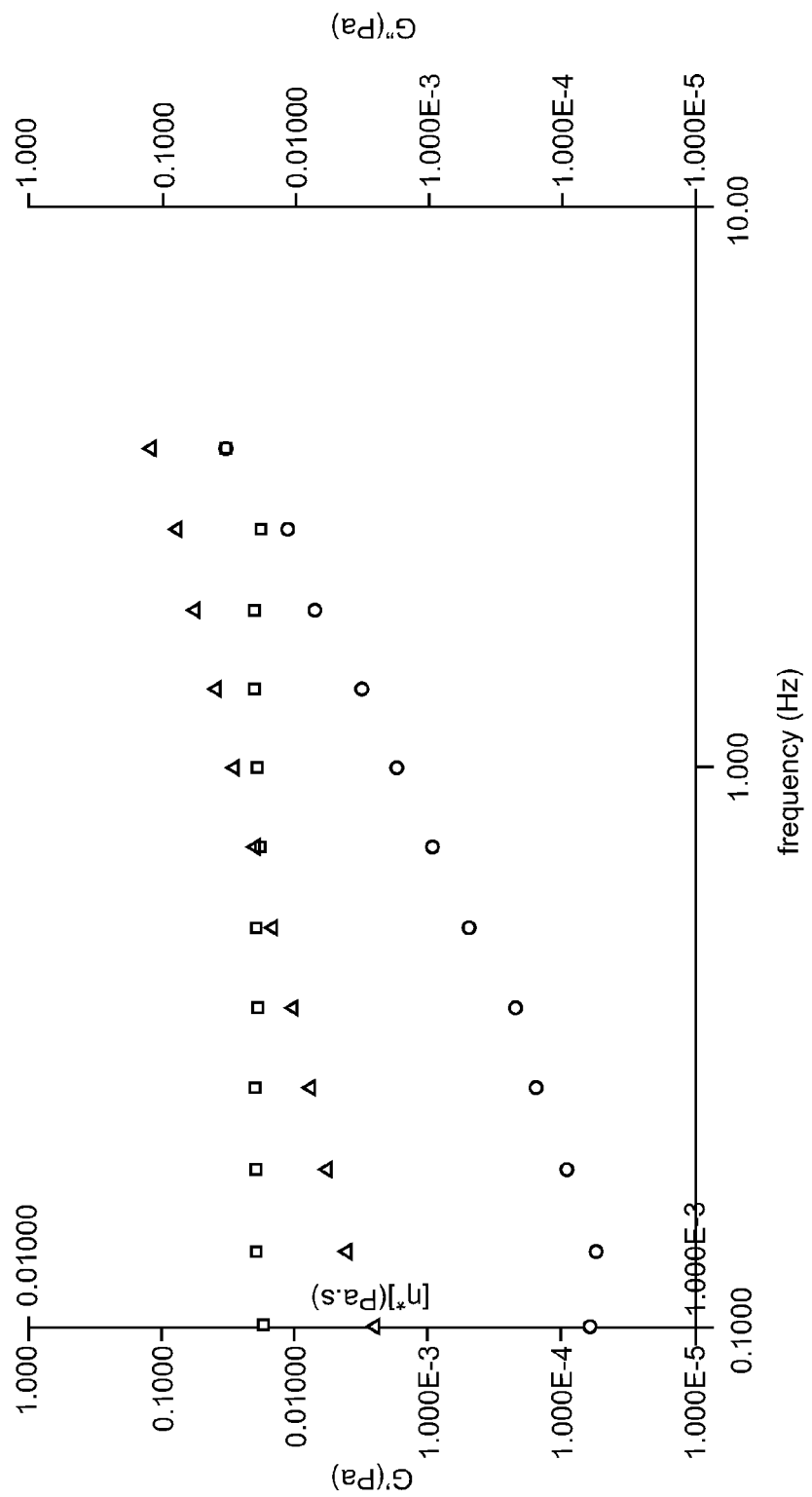
FIG. 22 illustrates a mechanical spectrum of an aqueous solution of 0.8% (w/v) alginate (Avg. Mw=30 kDa) mixed with 0.2% (w/v) calcium gluconate. circles=elastic response (G'); triangles=viscous response (G"); squares=complex viscosity.
Figure 23:
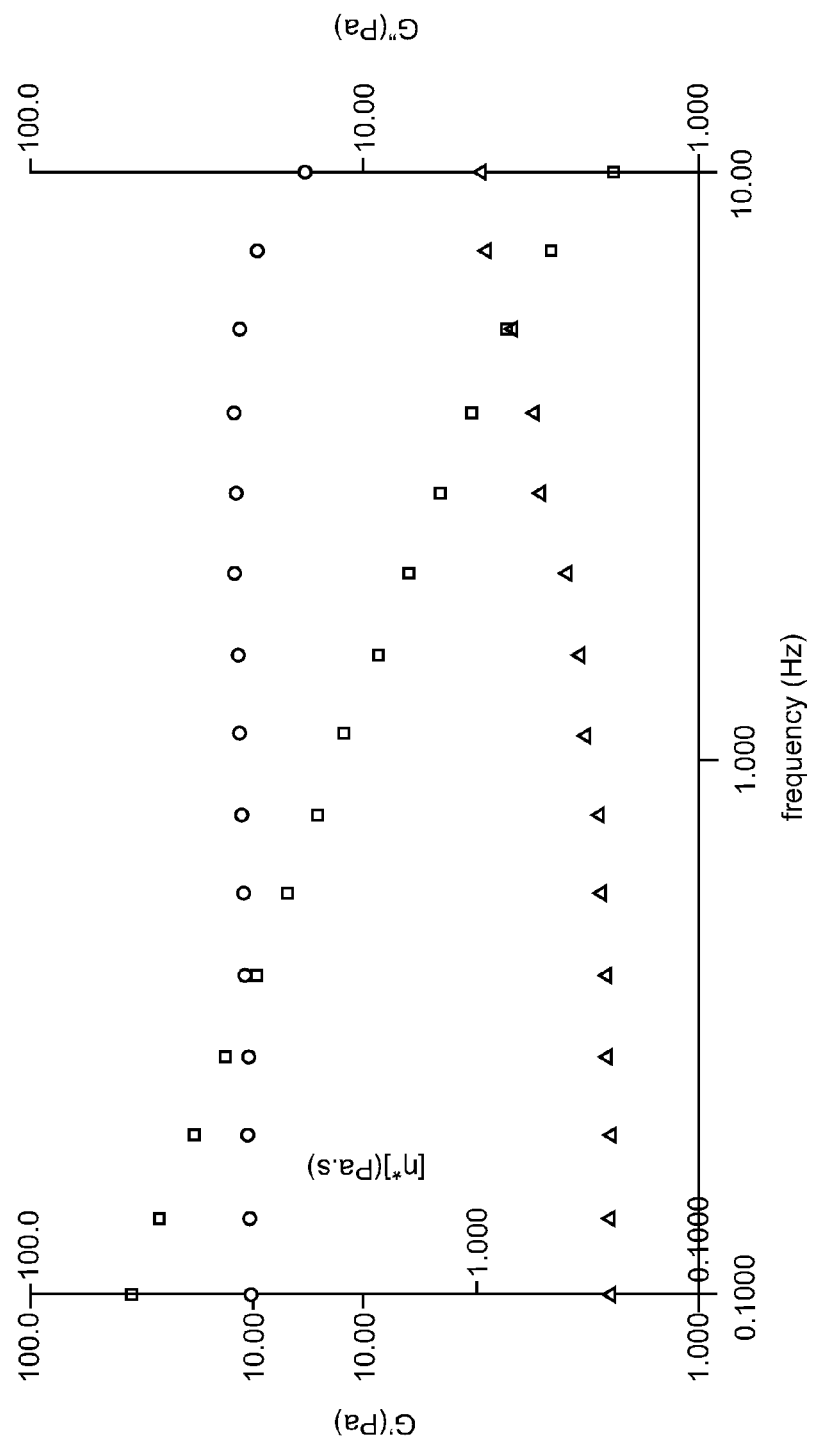
FIG. 23 illustrates a mechanical spectrum of an aqueous solution of 0.8% (w/v) alginate (Avg. Mw=30 kDa) mixed with 0.3% (w/v) calcium gluconate. circles=elastic response (G'); triangles=viscous response (G"); squares=complex viscosity.
Figure 24:
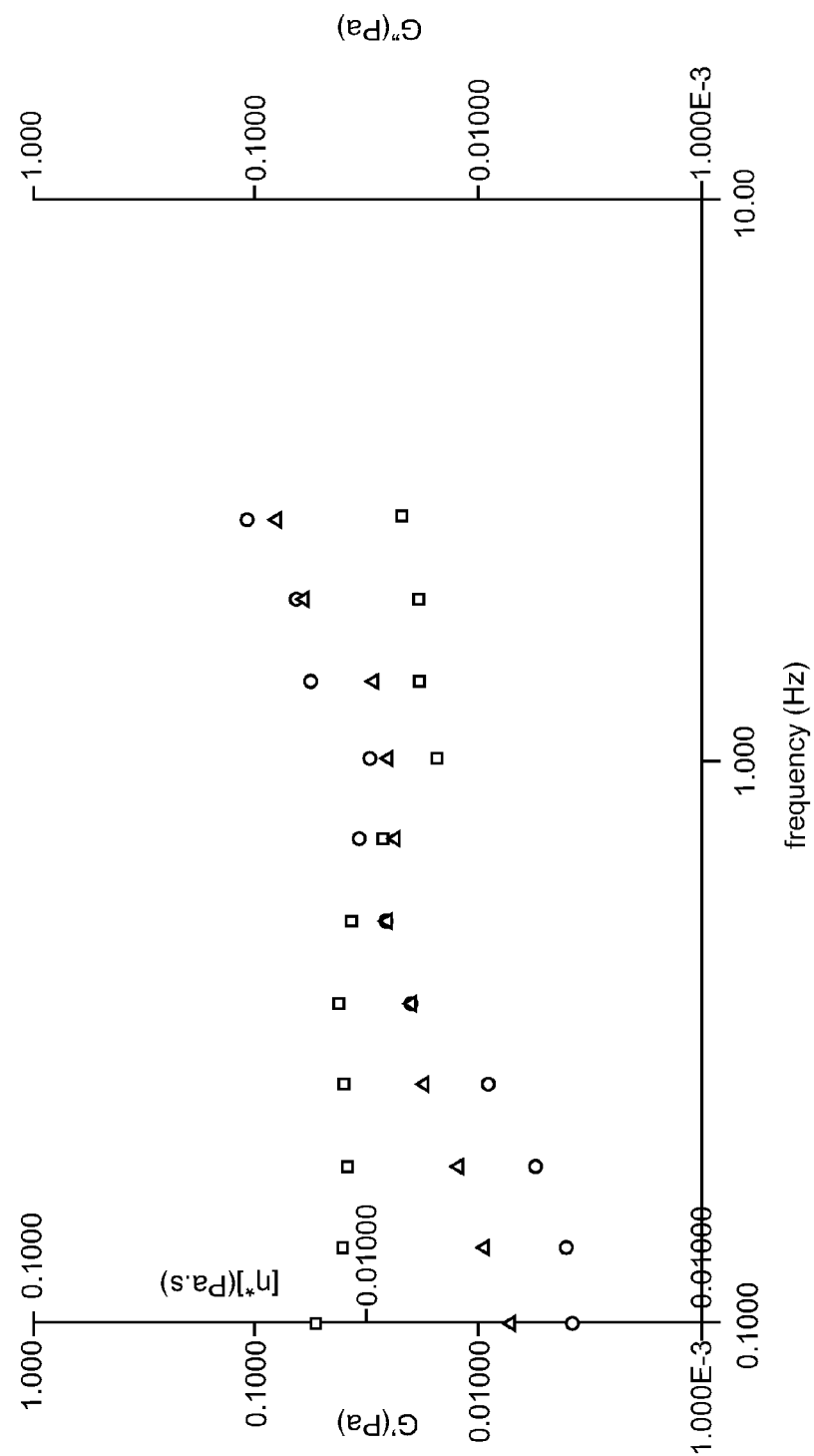
FIG. 24 illustrates a mechanical spectrum of an aqueous solution of 1.5% (w/v) alginate (Avg. Mw=30 kDa) with no calcium gluconate added. circles=elastic response (G'); triangles=viscous response (G"); squares=complex viscosity.
Figure 25:
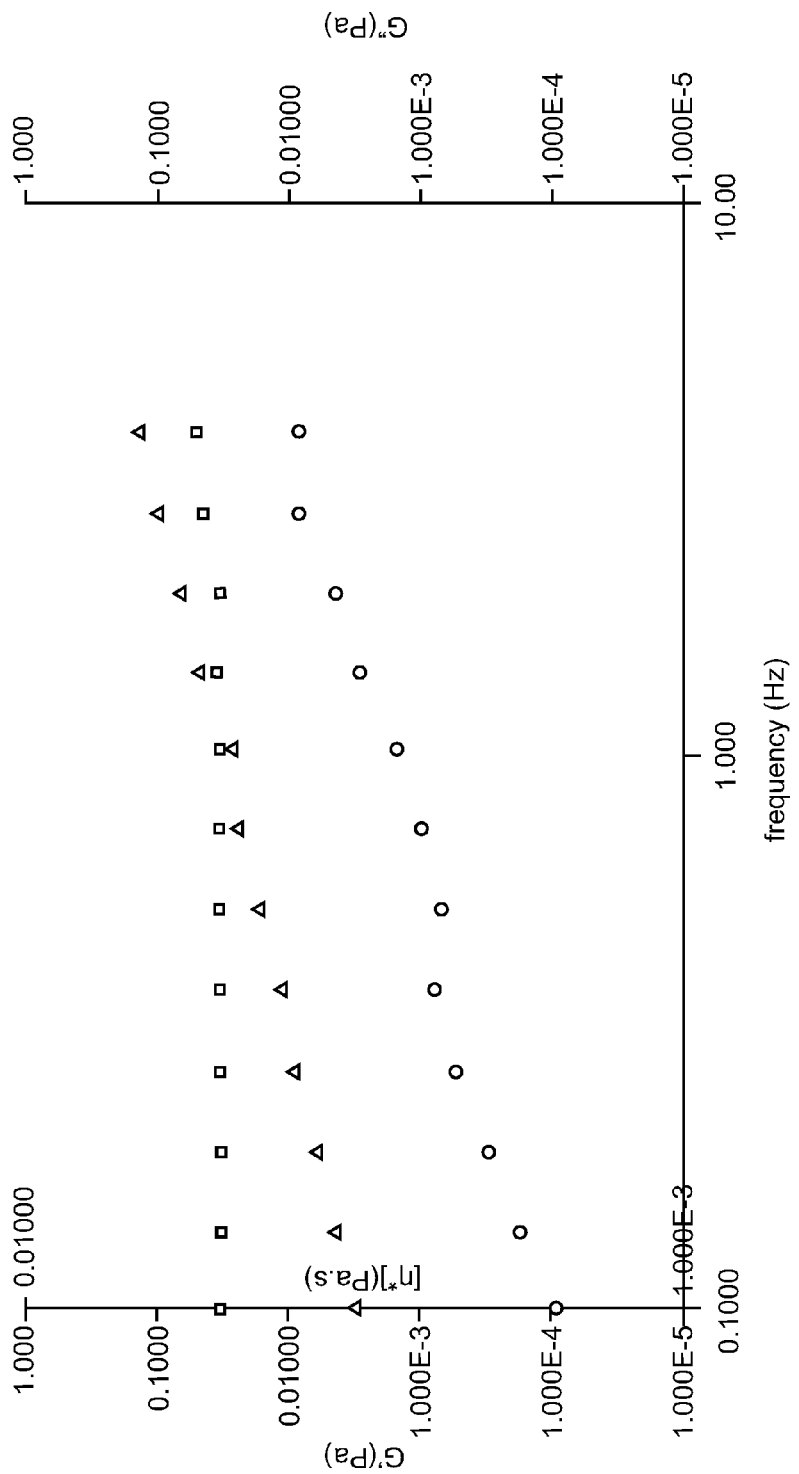
FIG. 25 illustrates a mechanical spectrum of an aqueous solution of 1.5% (w/v) alginate (Avg. Mw=30 kDa) mixed with 0.2% (w/v) calcium gluconate. circles=elastic response (G'); triangles=viscous response (G"); squares=complex viscosity.
Figure 26:
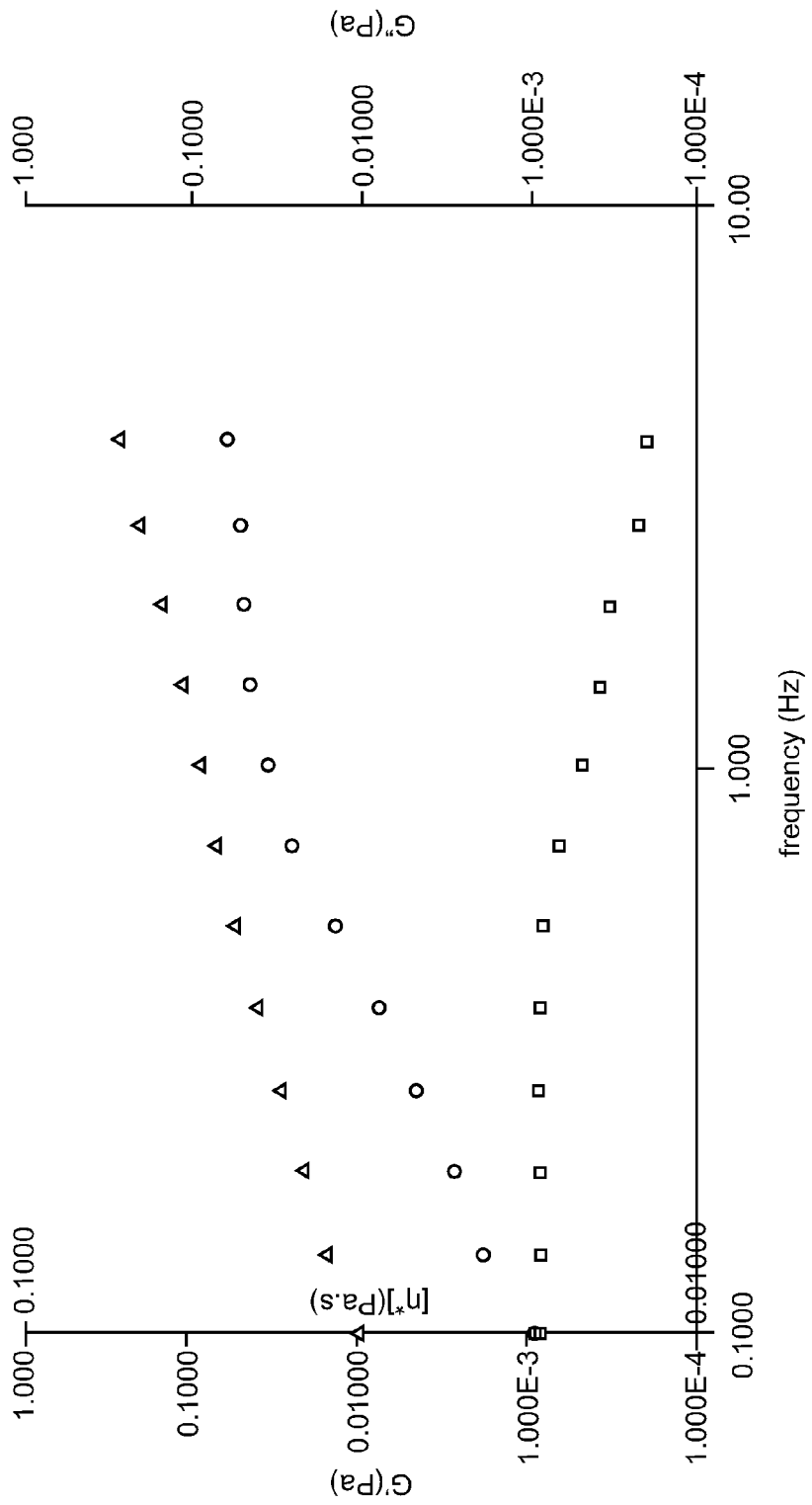
FIG. 26 illustrates a mechanical spectrum of an aqueous solution of 1.5% (w/v) alginate (Avg. Mw=30 kDa) mixed with 0.3% (w/v) calcium gluconate. circles=elastic response (G'); triangles=viscous response (G"); squares=complex viscosity.
Figure 27:
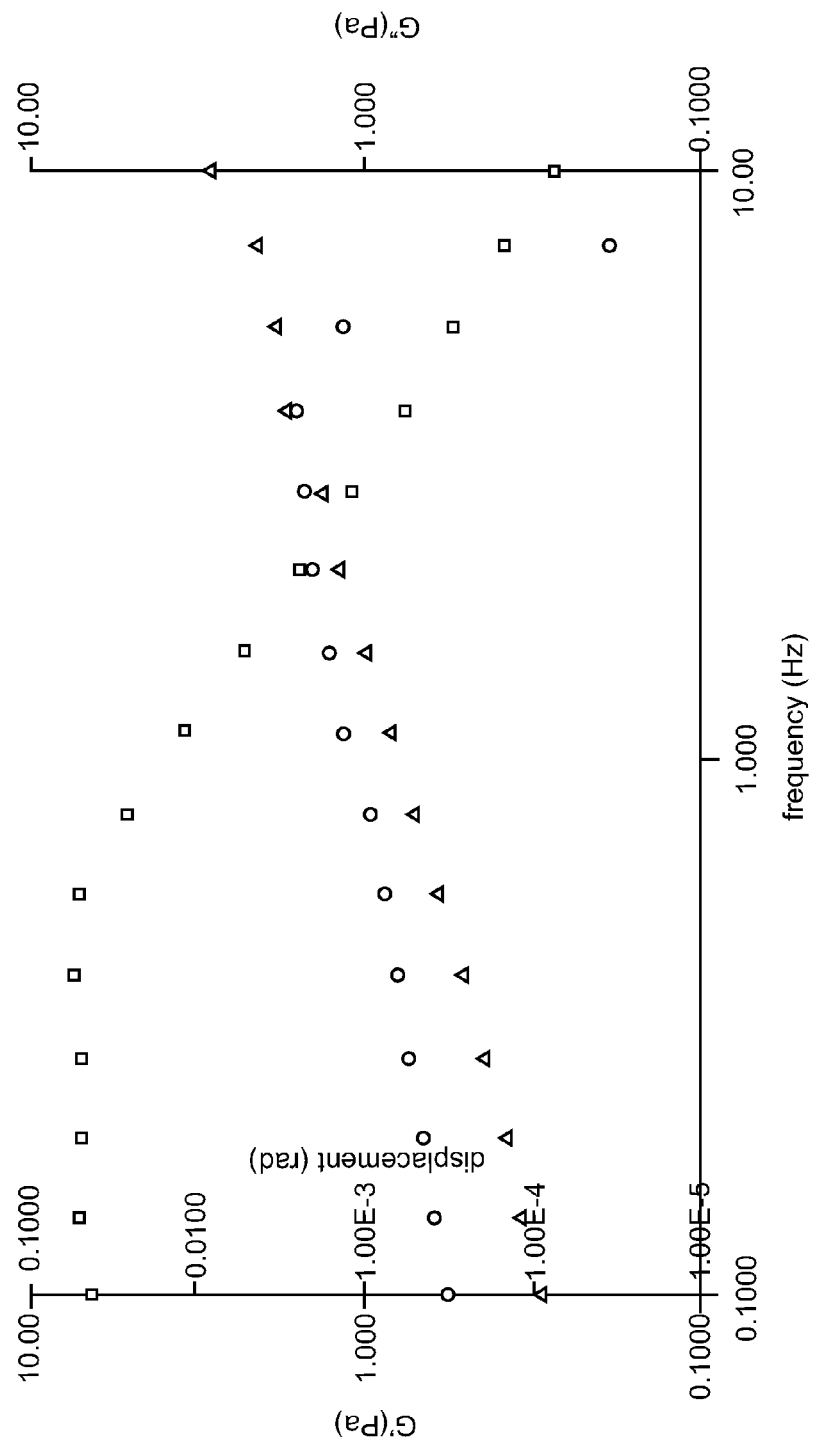
FIG. 27 illustrates a mechanical spectrum of an aqueous solution of 1.5% (w/v) alginate (Avg. Mw=30 kDa) mixed with 0.4% (w/v) calcium gluconate. circles=elastic response (G'); triangles=viscous response (G"); squares=complex viscosity.
Figure 28:
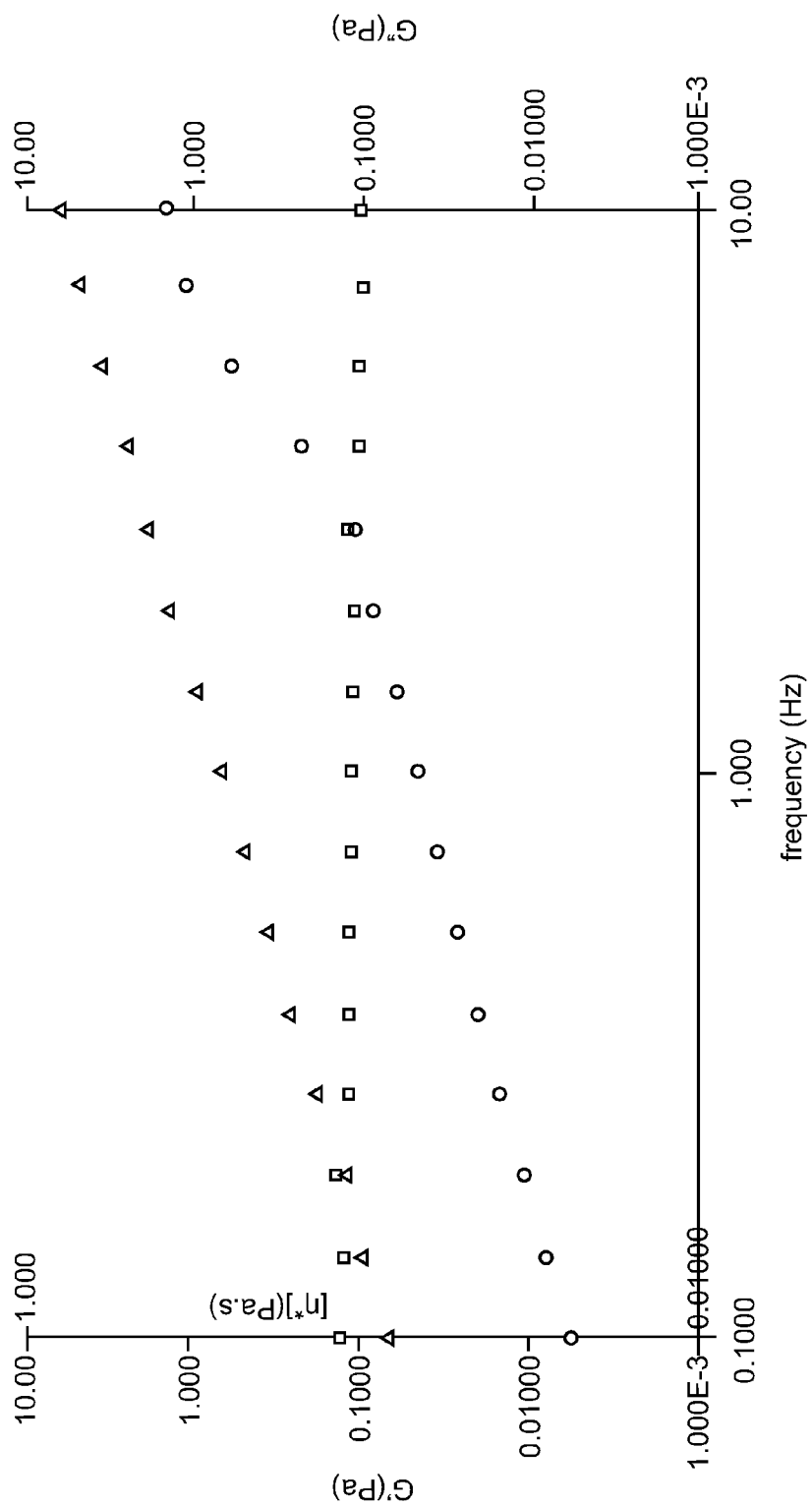
FIG. 28 illustrates a mechanical spectrum of an aqueous solution of 1% (w/v) alginate (Avg. Mw=160 kDa) with no calcium gluconate added. circles=elastic response (G'); triangles=viscous response (G"); squares=complex viscosity.
Figure 29:
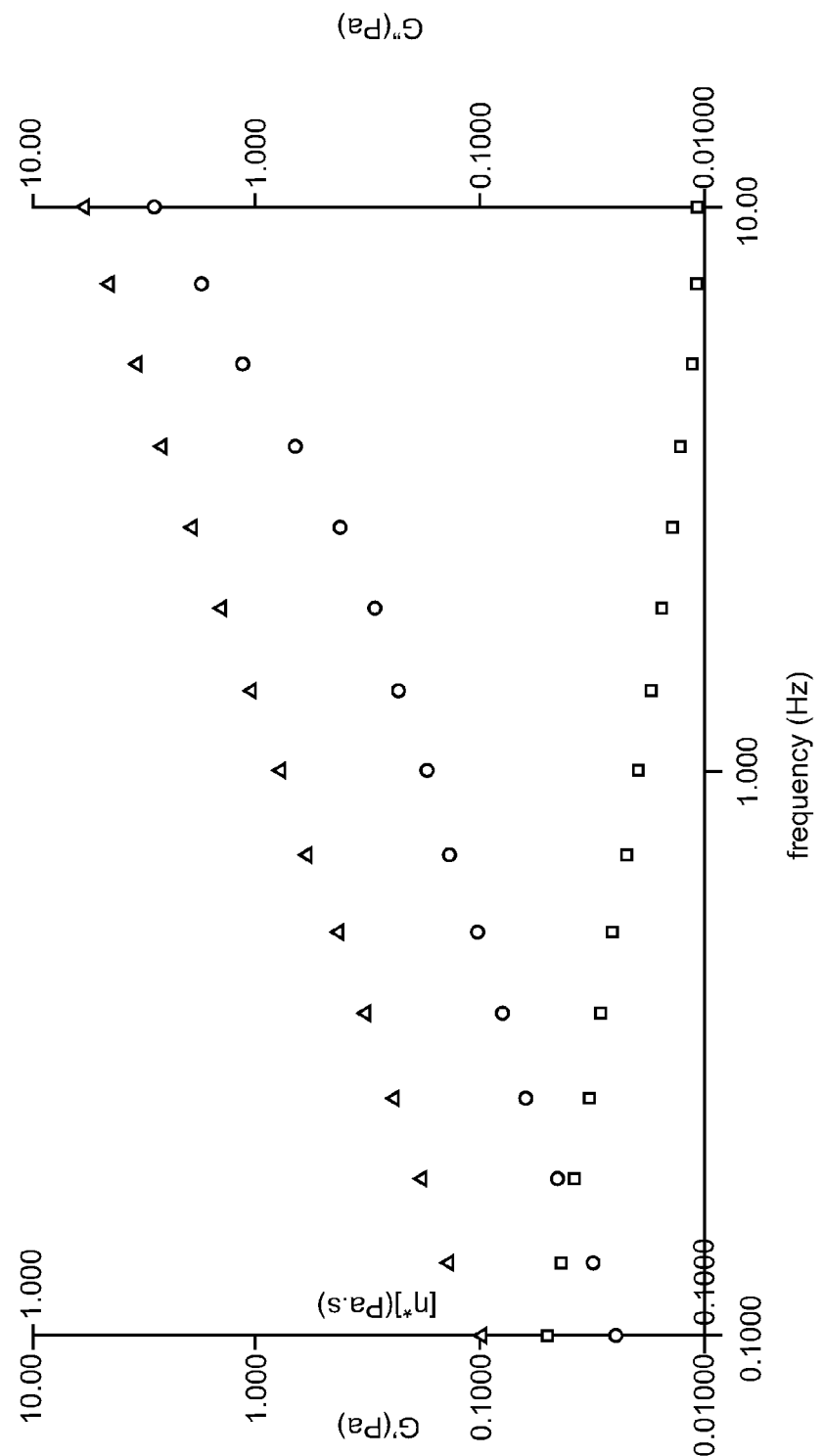
FIG. 29 illustrates a mechanical spectrum of an aqueous solution of 1% (w/v) alginate (Avg. Mw=160 kDa) mixed with 0.2% (w/v) calcium gluconate. circles=elastic response (G'); triangles=viscous response (G"); squares=complex viscosity.
Figure 30:
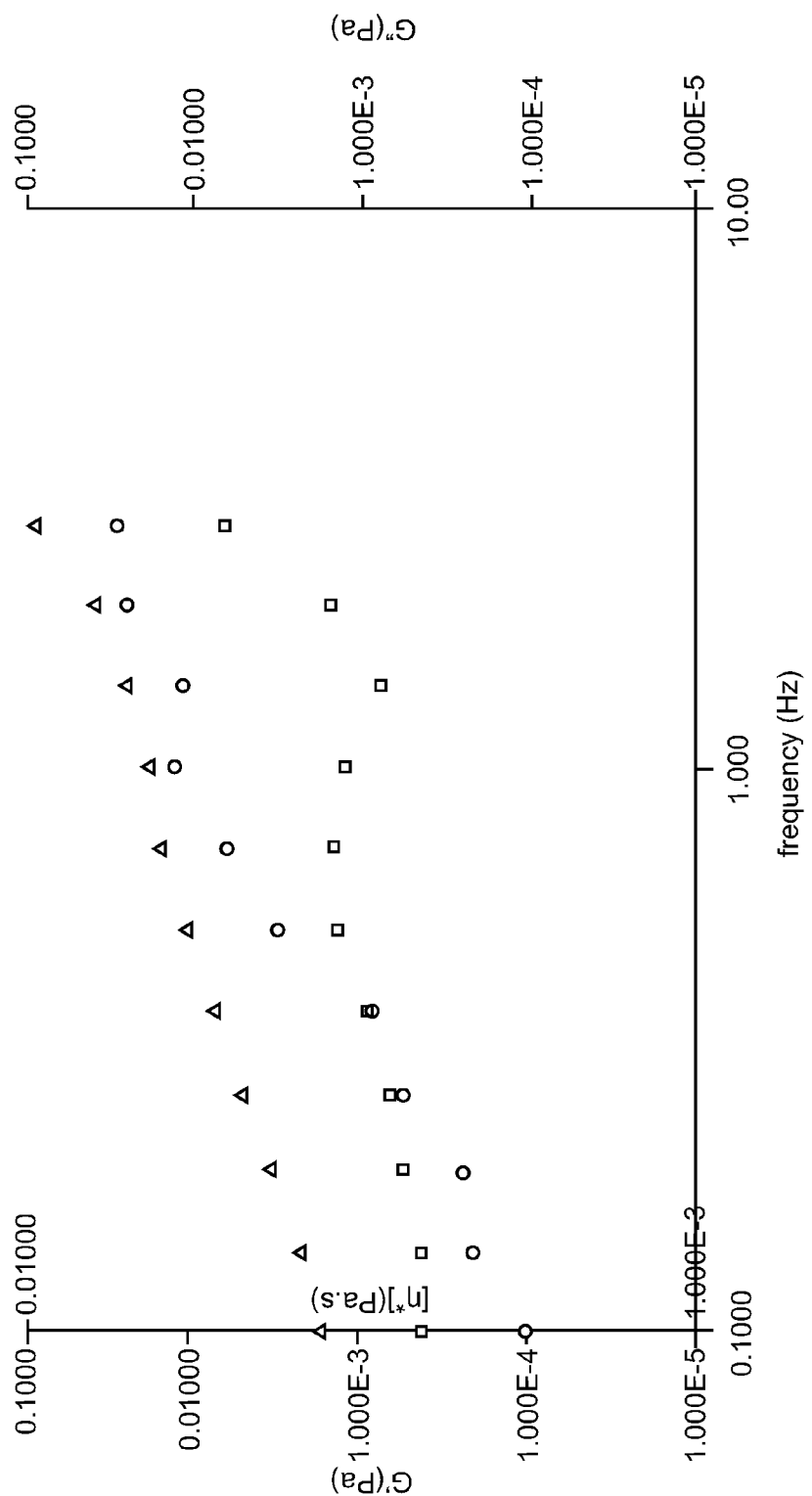
FIG. 30 illustrates a mechanical spectrum of an aqueous solution of 1% (w/v) alginate (Avg. Mw=15 kDa) with no calcium gluconate added. circles=elastic response (G'); triangles=viscous response (G"); squares=complex viscosity.
Figure 31:
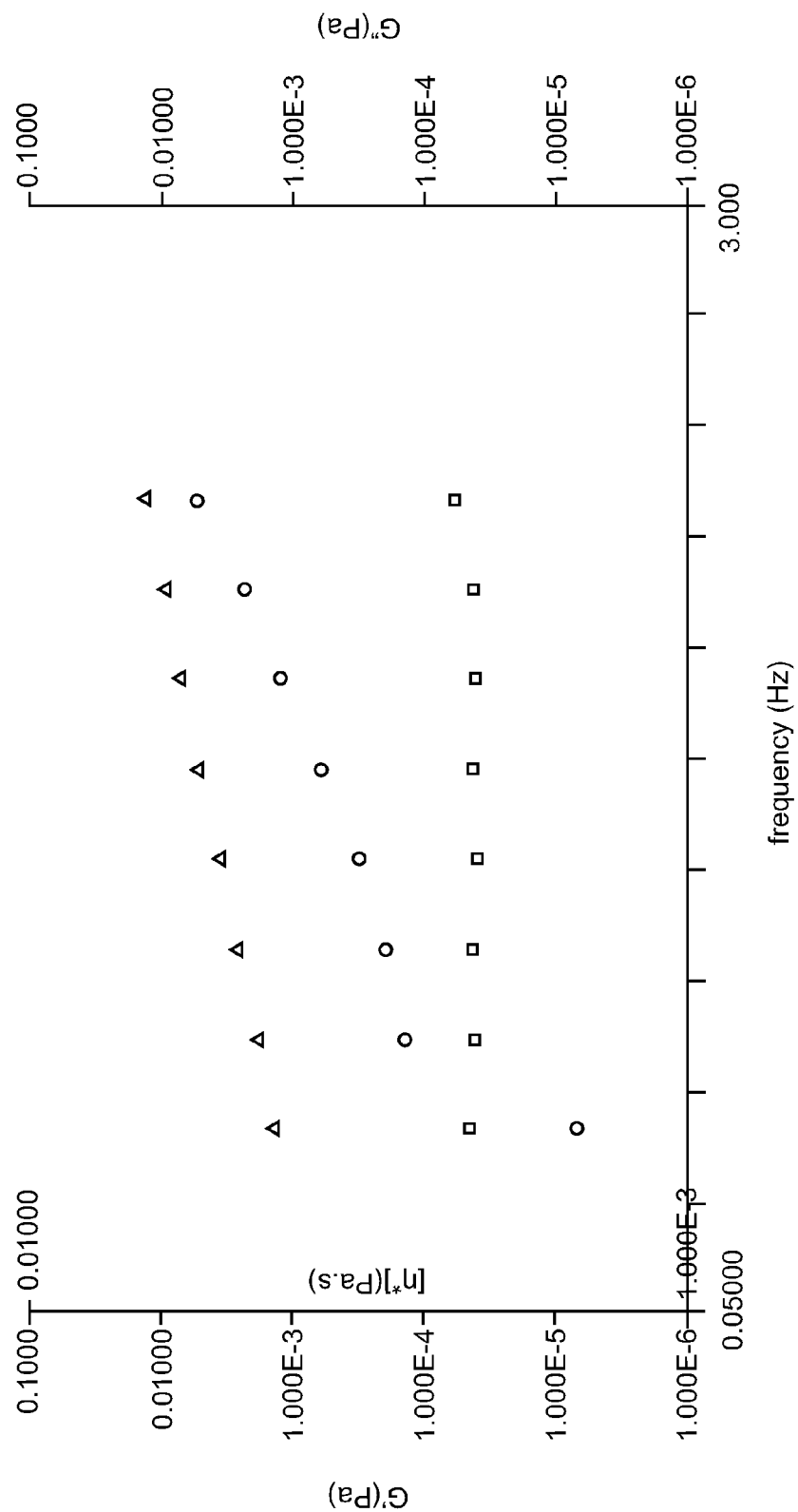
FIG. 31 illustrates a mechanical spectrum of an aqueous solution of 1% (w/v) alginate (Avg. Mw=15 kDa) mixed with 0.2% (w/v) calcium gluconate. circles=elastic response (G'); triangles=viscous response (G"); squares=complex viscosity.
Figure 32:
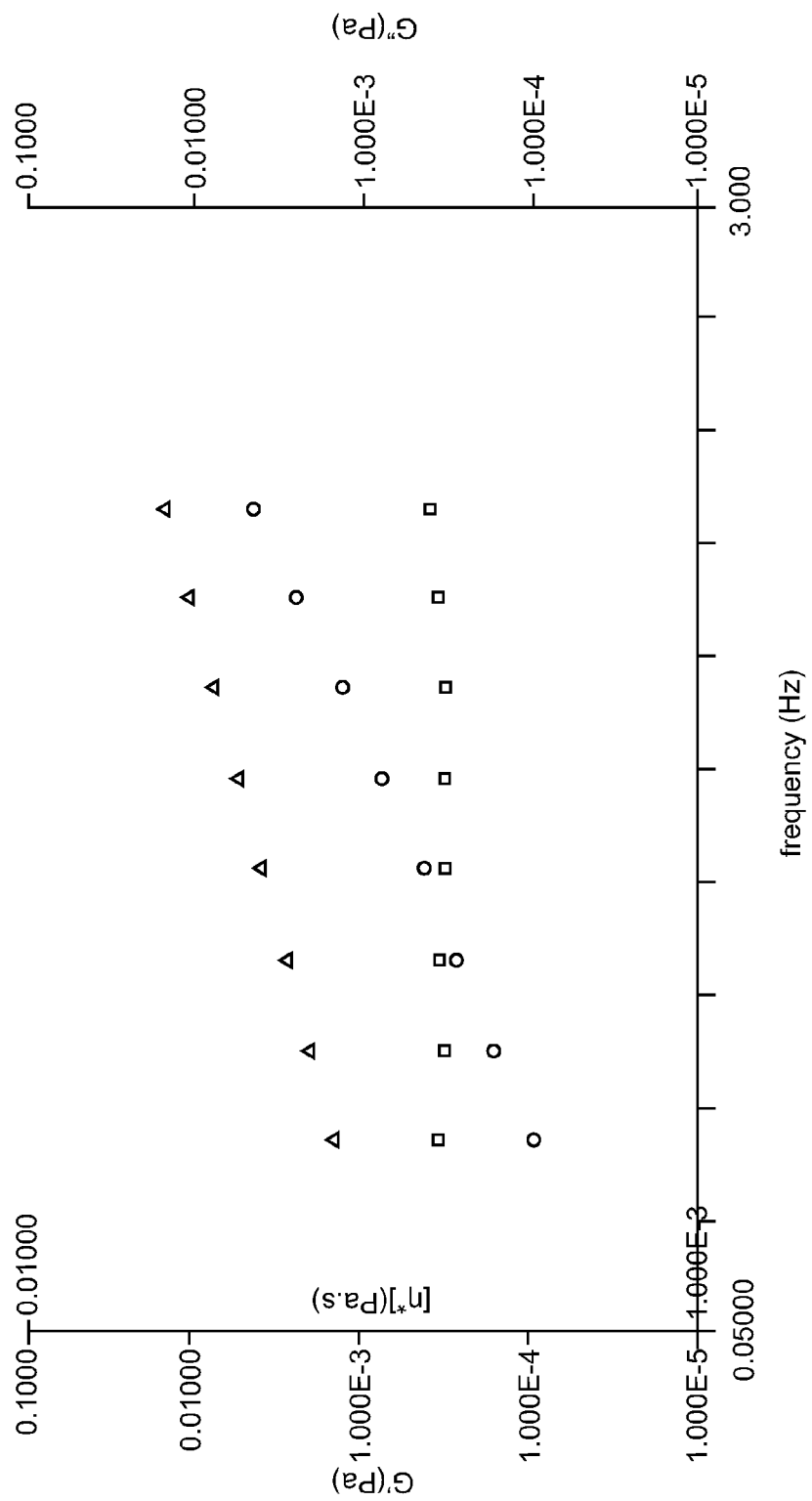
FIG. 32 illustrates a mechanical spectrum of an aqueous solution of 1% (w/v) alginate (Avg. Mw=15 kDa) mixed with 0.3% (w/v) calcium gluconate. circles=elastic response (G'); triangles=viscous response (G"); squares=complex viscosity.
Figure 33:
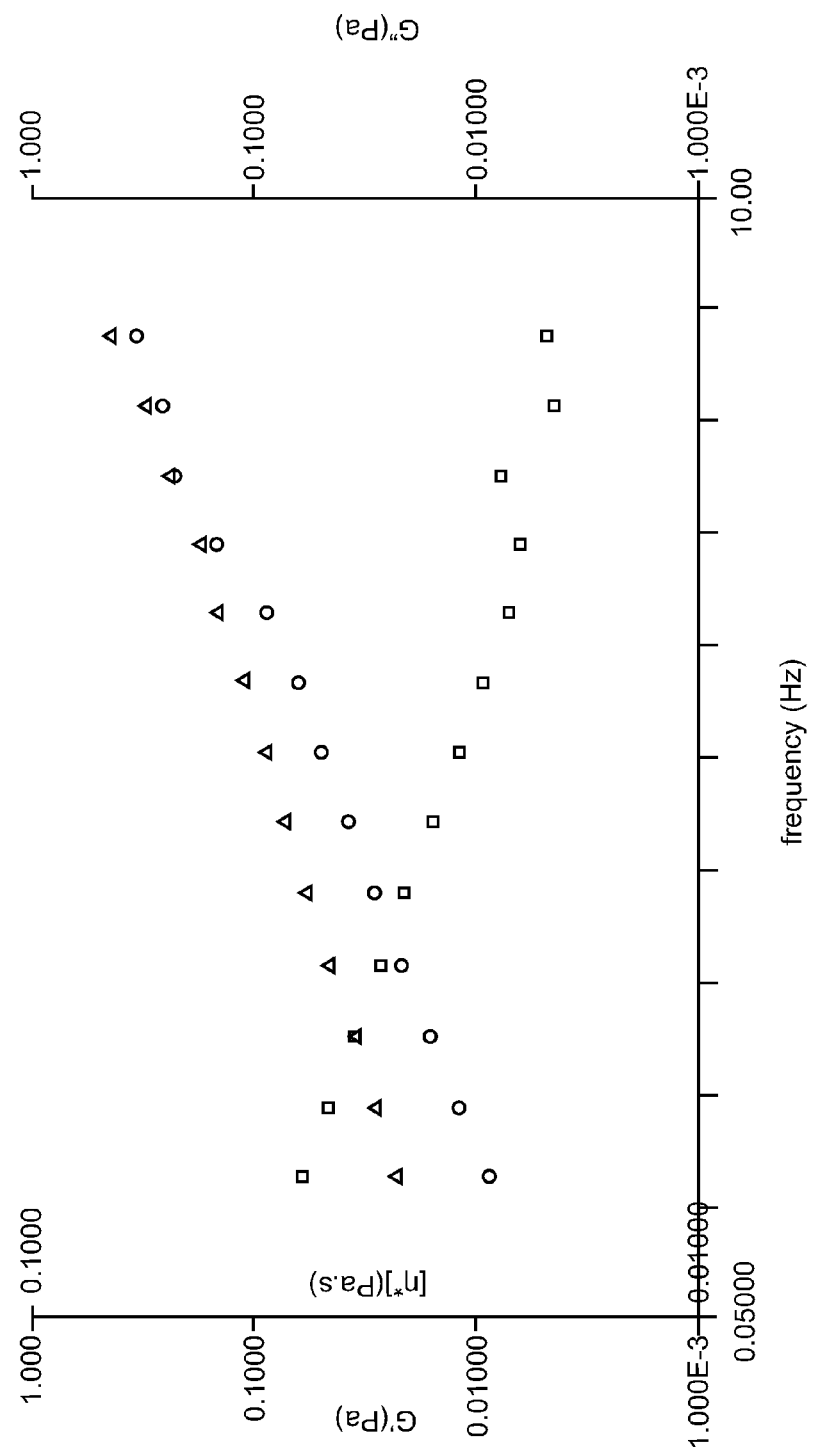
FIG. 33 illustrates a mechanical spectrum of an aqueous solution of 1% (w/v) alginate (Avg. Mw=15 kDa) mixed with 0.4% (w/v) calcium gluconate. circles=elastic response (G'); triangles=viscous response (G"); black squares=complex viscosity.

As illustrated in FIGS. 9A and B, treated myocardium which had circumflex occlusion exhibited repositioning of papillary muscles toward the anterior annulus. These observations show that providing the cross-linked alginate solution into the myocardium can reduce ischemic MR without compromising LV function.

Hence, these results indicate that the cross-linked alginate solution of the present invention can improve survival of pigs following MI and can promote regeneration of the damaged myocardia.

Example 4

Injection of Cross-Linked Alginate Solution Combined with Myoblasts into a Rat Normal Myocardium Materials and Methods:

Aqueous Cross-Linked Alginate Solution

The solution was made of 1% w/v sodium alginate (Avg. Mw=30 kDa; G/M ratio 2.1) and 0.3% w/v calcium gluconate, as described in Example 1 hereinabove.

Skeletal Myoblasts

Myoblasts from the hind limb muscle of Sprague-Dawley neonatal rats were isolated and purified according to the procedure described by Rosenblatt, J. D. (In Vitro Cell Dev. Biol. Anim. 31:773-779, 1995).

Animal Care

The study was performed in accordance with the guidelines of The Animal Care and Use Committee of Ben-Gurion University and Sheba Medical Center, Tel-Aviv University, which conforms to the policies of the American Heart Association and the "Guide for the Care and Use of Laboratory Animals" (Department of Health and Human Services, NIH Publication No. 85-23).

Injection

Male Sprague-Dawley rats (about 250 g) were anesthetized with a combination of 40 mg/kg ketamine and 10 mg/kg xylazine, intubated and mechanically ventilated. The rat chest was opened by left thoracotomy, the pericardium was removed and the rats were subjected to injection, using a 27-guage needle, with 100-200 µL of a suspension of skeletal myoblasts in the cross-linked alginate solution, or with a suspension of skeletal myoblasts in a serum free culture medium (control). Following injection, the surgical incision was sutured closed.

Histological and Immuno-Histological Examination

Four weeks following injection, animals were sacrificed with an overdose of phenobarbital. Hearts were harvested, and processed for histological examination. Adjacent blocks were embedded in paraffin, sectioned into 5 µm slices and stained with hematoxylin and eosin. Serial sections were immunolabelled with antibodies against fast MHC (Sigma).

Results:

Injection of skeletal myoblasts combined with cross-linked alginate solution neoangiogenesis and neovascularization, as shown by the formation of functional new vessels, which can be evidenced by the presence of red blood cells. Furthermore, the treatment substantially increased the retention of transplanted myoblasts at the injection site, as compared with the control.

Example 5

Injection of Cross-Linked Alginate Solution Combined with Human Blood-Derived Progenitor Cells into a Rat Infarcted Myocardium Materials and Methods:

Aqueous Cross-Linked Alginate Solution

The solution was made of 1% w/v sodium alginate (Avg. Mw=30 kDa; G/M ratio 2.1) and 0.3% w/v calcium gluconate, as described in Example 1 hereinabove.

Animal Care

The study was performed in accordance with the guidelines of The Animal Care and Use Committee of Ben-Gurion University and Sheba Medical Center, Tel-Aviv University, which conforms to the policies of the American Heart Association and the "Guide for the Care and Use of Laboratory Animals" (Department of Health and Human Services, NIH Publication No. 85-23).

Induction of Myocardial Infarction

Athymic nude rats (about 250 g) were anesthetized using a mixture of 40 mg/kg ketamine and 10 mg/kg xylazine, then intubated and mechanically ventilated. The animal chest was opened using left thoracotomy, the pericardium was removed and the proximal left coronary artery permanently occluded with an intramural stitch.

Injection of the Cross-Linked Alginate Solution

One week post MI animals chest was opened and the infarcted area was identified visually on the basis of surface scar and wall motion akinesis. Aqueous cross-linked alginate solution (100-200 µL), or a serum free culture medium (control) was injected into the myocardial scar tissue using a 27-guage needle. Following injection the surgical incision was sutured closed.

Infusion of Human Blood-Derived Progenitor Cells

One week following injection animals were treated with intravenous infusion of human blood-derived $CD133^+$ progenitor cells ($2-4\times10^6$ cells).

Histological and Immuno-Histological Examination

One week following infusion animals were sacrificed by administering an overdose of phenobarbital. Hearts were harvested and processed for histological examination. The presence of human donor cells in recipient rat myocardium was confirmed by immunostaining using anti-HLA-DR antibodies.

Results:

Infused donor cells (highlighted brown color) colonized the scar tissue at site of injection of the cross-linked alginate solution. These histological observations indicate that the cross-linked alginate solution is capable of effectively promoting homing of stem or progenitor cells to the injected site.

Example 6

Intra-Coronary Administration of Cross-Linked Alginate Solution to Pig Infarcted Myocardium Materials and Methods:

Preparation of Biotinylated Alginate

Sodium alginate solution (2% w/v; Avg. Mw=30 kDa; G/M ratio 2.1) was diluted in an equal volume of 1 M 2-[N-morpholino]ethansulfonicacid monohydrate (MES) buffer at pH 6.0 [resulting in 1% (w/v) alginate in 0.5 M MES]. Biotin hydrazide (0.052 g; 0.2 mmol) was added to the alginate solution (5 ml) and the mixture was stirred to yield a stable suspension. The suspension was then supplemented with N-hydroxysulfosuccinimide (NHSS; 0.0217 g; 0.1 mmol)) and 1-ethyl-3-(dimethyaminopropyl) carbodiimide HCl (EDAC; 0.0384 g; 0.2 mmol) and stirred at room temperature for 2 hr. The resulting product was dialyzed against 2 liter DDW using 8000 MWCO membrane (water was changed twice a day for two days) then lyophilized.

Aqueous Cross-Linked Alginate Solution

The cross-linked alginate solution was made of biotinylated or non-biotinylated sodium alginate (1% w/v; Avg. Mw=30 kDa; G/M ratio 2.1) and calcium gluconate (0.3% w/v) using the procedure described in Example 1 hereinabove.

Animal Care

The study was performed in accordance with the guidelines of The Animal Care and Use Committee of Ben-Gurion University and Sheba Medical Center, Tel-Aviv University, which conforms to the policies of the American Heart Association and the "Guide for the Care and Use of Laboratory Animals" (Department of Health and Human Services, NIH Publication No. 85-23).

Induction of Myocardial Infarction (MI)

Myocardial infarction was induced according to Yau et al. (Ann Thorac Surg 75:169-176, 2003) and Watanabe et al. (Cell Transplant 7:239-246, 1998). Briefly, female domestic pigs weighing 50-75 kg were intramuscularly pre-medicated with ketamine (20 to 30 mg/kg), then anesthetized using 4% isoflurane. Anesthesia was maintained with isoflurane 1% to 2.5%. MI was induced via cardiac catheterization and inflation of coronary angioplasty balloon in the left anterior descending (LAD) coronary artery (beyond the first diagonal branch to occlude LAD flow) for 60 or 90 minutes. This occlusion resulted in myocardial infarction in the left ventricle which was confirmed by angiography, electrocardiography and echocardiography analyses. Severe ventricular arrhythmias appearing during occlusion were treated by intravenous administration of amiodarone or lidocaine. Following occlusion, animals were administered intravenously with heparin (5,000 UI) and aspirin (250 mg) then allowed to recover. Analgesics were administered intramuscularly for pain control. Antibiotics were given as necessary.

Intra-Coronary Administration of the Cross-Linked Alginate Solution

Four days following MI an over-the-wire balloon catheter oversized by 0.5 mm was advanced into the LAD coronary artery to the location of prior occlusion. The cross-linked alginate solution (2 ml) was infused distally to the occluding balloon, through the central port of the balloon catheter, during intermittent coronary occlusions, each lasting 2.5-4 min. The coronary artery was re-perfused for about 3 min between occlusions. Upon completion of intra-coronary administration, coronary angiography was repeated to ascertain vessel potency and unimpeded flow of contrast material. Serum troponin I levels were measured prior to and 24 hr following intra-coronary administration.

Echocardiography

Echocardiogram analyses were performed immediately following MI prior to injection treatment, as well as on day 10, 30 and 60 post MI. The analyses were performed using a phased-array transducer (2.5 MHz) equipped with an ultrasound system (Sonos 5500, Hewlett-Packard, Andover, Mass.). Images were recorded on VHS videotape. End-diastolic and end-systolic frames were selected from standard apical and parasternal views.

Global LV ejection fractions (LVEF) were assessed visually. LV volumes were measured by manually tracing the left ventricular cavity using the single plane modified Simpson's algorithm when >80% of the endocardial border could be detected in both the apical 4- and 2-chamber views, and by a single plane when 80% of the endocardial border could be detected only in the apical 4-chamber view.

Regional wall motion and regional LV function of each of the 16 left ventricular segments were assessed using score values (1=normal, 2=hypokinetic, 3=akinetic, 4=dyskinetic) according to Schiller et al. (J. Am. Soc. Echocardiogr. 2:358-67 1989). Left ventricular wall motion score index (WMSI) values were calculated using the sum of the individual scores divided by the total number of analyzed segments. Regional motion score index were calculated by the same method for the segments of the mid-LAD territory (infarct related artery territory).

In the four-chamber view, pulsed Doppler transmitral flow velocities were recorded by positioning the sample volume both at the level of the tip of the mitral valve leaflets and the mitral valve annulus. At the level of the tip of the mitral valve, time periods were measured between the peak of the ECG R-wave to the beginning, peak and end of the components of the transmitral flow velocity pattern, as well as the time periods to the E-wave (early diastolic filling) and A-wave (late diastolic filling). The acceleration and deceleration time periods of the E-wave were also measured. The deceleration time were calculated by extrapolating the deceleration slope to the baseline. At the level of the mitral valve annulus, diastolic filling time was determined as the duration of mitral flow. The flow during the E-wave and A-wave was calculated by planimetry of each velocity curve. Each value was determined as the mean measurement of three consecutive steady-state beats. The occurrence of mitral regurgitation during ischemia was monitored using two-D color flow. The data were interpreted by a single experienced observer (MSF), and all measurements were obtained off line by a single technician.

SPECT Imaging

SPECT imaging was performed using conventional techniques using technetium-99m sestamibi. Standard SPECT myocardial scintigrams.

Imaging protocol: One hour after intravenous administration of $^{99m}$Tc-sestamibi (25 to 30 mCi), electrocardiogram-gated single-photon emission computed tomography imaging were performed. All animals were imaged in the supine position. The radionuclide images were acquired based on our clinical protocol with 64 angular views over 180° (from 45° right anterior oblique to 135° left posterior oblique) using a 128×128 matrix, 20 s per view, a 20% energy window centered at 140 keV and a low-energy, high-resolution (LEHR) collimator. Using a two-head gamma camera, the total data acquisition time were approximately 12 min.

Semi-quantitative analysis: Images were evaluated in a blinded fashion by two nuclear cardiologists using a standard 20-segment analysis (18 short-axis and 2 long-axis segments). Each segment was scored on a 5-point scale of 0 to 4 (0=normal perfusion, 1=mild hypoperfusion, 2=moderate hypoperfusion, 3=severe hypoperfusion and 4=no perfusion). A sum rest score was calculated for each animal. A semi-quantitative change score was calculated as the mean difference between the rest score from the day 90 scan and the rest score of the same animal on day 0. LV regional wall motion was evaluated from the gated study using a similar standard 20-segment analysis (18 short-axis and 2 long-axis segments). Each segment were scored on a 5-point scale of −1 to 3 (−1=dyskinesis, 0=akinesis, 1=moderate/severe hypokinesis, 2=mild hypokinesis and 3=normokinesis).

Quantitative analysis: Quantitative computer analysis was performed using QPS software (Cedars Sinai, LA, Calif.). The software consists of an automatic program, capable of batch processing, which, among various calculations on cardiac single-photon emission computerized tomography perfusion images, performs automatic scoring of these images. The algorithm is independent of myocardial shape, size, and orientation, and establishes a standard three-dimensional point-to-point correspondence among all sampled myocardial segments. Percent change in summed rest scores were calculated as: {[(mean score day 90)−(mean score of day 0)]/(mean score of day 0)}*100.

MRI

ECG-gated cardiac MRI was performed using a Sigma MR/i, 1.5 T EchoSpeed Plus MRI scanner (General Electric Medical Systems, Waukesha, Wis.). Cine MRI images were acquired, using a steady-state cine-MRI technique (Fast Imaging Employing STeady-state Acquisition, FIESTA) acquired in short-axis oblique (SAO), vertical long-axis oblique (LAO) and axial 4-chamber view. This was followed by perfusion and delayed enhancement analyses. Perfusion analyses were performed during intravenous injection (10 ml) of gadopentate dimeglumine (Omniscan, 0.5 mmol/ml, Nycomed Imaging AS, Oslo, Norway) at a rate of 4 ml/sec, using an automatic injector (Medrad Spectris, Indianola, Pa., USA). Delayed enhancement images were obtained following an additional injection of gadopentate dimeglumine (0.2 mmol/kg up to a maximum of 20 ml) using inversion recovery prepared breath-hold cine gradient-echo images. LAO and SAO views were obtained 15 and 20 min following gadolinium injection, respectively.

Image analysis: The left and right ventricular end diastolic volume and the left/right ventricular ejection fraction were calculated from cine-MRI images by an experienced radiologist blinded to other imaging findings. The calculations were performed using an Advantage Windows Workstation (Rev 4.1, GE, Buc France) and Mass Analysis software (MEDIS, Netherlands).

The Extent of myocardial infarction was estimated using a the standard 16 segments (Schiller et al., J. Am. Soc. Echocardiogr. 2:358-67 1989) and a three-scale scoring index (0=no evidence of infarction, 1=subendocardial infarction, 2=transmural infarction).

Morphological and Histological Examination

Animal hearts were arrested by potassium chloride and rapidly excised.

Coronary arteries were perfused with 100 mL 10% formaldehyde and the hearts were the fixed in diastole with an intraventricular pressure of 30 mm Hg in formaldehyde solution. Following fixation, the heart tissue was dissected (5 μm thick), embedded in paraffin blocks at 56° C. and stained with hematoxylin and eosin for histological examination.

The presence and distribution of biotinylated alginate within myocardial tissue was detected using enzyme (peroxidase)-linked avidin. Accordingly, tissue samples were serially rehydrated in 100%, 95%, and 70% ethanol following by deparaffinization with toluene. Endogenous peroxidase was then blocked (using methanol, $H_2O_2$ and $H_2O$) and the tissue was exposed to peroxidase-linked avidin complex (Vector Laboratories) then counterstained with hematoxylin. Positive biotin-avidin interaction resulted in brown color which highlighted the biotinylated alginate material.

Results:

Nine pigs were used overall, out of which one animal (pig No. 6) died during anesthesia prior to MI. Another animal (pig No. 9), which was subjected to 90 min occlusion, developed an extensive heart failure and died five hr following injection (see Table 6 hereinbelow).

Echocardiography, SPECT imaging and MRI analyses did not detect any significant cardiac malfunction, arrhythmias, ventricular tachycardia, fibrillation or premature ventricular contractions, in any of the treated animals during the observation period (between intra coronary administration and harvest; up to 5 days).

TABLE 6

Summary of treatments and function analyses

| Pig No. | Occlusion Time (Min) | Intra coronary administered material | Echo | SPECT | MRI | Observation period[3] | Comments |
|---|---|---|---|---|---|---|---|
| 1 | 60 | Alginate-Biotin[1] | + | | | 1 hr | |
| 2 | 60 | Alginate[2] | | | | 5 days | |
| 3 | 60 | saline | + | | | 5 days | |
| 4 | 60 | Alginate | + | | | 1 hr | |
| 5 | 60 | Alginate | + | | | 1 hr | |
| 6 | n/a | n/a | | | | n/a | Animal died prior to MI |
| 7 | 60 | Alginate-Biotin | + | + | + | 1 hr | |
| 8 | 90 | Alginate-Biotin | + | | | 1 hr | |
| 9 | 90 | Alginate | + | | | 1 day | Animal died 5 hr following IC administration |

[1]Alginate-Biotin = biotin-labeled cross-linked alginate solution.
[2]Alginate = cross-linked alginate solution only.
[3]The time period between IC administration to harvest.

Morphological and Histological Examinations

Upon visual inspection, transient occlusion of the mid LAD coronary artery caused significant infarction (ca. 25% of the left ventricle with 60 min occlusion) at the anterior, apical, septal and right ventricular apex.

Morphological examinations revealed abundance of gelatinous cross-linked alginate (biotinylated) present within ischemic myocardial tissue (seen as pale white substance. The morphological observations correlated with SPEC and MRI imaging analyses.

Histological examinations revealed brown stained tissue indicating extensive spread of the biotinylated cross-linked alginate within the extracellular matrix of the infarcted myocardium tissue. In addition, the cross-linked alginate material was observed in association with dividing cardiomyocytes (noticeable by having multiple nuclei) indicating that the cross-linked alginate solution may promote myocardial tissue regeneration.

These results clearly show that the cross-linked alginate solution can be administered into a blood vessel via catheterization and capable of flow within blood vessels, cross blood capillary walls, spread throughout the extracellular matrix of target tissue and assume a gel state following deposition within the tissue.

Hence, the results indicate that the cross-linked alginate solution can be delivered into a damaged myocardial tissue via intra coronary administration effectively, conveniently and safely.

Example 7

Injection of Cross-Linked Alginate Solution into Mouse Ischemic Hind Limb

Materials and Methods:
Aqueous Cross-Linked Alginate Solution

The cross-linked alginate solution was made of 1% w/v sodium alginate (Avg. Mw=30 kDa; G/M ratio 2.1) and 0.3% w/v calcium gluconate, as described in Example 1 hereinabove.

Animal Care

The study was performed in accordance with the guidelines of The Animal Care and Use Committee of Ben-Gurion University and Sheba Medical Center, Tel-Aviv University, which conforms to the policies of the American Heart Association and the "Guide for the Care and Use of Laboratory Animals" (Department of Health and Human Services, NIH Publication No. 85-23).

Mouse Hind Limb Model

A mouse hind limb ischemia model was established essentially as described by Couffinhal et al. (American Journal of Pathology 152:1667-1679, 1998) and Babiak et al. (Cardiovasc Res. 61:789-795, 2004). Twelve wk old Balb/C mice weighting between 26 and 30 g were used. Under short-term anaesthesia, the left femoral artery were exposed, dissected free, and excise according to Madeddu et al. (Faseb. J. 18:137-139, 2004). The experimental setting was intended to mimic the clinical situation of patients with extensive, acute arterial occlusion.

Administration of Cross-Linked Alginate Solution

Cross-linked alginate solution (0.05 ml) was injected intramuscularly to the ischemic hind legs of treated mice one day following femoral artery excision. Untreated (control) mice were injected with PBS.

In Vivo Perfusion Analysis

Perfusion analysis was performed following femoral artery ligation, prior to and 7 days following injection. Quantitative perfusion imaging were performed via i.v. injection of Hexakis-(2-methoxyisobutylisonitrile)-technetium-99m (Tc-99m-MIBI; Cardiolite®, Dupont Pharma) and a lipophilic perfusion marker (bolus of 200 l containing a dose of 50-60 MBq). Data quantification was performed using a gamma camera (Basicam®, Siemens, using the ICON software package).

Statistical Analysis

All values are presented as mean ? SE. Changes in values measured in the same animal during different periods were analyzed by paired t test using GraphPad Prism version 4.00 for Windows (GraphPad Software, San Diego Calif. USA). Differences between the cross-linked alginate injected (treated) and the PBS injected (control) groups were analyzed by unpaired t test. All tests were two-tailed and p<0.05 was considered statistically significant.

Figure 34:
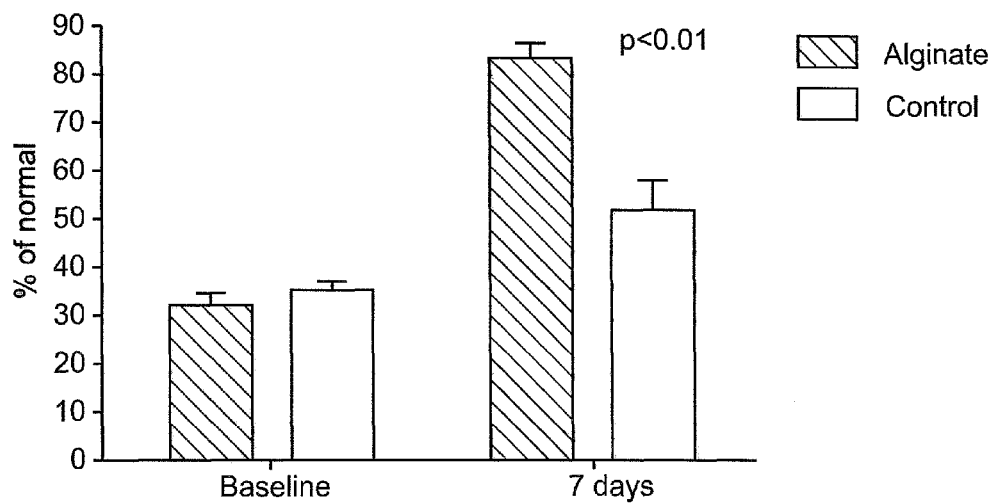
FIG. 34 illustrates the effect of injecting the cross-linked alginate solution (alginate) or PBS (control) into a mouse ischemic hind limb, on the blood flow rate in the damaged tissue. Relative blood flow rates were measured prior to injection and 7 days following injection.
Figure 35:
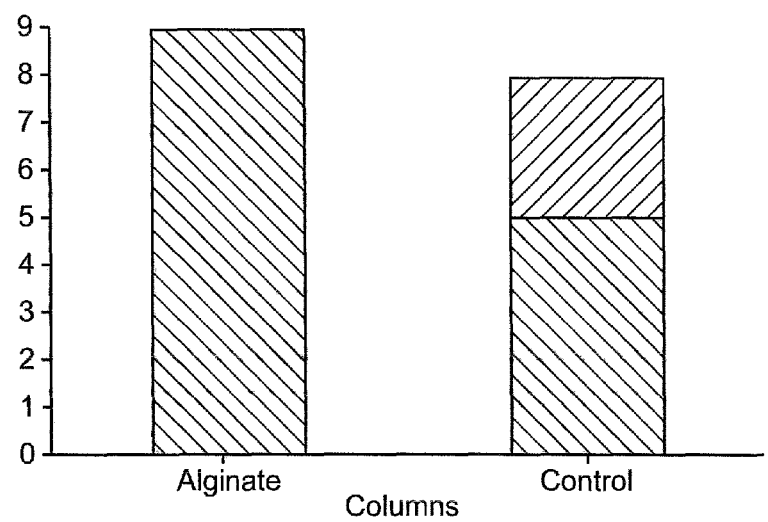
FIG. 35 illustrates the effect of injecting the cross-linked alginate solution (alginate) or PBS (control) into a mouse ischemic hind limb on the limb survival. In the control group 3 out of 8 animals developed necrosis and subsequently fell off (left cross-hatching), while none of the alginate-treated limbs were lost.
Figure 36:
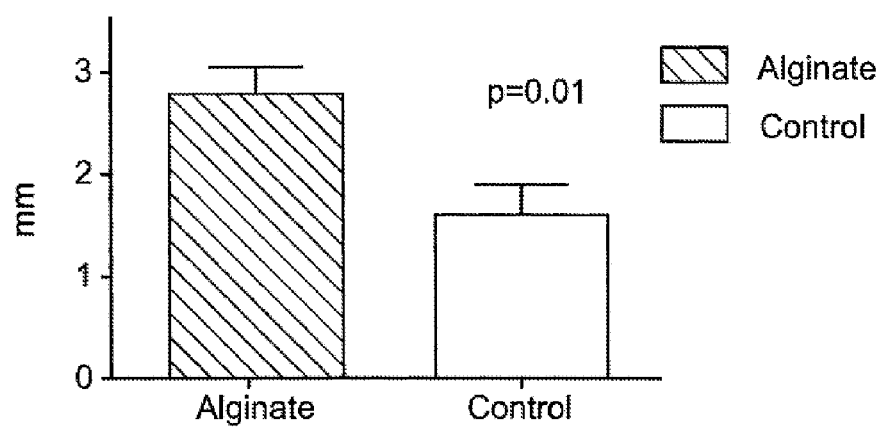
FIG. 36 illustrates the effect of the cross-linked alginate solution injected into a rat myocardium two months post MI, on the average myocardial scar thickness measured four months post MI. The average scar thickness in the alginate-treated animals was 27.9±2.7 mm, compared with just 16.3±3.1 in the PBS-treated (control) animals (p<0.05)

Results:

Administration of cross-linked alginate solution into mouse ischemic hind limbs significantly increased blood perfusion in the treated limbs, as compared with the control (FIG. 34; p<0.01). In addition, the cross-linked alginate solution effectively protected the ischemic limbs from autoamputation, as compared with the control where 3 out of 8 the ischemic limbs developed necrosis and were subsequently lost (FIG. 35).

Hence, the results clearly indicate that cross-linked alginate solution can be used to repair ischemic muscle tissues.

Example 8

Injection of Cross-Linked Alginate Solution into a Rat Chronically Damaged Myocardium Materials and Methods:

Aqueous Cross-Linked Alginate Solution

The cross-linked alginate solution was made of 1% w/v sodium alginate (Avg. Mw=30 kDa; G/M ratio 2.1) and 0.3% w/v calcium gluconate, as described in Example 1 hereinabove.

Animal Care

The study was performed in accordance with the guidelines of The Animal Care and Use Committee of Ben-Gurion University and Sheba Medical Center, Tel-Aviv University, which conforms to the policies of the American Heart Association and the "Guide for the Care and Use of Laboratory Animals" (Department of Health and Human Services, NIH Publication No. 85-23).

Induction of Myocardial Infarction

Forty rats were subjected to myocardial infarction using the procedure as described in Example 2 hereinabove.

Injection of the Cross-Linked Alginate Solution

Two months following MI, 27 animals which survived were randomized and injected with cross-linked alginate solution (treatment group) or with PBS (control group). For injection, animals were anesthetized and their chest was opened under sterile conditions. The infarcted area was identified based on the appearance of surface scar and wall motion akinesis. The scar tissue was then injected, using a 27-guage needle, with 100-200 μL of the aqueous cross-linked alginate solution, or PBS (control). Following injection, the surgical incision was sutured closed.

Echocardiography

Transthoracic echocardiography was performed on all animals within 24 hours post MI (baseline echocardiogram) and two months post injection using the procedure essentially as described by Etzion et al. (J. Mol. Cell. Cardiol. 33: 1321-1330, 2001) and Leor et al. (Circulation 102:III56-61, 2000). The measured parameters were: LV anterior wall thickness; maximal LV end-diastolic dimension; minimal left ventricular end-systolic dimension in M-mode and 2-D imaging; and fractional shortening (as a measure of systolic function) calculated as [FS (%)=(LVIDd−LVIDs)/LVIDd×100], where LVID indicates LV internal dimension, s is systole, and d is diastole. Index of change in LV area (%) was calculated as [(EDA−ESA)/EDA]×100 where EDA indicates LV end diastolic area, ESA indicates LV end systolic area (Mehta et al., J. Am. Coll. Cardiol. 11:630-636, 1988). All measurements were averaged for three consecutive cardiac cycles.

Morphological and Histological Examination

Two months following injection (four months following MI), animals were sacrificed with an overdose of phenobarbital. Hearts were harvested, sectioned into 5 μm slices and stained with hematoxylin and eosin for histological examination.

Angiogenesis Assessment

Angiogenesis was assessed by immunohistologic staining of tissue sections with anti α-actin smooth antibody (Sigma) using the procedure described by Leor et al. (Circulation; 94:II332-336, 1996). Following preliminary microscopic examination under low power, five consecutive adjacent fields were photographed from each section at a magnification of ×200. The density of blood vessels was estimated using computerized image analysis.

Statistical Analysis

All values are presented as mean ? SE. Changes in values measured in the same animal during different periods were analyzed by paired t test using GraphPad Prism version 4.00 for Windows (GraphPad Software, San Diego Calif. USA). Differences between the cross-linked alginate injected (treated) and the PBS injected (control) groups were analyzed by unpaired t test. All tests were two-tailed and p<0.05 was considered statistically significant.

Results

Figure 37:
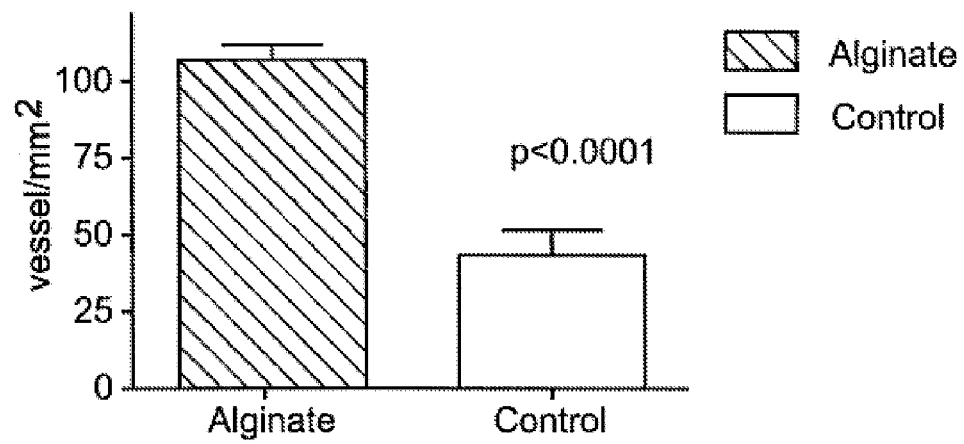
FIG. 37 illustrates the effect of the cross-linked alginate solution, injected into rat myocardium two months post MI, on the average vessel density in the myocardial scar tissue measured four months post MI. The average vessel density in the alginate-treated animals was 106±5 vessels/mm$^2$, compared with just 43±8 vessels/mm$^2$ in the PBS-treated (control) animals (p<0.0001)

Administration of cross-linked alginate solution into a damaged myocardium (two months post MI) significantly increased the density of blood vessels in the myocardium scar tissue [106±5 vessels/mm$^2$ in treated animals, as compared with only 43±8 vessels/mm$^2$ in PBS-treated (control) animals; p<0.0001; FIG. 37].

In addition, the cross-linked alginate solution significantly increased the average scar thickness (from 16.3±3.1 mm in the control animals to 27.9±2.7 mm in the treated animals; p<0.01;.

Figure 38:
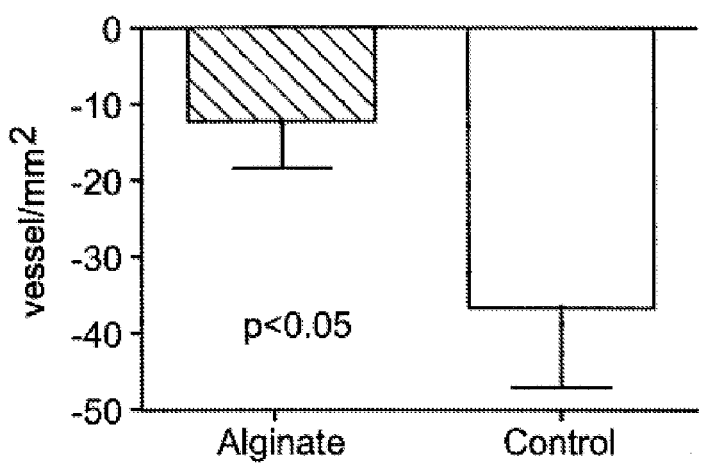
FIG. 38 illustrates the effect of the cross-linked alginate solution injected into a rat myocardium two months post MI, on the LV fractional shortening (FS) measured by 2D-echocardiography four months post MI. The fractional shortening in the PBS-treated (control) rats declined by 37±9% (relative to the pre MI level), compared with just 12±6% in the alginate-treated rats p<0.0001)

2D echocardiography analyses show that the average LV fractional shortening in control animals declined (relative to pre MI levels) by 37±9%, while the average decline in treated animals was only 12±6% (p<0.05; FIG. 38).

Figure 39:
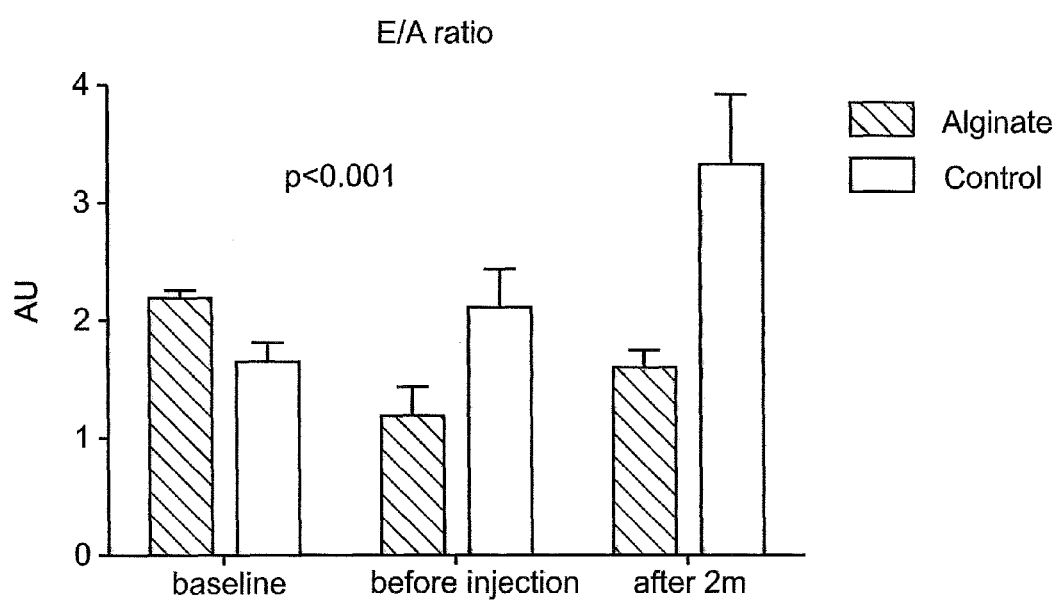
FIG. 39 illustrates the effect of the cross-linked alginate solution, injected into rat myocardium two months post MI, on the cardiac diastolic function measured by E/A wave ratio in Doppler echocardiogram four months post MI. The cardiac diastolic function in the PBS-treated (control) rats declined (relative to the pre MI level) by 37±9%, compared with just 12±6% in the alginate-treated rats (p<0.0001).

Analyses of E/A wave ratio in Doppler echocardiogram show that the average cardiac diastolic function in control animals declined (relative to pre MI levels) by 3.34±0.5%, while the average decline in treated animals was only 1.73±0.09% (p<0.0001; FIG. 39).

The results clearly indicate that the cross-linked alginate solution is capable of promoting angiogenesis, increasing scar thickness and preserving the systolic and diastolic function in a chronically damaged myocardium.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications mentioned in this specification are herein incorporated in their entirety by reference into the specification, to the same extent as if each individual publication, patent, patent application was specifically and individually indicated to be incorporated herein by reference. In addition, citation or identification of any reference in this application shall not be construed as an admission that such reference is available as prior art to the present invention.

What is claimed is:

1. A method of producing a therapeutic composition for treatment of a damaged body tissue, comprising: (a) providing an aqueous solution of an alginate and calcium cations, said alginate being present in an amount ranging from 0.1 to 4% (w/v) with a molecular weight ranging from 1 to 300 kDa and said calcium cations being present in an amount ranging from 0.025 to 0.035% (w/v); and (b) mixing said aqueous solution under conditions suitable for uniformly cross linking the alginate with the calcium cations such that the therapeutic composition has an elastic response equal to or greater than a viscous response, thereby producing the therapeutic composition for treatment of the damaged body tissue.

2. The method of claim 1, wherein said alginate is sodium alginate.

3. The method of claim 2, wherein said sodium alginate has a molecular weight ranging from 5 to 200 kDa.

4. The method of claim 2, wherein said sodium alginate has a molecular weight ranging from 10 to 100 kDa.

5. The method of claim 2, wherein said sodium alginate has a molecular weight ranging from 20 to 50 kDa.

6. The method of claim 2, wherein a ratio between .alpha.-L-guluronic acid and .beta.-D-mannuronic acid in said sodium alginate ranges between 1:1 and 3:1.

7. The method of claim 2, wherein a monomer ratio between .alpha.-L-guluronic acid and .beta.-D-mannuronic acid in said sodium alginate ranges between 1.5:1 and 2.5:1.

8. The method of claim 2, wherein a monomer ratio between .alpha.-L-guluronic acid and .beta.-D-mannuronic acid in said sodium alginate is about 2.

9. The method of claim 1, wherein said calcium cations are provided by a calcium salt.

10. The method of claim 9, wherein said calcium salt is calcium gluconate.

11. The method of claim 1, wherein said calcium cations and said alginate have a ratio between 2:1 and 1:10.

12. The method of claim 1, wherein said calcium cations and said alginate have a ratio between 1:1 and 1:6.

13. The method of claim 1, wherein said calcium cations and said alginate have a ratio between 1:2 and 1:5.

14. The method of claim 1, wherein said calcium cations and said alginate have a ratio between 1:3 and 1:4.

15. The method of claim 1, wherein said mixing is effected by using a homogenizer.

16. The method of claim 15, wherein said homogenizer is operated at a speed setting ranging from 2,000 to 50,000 rpm.

17. The method of claim 15, wherein said homogenizer is operated at a speed setting ranging from 5,000 to 40,000 rpm.

18. The method of claim 1, wherein said mixing is effected at a speed setting ranging from 10,000 to 30,000 rpm.

19. The method of claim 1, wherein said mixing is effected over a period of at least 30 seconds.

20. The method of claim 1, wherein said mixing is effected over a period of at least 1 minute.

21. The method of claim 1, wherein said mixing is effected over a period of at least 2 minutes.

22. The method of claim 1, wherein said alginate is present in an amount ranging from 0.5 to 2% (w/v).

23. The method of claim 22, wherein said alginate is present in an amount ranging from 0.8 to 1.5% (w/v).

24. The method of claim 23, wherein said alginate is present in an amount of about 1% (w/v).

* * * * *